(12) United States Patent
Behrens et al.

(10) Patent No.: US 9,982,302 B2
(45) Date of Patent: May 29, 2018

(54) BIOLOGICAL MARKERS AND METHODS FOR PREDICTING RESPONSE TO B-CELL ANTAGONISTS

(71) Applicant: Genentech, Inc., South San Francisco, CA (US)

(72) Inventors: Timothy W. Behrens, Burlingame, CA (US); Kasia Owczarczyk, London (GB); Michael J. Townsend, San Jose, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days. days.

(21) Appl. No.: 15/019,615

(22) Filed: Feb. 9, 2016

(65) Prior Publication Data

US 2016/0265056 A1      Sep. 15, 2016

Related U.S. Application Data

(63) Continuation of application No. 13/974,817, filed on Aug. 23, 2013, now abandoned, which is a continuation of application No. PCT/US2012/026774, filed on Feb. 27, 2012.

(60) Provisional application No. 61/527,525, filed on Aug. 25, 2011, provisional application No. 61/447,518, filed on Feb. 28, 2011.

(51) Int. Cl.
*C12Q 1/68* (2018.01)
*C07K 14/705* (2006.01)
*A61K 38/00* (2006.01)

(52) U.S. Cl.
CPC ...... *C12Q 1/6883* (2013.01); *C07K 14/70521* (2013.01); *C12Q 1/6886* (2013.01); *A61K 38/00* (2013.01); *C07K 2319/30* (2013.01); *C12Q 2600/106* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,484,892 A | 1/1996 | Tedder et al. | |
| 5,595,721 A | 1/1997 | Kaminski et al. | |
| 5,677,180 A | 10/1997 | Robinson et al. | |
| 5,736,137 A | 4/1998 | Anderson et al. | |
| 6,183,744 B1 | 2/2001 | Goldenburg | |
| 7,074,403 B1 | 7/2006 | Goldenburg et al. | |
| 8,728,730 B2 | 5/2014 | Dennis et al. | |
| 2003/0219433 A1 | 11/2003 | Hansen et al. | |
| 2004/0258682 A1 | 12/2004 | Leung et al. | |
| 2005/0070689 A1 | 3/2005 | Dixit et al. | |
| 2005/0095243 A1 | 5/2005 | Chan et al. | |
| 2005/0163775 A1 | 7/2005 | Chan et al. | |
| 2006/0024295 A1 | 2/2006 | Brunetta | |
| 2006/0110387 A1 | 5/2006 | Brunetta | |
| 2007/0071760 A1 | 3/2007 | Broly et al. | |
| 2007/0105133 A1 | 5/2007 | Clarke et al. | |
| 2009/0204489 A1 | 8/2009 | Behrens et al. | |
| 2010/0285007 A1 | 11/2010 | Davis | |
| 2014/0154247 A1 | 6/2014 | Behrens et al. | |
| 2014/0341887 A1 | 11/2014 | Dennis et al. | |

FOREIGN PATENT DOCUMENTS

| | | |
|---|---|---|
| EP | 0 869 180 A1 | 10/1998 |
| EP | 1 504 035 B1 | 3/2010 |
| EP | 1 476 120 B1 | 9/2010 |
| EP | 2 447 374 A2 | 5/2012 |
| WO | WO-98/18921 A1 | 5/1998 |
| WO | WO-98/27114 A2 | 5/1998 |
| WO | WO-98/27114 A3 | 5/1998 |
| WO | WO-99/12964 A2 | 3/1999 |
| WO | WO-99/12964 A3 | 3/1999 |
| WO | WO-99/33980 A2 | 7/1999 |
| WO | WO-99/33980 A3 | 7/1999 |
| WO | WO-99/33980 A9 | 7/1999 |
| WO | WO-00/40716 A2 | 7/2000 |
| WO | WO-01/12812 A2 | 2/2001 |
| WO | WO-01/12812 A3 | 2/2001 |
| WO | WO-01/87979 A2 | 11/2001 |
| WO | WO-02/02641 A1 | 1/2002 |
| WO | WO-02/16312 A2 | 2/2002 |
| WO | WO-02/16312 A3 | 2/2002 |
| WO | WO-02/16412 A2 | 2/2002 |
| WO | WO-02/16412 A3 | 2/2002 |
| WO | WO-02/024909 A2 | 3/2002 |
| WO | WO-02/24909 A2 | 3/2002 |
| WO | WO-02/24909 A3 | 3/2002 |

(Continued)

OTHER PUBLICATIONS

Haynes et al Electrophoresis. 1998. 19: 1862-1871.*
Gokmen-Polar et al. Cancer Research. 2001. 61: 1375-1381.*
'Enbrel: Other Dangerous RA Treatments' (Found on the Remicade (Infliximab) Side Effects Lawsuits web page (www.remicade-infliximab.com/pages/enbrel_embrel.html)) pp. 1-2 (2004).
Abbas et al., "Immune response in silico (IRIS): immune-specific genes identified from a compendium of microarray expression data" Genes Immun 6:319-31 (2005).
Acosta-Rodriguez et al., "BAFF and LPS cooperate to induce B cells to become susceptible to CD95/Fas-mediated cell death" Eur J Immunol 37(4):990-1000 (2007).
Aggarwal et al., "Human tumor necrosis factor" J Biol Chem 260(4):2345-2354 (1985).

(Continued)

*Primary Examiner* — Carla J Myers
(74) *Attorney, Agent, or Firm* — Morrison & Foerster LLP

(57) ABSTRACT

Biological markers that predict patient responsiveness to B-cell antagonists are provided. Also provided are methods of using such biological markers. In addition, methods for identifying patients suffering from an autoimmune disease, e.g., rheumatoid arthritis, who are not likely to respond to B-cell antagonists are provided, as are methods of treating such patients. Methods for selecting therapeutic agents to treat such patients are also provided.

6 Claims, 9 Drawing Sheets

(56) References Cited

FOREIGN PATENT DOCUMENTS

| WO | WO-02/24909 R6 | 3/2002 |
|---|---|---|
| WO | WO-02/38766 A2 | 5/2002 |
| WO | WO-02/38766 A3 | 5/2002 |
| WO | WO-02/066516 A2 | 8/2002 |
| WO | WO-02/066516 A3 | 8/2002 |
| WO | WO-02/092620 A2 | 11/2002 |
| WO | WO-02/092620 A3 | 11/2002 |
| WO | WO-2003/002607 A1 | 1/2003 |
| WO | WO-03/014294 A2 | 2/2003 |
| WO | WO-03/014294 A3 | 2/2003 |
| WO | WO-03/035846 A2 | 5/2003 |
| WO | WO-03/035846 A3 | 5/2003 |
| WO | WO-03/072736 A2 | 9/2003 |
| WO | WO-2004/035607 A2 | 4/2004 |
| WO | WO-2004/056312 A2 | 7/2004 |
| WO | WO-2005/000351 A2 | 1/2005 |
| WO | WO-2006/068867 A1 | 6/2006 |
| WO | WO-2007/038501 A2 | 4/2007 |
| WO | WO-2007/038501 A3 | 4/2007 |
| WO | WO-2007/135568 A2 | 11/2007 |
| WO | WO-2007/135568 A3 | 11/2007 |
| WO | WO-2008/056198 A1 | 5/2008 |
| WO | WO-2008/104608 A1 | 9/2008 |
| WO | WO-2008/132176 A2 | 11/2008 |
| WO | WO-2008/132176 A3 | 11/2008 |
| WO | WO-2008/154423 A2 | 12/2008 |
| WO | WO-2008/156494 A1 | 12/2008 |
| WO | WO-2009/062125 A1 | 5/2009 |
| WO | WO-2010/149810 A2 | 12/2010 |
| WO | WO-2011/028945 A1 | 3/2011 |
| WO | WO-2012/118750 A2 | 9/2012 |
| WO | WO-2012/118750 A3 | 9/2012 |

OTHER PUBLICATIONS

Alamanosa et al., "Epidemiology of adult rheumatoid arthritis" Autoimmun Rev 4:130-136 (2005).
Alarcon et al., "Radiographic evidence of disease progression in methotrexate treated and nonmethotrexate disease modifying antirheumatic drug treated rheumatoid arthritis patients: a meta-analysis" J Rheumatol 19(12):1868-73 (1992).
Albert et al., "Modeling therapeutic strategies in rheumatoid arthritis: use of decision analysis and Markov models" J Rheumatol 27(3):644-52 (2000).
American College of Rheumatology Subcommittee on Rheumatoid Arthritis Guidelines, "Guidelines for the management of rheumatoid arthritis" Arthritis Rheum 46(2):328-346 (2002).
Antonio et al., "Identification of Candidate Genes for Rituximab Response in Rheumatoid Arthritis Patients by Microarray Expression Profiling in Blood Cells," Pharmacogenomics 10(10):1697-1708 (2009).
Anolik et al., "Rituximab improves peripheral B cell abnormalities in human systemic lupus erythematosus" Arthritis Rheum 50(11):3580-3590 (2004).
Avouac et al., "Diagnostic and predictive value of anti-cyclic citrullinated protein antibodies in:rheumatoid arthritis: a systematic literature review" Ann Rheum Dis 65(7):845-851 (2006).
Badot et al., "Gene expression profiling in the synovium identifies a predictive signature of absence of response to adalimumab therapy in rheumatoid arthritis" Arthritis Res Ther (Epub Apr. 23, 2009), 11:R57 (2009).
Bathon et al., "A comparison of etanercept and methotrexate in patients with early rheumatoid arthritis" New Engl J Med 343(22):1586-93 (2000).
Benucci et al., "Predictive Factors of Response to Rituximab Therapy in Rheumatiod Arthritis: What do we Know Today?," Autoimmun Rev 9(12):801-803 (2010).
Bodmer et al., "The molecular architecture of the TNF superfamily" Trends Biochem Sci 27(1):19-26 (2002).
Boers et al., "Randomised comparison of combined step-down prednisolone, methotrexate and sulphasalazine with sulphasalazine alone in early rheumatoid arthritis" Lancet 350:309-318 (1997).
Breedveld et al., "Association between baseline radiographic damage and improvement in physical function after treatment of patients with rheumatoid arthritis" Ann Rheum Dis 64(1):5255 (2005).
Bresnihan et al., "Treatment of rheumatoid arthritis with recombinant human interleukin-1 !receptor antagonist" Arthritis Rheum 41(12):2196-2204 (1998).
Bukhari et al., "Rheumatoid factor is the major predictor of increasing severity of radiographic erosions in rheumatoid arthritis: results from the Norfolk Arthritis Register Study, a large inception cohort" Arthritis Rheum 46(4):906-12 (2002).
Cambridge et al., "Circulating levels of B lymphocyte stimulator in patients with rheumatoid arthritis following rituximab treatment" Arthritis Rheum 54(3):723-732 (2006).
Campbell et al., "Severe inflammatory arthritis and lymphadenopathy in the absence of TNF" J Clin Invest 107:1519-1527 (2001).
Cheema et al., "Elevated serum B lymphocyte stimulator levels in patients with systemic immune-based rheumatic diseases" Arthritis Rheum 44:1313-1319 (2001).
Childs et al., "Efficacy of etanercept for wear debris-induced osteolysis" J Bone Mineral Res 16(2):338-347 (2001).
Ciotti et al., "Reliability and reproducibility of a RNA preamplification method for low-density array analysis from formalin-fixed paraffin-embedded breast cancer samples" Diagn Mol Pathol 18(2):112-118 (2009).
Claudio et al., GAFF-induced NEMO-independent processing of NF-kB2 in maturing B cells Nature Immunol 3(10):958-965 (2002).
Clavel et al., "Induction of macrophage secretion of tumor necrosis factor a through Fcy receptor IIa engagement by rheumatoid arthritis-specific autoantibodies to citrullinated proteins complexed with fibrinogen" Arthritis Rheum 58(3):678-688 (2008).
Cohen et al., "Rituximab for rheumatoid arthritis refractory to anti-tumor necrosis factor therapy: Results of a multicenter, randomized, double-blind, placebo-controlled, phase III trial evaluating primary efficacy and safety at twenty-four weeks" Arthritis Rheum 54(9):2793-2806 (2006).
Coleman. "Of mouse and man—what is the value of the mouse in predicting gene expression in humans?," Drug Discovery Today. 8: 233-235, (2003).
Cross et al., "Rituximab reduces B cells and T cells in cerebrospinal fluid of multiple sclerosis patients" J Neuroimmunol 180:63-70 (2006).
Csuka et al., "Treatment of intractable rheumatoid arthritis with combined cyclophosphamide, azathioprine, and hydroxychloroquine. A follow-up study" J Am Medical Assn 255(17):2315-9 (1986).
Cuchacovich et al., "Precision of the Larsen and the Sharp methods of assessing radiologic change in patients with rheumatoid arthritis" Arthritis Rheum 35(7):736-739 (1992).
Dass et al., "Highly sensitive B cell analysis predicts response to rituximab therapy in rheumatoid arthritis" Arthritis Rheum 58(10):2993-2999 (2008).
Di Franco et al., "Relationship of rheumatoid factor isotype levels with joint lesions detected by magnetic resonance imaging in early rheumatoid arthritis" Rev Rhum Engl Ed 66(5):251-5 (1999).
Dorner et al., "Targeting B cells in immune-mediated inflammatory disease: A comprehensive review of mechanisms of action and identification of biomarkers" Pharm Ther 125:464-475 (2010).
Douni et al., "Transgenic and knockout analyses of the role of TNF in immune regulation and disease pathogenesis" J Inflammation 47( Suppl 27-38) (1996).
Drossaers-Bakker et al., "A comparison of three radiologic scoring systems for the long-term assessment of rheumatoid arthritis" Arthritis Rheum 43(7):1465-1472 (2000).
Edmonds et al., "Antirheumatic drugs: A proposed new classification" Arthritis Rheum 36(3):336-340 (1993).
Edwards et al., "Do self-perpetuating B lymphocytes drive human autoimmune disease?" Immunology 97(2):188-96 (1999).
Emery et al., "Efficacy and safety of different doses and retreatment of rituximab: a randomised, placebo-controlled trial in patients who are biological naïve with active rheumatoid arthritis and an inad-

(56) References Cited

OTHER PUBLICATIONS equate response to methotrexate (Study Evaluating Rituximab's Efficacy in MTX iNadequate rEsponders (SERENE))" Ann Rheum Dis 69:1629-1635 (2010).
Emery et al., "The efficacy and safety of rituximab in patients with active rheumatoid arthritis despite methotrexate treatment: results of a phase IIB randomized, double-blind, placebo-controlled, dose-ranging trial" Arthritis Rheum 54(5):1390-1400 (2006).
Eriksson, "Nine patients with anti-neutrophil cytoplasmic antibody-positive vasculitis successfully treated with rituximab" J Intern Med 257(6):540-548 (2005).
Eriksson, "Short-term outcome and safety in 5 patients with ANCA-positive vasculitis treated with rituximab" Kidney Blood Press R (Abstract P87), 26:294 (2003).
Fauci et al., "Wegener's granulomatosis: Studies in eighteen patients and a review of the literature" Medicine 52(6):535-561 (1973).
Feldmann et al., "Rheumatoid arthritis" Cell 85:307-310 (1996).
Felson et al., "American College of Rheumatology, preliminary definition of improvement in rheumatoid arthritis" Arthritis Rheum 38(6):727-735 (1995).
Fex et al., "Development of radiographic damage during the first 5-6 yr of rheumatoid arthritis. A prospective follow-up study of a Swedish cohort" Br J Rheumatol 35(11):1106-15 (1996).
Finis et al., "Analysis of pigmented villonodular synovitis with genome-wide complementary approaches" Arthritis Rheum 54(3)1009-1019 (2006).
Finkielman et al., "ANCA are detectable in nearly all patients with active severe Wegener's granulomatosis" Am J Med 120:643.e9-643.E14 (2007).
Forre et al., "Radiologic evidence of disease modification in rheumatoid arthritis patients treated with cyclosporine. Results of a 48-week multicenter study comparing low-dose cyclosporine with placebo. Norwegian Arthritis Study Group" Arthritis Rheum 37(10):1506-12 (1994).
Furst et al., "Updated consensus statement on biological agents for the treatment of rheumatic diseases, 2008" Ann Rheum Dis 67( Suppl III):iii2-iii25 (2008).
Gaffo et al., "Treatment of Rheumatoid Arthritis," Am J Health Syst Pharm 63(24):2451-2465 (2006).
Genovese et al., "Etanercept versus methotrexate in patients with early rheumatoid arthritis: two-year radiographic and clinical outcomes" Arthritis Rheum 46(6):1443-50 (2002).
Genovese et al., "Safety and clinical activity of ocrelizumab (a humanized antibody targeting CD20+ B cells) in combination with methotrexate (MTX) in moderate-severe rheumatoid arthritis (RA) patients (pts) (Ph I/II action study)" Arthritis Rheum (Abstract 6), 54( Suppl 9):566-567 (2006).
Goldring et al., "Mechanisms of bone loss in inflammatory arthritis: diagnosis and therapeutic implications" Arthritis Res 2:33-37 (2000).
Graudal et al., "Radiographic progression in rheumatoid arthritis" Arthritis Rheum 41(8):1470-1480 (1998).
Groom et al., "Association of BAFF/BLyS overexpression and altered B cell differentiation with Sjogren's syndrome" J Clin Invest 109:59-68 (2002).
Gross et al., "TALI and BCMA are receptors for a TNF homologue implicated in B-cell autoimmune disease" Nature 404:995-999 (2000).
Guillevin et al., "Microscopic Polyangiitis" Arthritis Rheum 42(3):421-430 (1999).
Haas et al. "Identification of genes modulated in rheumatoid arthritis using complementary DNA microarray analysis of lymphoblastoid B cell lines from disease-discordant monozygotic twins," Arthritis Rheum 54: 2047-2060 (2006).
Hagmann, "Doing Immunology on a Chip" Science 290:82-83 (Oct. 2000).
Hanke et al. "Detailed technical analysis of urine RNA-based tumor diagnostics reveals ETS2/urokinase plasminogen activator to be a novel marker for bladder cancer," Clinical Chemistry 53: 2070-2077 (2007).
Hannonen et al., "Sulfasalazine in early rheumatoid arthritis. A 48-week double-blind, prospective, placebo-controlled study" Arthritis Rheum 36(11):1501-9 (1993).
Hardy et al., "B cell development pathways" Annu Rev Immunol 19:595-621 (2001).
Harris et al., "Reciprocal regulation of polarized cytokine production oby effector B and T cells" Nature Immunol 1(6):475-482 (2000).
Harris et al., "The World Health Organization classification of neoplasms of the hematopoietic and lymphoid tissues: Report of the Clinical Advisory Committee Meeting—Airlie House, Virginia, Nov. 1997" Hematology J 1:53-66 (2000).
Hauser et al., "B-cell depletion with rituximab in relapsing-remitting multiple sclerosis" New Engl J Med 358(7):676-688 (2008).
Hawker et al., "Rituximab in patients with primary progressive multiple sclerosis: results of a randomized double-blind placebo-controlled multicenter trial" Ann Neurol 66(4):460-471 (2009).
Heliovaara et al., "Rheumatoid factor, chronic arthritis and mortality" Ann Rheum Dis 54:811-814 (1995).
Hofbauer et al., "The roles of osteoprotegerin and osteoprotegerin ligand in the paracrine regulation of bone resorption" J Bone Miner Res 15(1):2-12 (2000).
Hoffman et al., "Wegener Granulomatosis: An analysis of 158 patients" Ann Intern Med 116:488-498 (1992).
Huber et al., "Identification of intra-group, inter-individual, and gene-specific variances in mRNA expression profiles in the rheumatoid arthritis synovial membrane" Arthritis Res Ther 10(4):R98 (2008).
Hulsmans et al., "The course of radiologic damage during the first six years of rheumatoid arthritis" Arthritis Rheum 43(9):1927-1940 (2000).
International Search Report on patentability for International Patent Application No. PCT/US2012/026774.
Jaimes et al., "Maturation and trafficking markers on rotavirus-specific B cells during acute infection and convalescence in children" J Virol 78(20):10967-10976 (2004).
Janeway et al., "The B cell is the initiating antigen-presenting cell in peripheral lymph nodes" J Immunol 138(4):1051-1055 (1987).
Jayne et al., "A prospective, open label trial of 13-cell depletion xvith Rituximah in reffactory systemic vasculitis" J Am Soc Nephrol 14:755A (2003).
Jayne et al., "A randomized trial of maintenance therapy for vasculitis associated with antineutrophil cytoplasmic autoantibodies" New Engl J Med 349:36-44 (2003).
Jayne et al., "B-cell depletion with rituximab for refractory vasculitis" Kidney Blood Press R (Abstract P88), 26:294-295 (2003).
Jennette et al., "Nomenclature of systemic vasculitides, proposal of an international consensus conference" Arthritis Rheum 37(2):187-192 (1994).
Jeurissen et al., "Influence of methotrexate and azathioprine on radiologic progression in rheumatoid arthritis. A randomized, double-blind study" Ann Intern Med 114(12):999-1004 (1991).
Joint Committee, "A comparison of prednisolone with aspirin or other analgesics in the treatment of rheumatoid arthritis. A second report by the joint committee of the Medical Research Council and Nuffield Foundation on clinical trials of cortisone, ACTH, and other therapeutic measures in chronic rheumatic diseases" Ann Rheum Dis 19:331-337 (1960).
Kaarela et al., "Continuous progression of radiological destruction in seropositive rheumatoid arthritis" J Rheumatol 24(7):1285-7 (Jul. 1997).
Kayagaki et al., "BAFF/BLyS receptor 3 binds the B cell survival factor BAFF ligand through a iscrete surgace loop and promotes processing of NF-KB2" Immunity 10:515-524 (2002).
Keogh et al. et al., "Induction of remission by B lymphocyte depletion in eleven patients with refractory antineutrophil cytoplasmic antibody-associated vasculitis" Arthritis Rheum 52(1):262-268 (2005).

(56) References Cited

OTHER PUBLICATIONS

Keogh et al., "Rituximab—A potential mechanistic-based therapy for treatment of refractory ANCA-associated vasculitis" Kidney Blood Press Res (Abstract #032), 26:293 (2003).
Keystone et al., "Adalimumab (D2E7), a fully human anti-TNF-a monoclonal antibody, inhibits the progression of structural joint damage in patients with active RA despite concomitant methotrexate therapy" Arthritis Rheum (#468), 46( Suppl 9):S205 (2002).
Khare et al., "Severe B cell hyperplasia and autoimmune disease in TALL-1 transgenic mice" Proc Natl Acad Sci USA 97(7):33770-3375 (2000).
Kirwan et al., "The effect of glucocorticoids on joint destruction in rheumatoid arthritis. The Arthritis and Rheumatism Council Low-Dose Glucocorticoid Study Group" New Engl J Med 333(3):142-6 (1995).
Lal et al., "Inflammation and autoantibody markers identified rheumatoid arthritis patients with enhanced clinical benefit following ribuximan treatment," Arthritis Rheum 63(12):3681-3691 (2011).
Landewe et al., "COBRA combination therapy in patients with early rheumatoid arthritis longterm structural benefits of a brief intervention" Arthritis Rheum 46(2):347-56 (2002).
Larsen et al., "Radiographic evaluation of rheumatoid arthritis and related conditions by standard reference films" Acta Radiologica Diagnosis 18(4):481-91 (1977).
Lassere et al., "Smallest detectable difference in radiological progression" J Rheumatol 26:731-9 (1999).
Leandro et al., "Reconstitution of peripheral blood B cells after depletion with rituximab in patients with rhematoid arthritis" Arthritis Rheum 54(2):613-620 (2006).
Li et al., "Inferring causal relationships among intermediate phenotypes and biomarkers: a case study of rheumatoid arthritis" Bioinformatics 22(12):1503-7 (2006).
Lindberg et al., "Effect of infliximab on mRNA expression profiles in synovial tissue of rheumatoid arthritis patients" Arthritis Res Ther 8(6):R179 (2006).
Lipsky et al., "Infliximab and methotrexate in the treatment of rheumatoid arthritis. Anti-tumor necrosis factor trial in rheumatoid arthritis with concomitant therapy study group" New Engl J Med 343(22):1594-1602 (2000).
Liu et al. "Comparison of differentially expressed genes in T lymphocytes between human autoimmune disease and murine models of autoimmune disease," Clinical Immunology 112: 225-230, (2004).
MacKay et al., "BAFF and APRIL: A tutorial on B cell survival" Annu Rev Immunol : 21:231-264 (2003).
Mackay et al., "Mice transgenic for BAFF develop lymphocytic disorders along with autoimmune manifestations" J Exp Med 190(11):1697-1710 (1999).
Maini et al., "Infliximab (chimeric anti-tumour necrosis a factor monoclonal antibody) versus placebo in rheumatoid arthritis patients receiving concomitant methotrexate: a randomised phase III trial" Lancet 354:1932-39 (1999).
Martin et al., "B cell immunobiology in disease: evolving concepts from the clinic" Annu Rev Immunol 24:467-496 (2006).
Min et al. "Variability of gene expression profiles in human blood and lymphoblastoid cell lines," BMC Genomics 11:96 (2010).
Moir et al., "B cells in HIV infection and disease" Nature Reviews Immunol 9:235-245 (2009).
Moir et al., "Protein secretion systems in microbial and mammalian cells" Bioprocess Technology 9:67-94 (1990).
Moore et al., "BLyS: Member of the tumor necrosis factor family and B lymphocyte stimulator" Science 285(5425):260-263 (1999).
Mottonen et al., "Comparison of combination therapy with single-drug therapy in early rheumatoid arthritis: a randomised trial. FIN-RACo trial group" Lancet 353:1568-73 (1999).
Mukhopadhyay et al., "Identification and Characterization of a Novel Cytokine, THANK, a TNF Homologue That Activates Apoptosis, Nuclear Factor-KB, and c-Jun NH 2-Terminal Kinase" J Biol Chem 274:15978-15981 (1999).

NCBI Database, GenBank Accession No. AF136293, (*Homo sapiens* TNF and ApoL related ligand TALL-1 (TALL1) mRNA, complete cds).
NCBI GenBank. "*Homo sapiens* cDNA, FLJ92289, *Homo sapiens* Immunoglobulin J Polypeptide, Linker Protein for Immunoglobulin Alpha and Mu Polypeptides (IGJ), mRNA," located at <http://www.ncbi.nlm.hih.gov/nuccore/164698145>, last visited on Jul. 28, 2015, 2 pages (2008).
NCBI GenBank. "*Homo sapiens* B Cell Crosslinked IgM-activating Sequence Protein (BXMAS1) mRNA, Complete Cds," located at <http://www.ncbi.nlm.nih.gov/nuccore/AF369794.2>, last visited on Jul. 28, 2015, 3 pages (2001).
NCBI Genbank. "Human CD19 Gene, Completed Cds," located at <http://www.ncbi.nlm.nih.gov/nuccore/M84371.1>, last visited on Jul. 28, 2015, 6 pages (1995).
Ngo et al., "A loss-of-function RNA interference screen for molecular targets in cancer" Nature 441:106-110 (2006).
Novack et al., "Cyclophosphamide therapy in Wegener's granulomatosis" New Engl J Med 284(17):938-942 (1971).
O'Dell et al., "Treatment of rheumatoid arthritis with methotrexate alone, sulfasalazine and hydroxychloroquine, or a combination of all three medications" New Engl J Med 334(20):1287-91 (1996).
Odendahl et al., "Generation of migratory antigen-specific plasma blasts and mobilization of resident plasma cells in a secondary immune response" Blood 105(4):1614-1621 (2005).
Ota, "Immunologic laboratory testing in clinical practice for rheumatoid arthritis" Rinsho Byori 54(8):861-8 (2006).
Owczarczyk et al., "A plasmablast biomarker for nonresponse to antibody therapy to CD20 in rheumatoid arthritis" Science Transl Med 3(101):101RA92 (2011).
Owczarczyk et al. "Elevated blood plasmablast MRNA markers are negative predictors of response to rituximab in rheumatoid arthritis," Ann Rheum Dis. 70 (Suppl 3):69, (2011).
Page, "TreeView: An application to display phylogenetic trees on personal computers" Computer Applications in the Biosciences 12(4):357-358 (1996).
Pagnoux et al., "Predictors of treatment resistance and relapse in antineutrophil cytoplasmic antibody-associated small-vessel vasculitis" Arthritis Rheum 58(9):2908-2918 (2008).
Palanichamy et al., "Modulation of molecular imprints in the antigen-experienced B cell repertoire by rituximab" Arthritis Rheum 58(12):3665-3674 (2008).
Palmer et al. "Cell-type specific gene expression profiles of leukocytes in human peripheral blood," BMC Genomics 7(115):1-15 (2006).
Paulus et al., "Analysis of improvement in individual rheumatoid arthritis patients treated with disease-modifying antirheumatic drugs, based on the findings in patients treated with placebo" Athritis Rheum 33(4):477-484 (1990).
Paulus et al., "Classifying structural joint damage in rheumatoid arthritis as progressive or inonprogressive using a composite definition of joint radiographic change" Arthritis Rheum 50(4):1083-1096 (2004).
Paulus et al., "Monitoring radiographic changes in early rheumatoid arthritis" J Rheumatol 23(5):801-805 (1996).
Pennica et al., "Human tumour necrosis factor: Precursor structure, expression and homology to lymphotoxin" Nature 312:724-729 (1984).
Pillai et al., "Marginal zone B cells" Annu Rev Immunol 23:161-196 (2005).
Pincus et al., "Comparison of 3 quantitative measures of hand radiographs in patients with rheumatoid arthritis: Steinbrocker stage, Kaye modified Sharp score, and Larsen score" J Rheumatol 24(11):2106-12 (1997).
Plant et al., "Measurement and prediction of radiological progression in early rheumatoid arthritis" J Rheumatol 21(10):1808-13 (1994).
Plant et al., "Patterns of radiological progression in early rheumatoid arthritis: results of an 8 year prospective study" J Rheumatol 25(3):417-26 (1998).
Poison et al., "Expression pattern of the human FcRH/IRTA receptors in normal tissue and in B-chronic lymphocytic leukemia" Int Immunol 18(9):1363-1373 (2006).

(56) References Cited

OTHER PUBLICATIONS

Press et al., "Monoclonal antibody 1F5 (Anti-CD20) serotherapy of human B cell lymphomas" Blood 69(2):584-491 (1987).
Prevoo et al., "Modified disease activity scores that include twenty-eight-joint counts; Development and validation in a prospective longitudinal study of patients with rheumatoid arthritis" Arthritis Rheum 38(1):44-48 (1995).
Priolo et al., "Radiographic changes in the feet of patients with early rheumatoid arthritis. GRISAR (Gruppo Reumatologi Italiani Studio Artrite Reumatoide)" J Rheumatol 24:2113-2118 (1997) abstract only.
Pyrpasopoulou et al., "Response to rituximab and timeframe to relapse in rheumatoid arthritis patients" Mol Diagn Ther 14(1):43-48 (2010).
Rantapaa-Dahlqvist et al., "Antibodies against cyclic citrullinated peptide and IgA rheumatoidfactor predict the development of rheumatoid arthritis" Arthritis Rheum 48(10):2741-9 (2003).
Reff et al., "Depletion of B cells in vivo by a chimeric mouse human monoclonal antibody to CD20" Blood 83(2):435-445 (1994).
Reinhold-Keller et al., "An interdisciplinary approach to the care of patients with Wegener's granulomatosis: long-term outcome in 155 patients" Arthritis Rheum 43(5):1021-1032 (2000).
Rioja et al., "Potential novel biomarkers of disease activity in rheumatoid arthritis patients" Arthritis Rheum 58(8):2257-2267 (2008).
Rivera et al., "Role of B cells as antigen-presenting cells in vivo revisited: antigen-specific B cells are essential for T cell expansion in lymph nodes and for systemic T cell responses to low antigen concentrations" Int Immunol 13(12):1583-1593 (2001).
Roll et al., "Anti-CD20 therapy in patients with rheumatoid arthritis. Predictors of response and B cell subset regeneration after repeated treatment" Arthritis Rheum 58(6):1566-1575 (2008).
Russell et al., "The role of anti-cyclic citrullinated peptide antibodies in predicting progression of palindromic rheumatism to rheumatoid arthritis" J Rheumatol 33(7):1240-2 (2006).
Sakurai et al., "Tali attenuates antibody production costimulated by BAFF-R and CD40" Eur J Immunol 37:110-118 (2007).
Schellekens et al., "The diagnostic properties of rheumatoid arthritis antibodies recognizing a cyclic citrullinated peptide" Arthritis Rheum 43(1):155-163 (2000).
Schiemann et al., "An essential role for BAFF in the normal development of B cells through a BCMA-independent pathway" Science 293:2111-2114 (2001).
Schneider et al., "BAFF, a novel ligand of the tumor necrosis factor family, stimulates B cell growth" J Exp Med 189:1747-1756 (1999).
Scott et al., "The links between joint damage and disability in rheumatoid arthritis" Rheumatology 39:122-132 (2000).
Sellam et al., "B cell activation biomarkers as predictive factors for the response to rituximab in rheumatoid arthritis" Arthritis Rheum 63(4):933-938 (2011).
Sharp et al., "How many joints in the hands and wrists should be included in a score ofradiologic abnormalities used to assess rheumatoid arthritis?" Arthritis Rheum 28(12) :1326-35 (1985).
Sharp et al., "Methods of scoring the progression of radiologic changes in rheumatoid arthritis" Arthritis Rheum 14(6):706-720 (1971).
Shu et al., "TALL-1 is a novel member of the TNF family that is down-regulated by mitogens" J Leukocyte Biol 65:680-683 (1999).
Silverman et al., "Roles of B cells in rheumatoid arthritis" Arthritis Res Ther 5(Suppl 4):S1-S6 (2003).
Smith et al., "A prospective, open label trial of B-cell depletion with rituximab in refractory systemic vasculitis" Jam Soc Nephrol (11th International Vasculitis and ANCA workshop), 14(Poster # SU-P0998):755A (2003).
Smolen et al., "[Sat0031] Patients with early rheumatoid arthritis achieved a clinically meaningful and sustained improvement in physical function after treatment with infliximab" Ann Rheum Dis 64(Suppl III):418 (2005).
Smolen et al., "Evidence of radiographic benefit of treatment with infliximab plus methotrexate in rheumatoid arthritis patients who had no. clinical improvement: a detailed subanalysis of data from the anti-tumor necrosis factor trial in rheumatoid arthritis with concomitant therapy study" Arthritis Rheum 52(4):1020-30 (2005).
Specks et al., "Response of Wegener's granulomatosis to anti-CD20 chimeric monoclonal antibody therapy" Arthritis Rheum 44(12):2836-2840 (2001).
Stone et al., "Limited versus severe Wegener's granulomatosis" Arthritis Rheum 48(8):2299-2309 (2003).
Stone et al., "Rituximab versus cyclophosphamide for ANCA-associated vasculitis" New Engl J Med 363(3):221-232 (2010).
Stone et al., "Solid malignancies among patients in the Wegener's granulomatosis etanercept trial" Arthritis Rheum 54(5):1608-1618 (2006).
Strand et al., "Treatment of active rheumatoid arthritis with leflunomide compared with placebo and methotrexate" Arch Intern Med 159:2542-2550 (1999).
Sundberg et al., "The immunomodulatory benzodiazepine Bz-423 inhibits B-Cell proliferation by targeting c-Myc protein for rapid and specific degradation" Cancer Res 66:1775-1782 (2006).
Takemura et al., "T cell activation in rheumatoid synovium is B cell dependent" J Immunol 167(8):4710-4718 (2001).
Teitelbaum, "Bone resorption by osteoclasts" Science 289:1504-1508 (2000).
Teng et al., "Immunohistochemical analysis as a means to predict responsiveness to rituximab treatment" Arthritis Rheum 56(12):3909-3918 (2007).
Thangarajh et al., "A Proliferation-inducing Ligand (APRIL) is Expressed by Astrocytes and is Increased in Multiple Sclerosis" Scandinavian J Immunol 65:92-98 (2007).
Thompson et al., "BAFF-R a Newly Identified Tnf Receptor That Specifically Interacts with BAFF" Science 293:2108-2111 (2001).
Tugwell et al., "Omeract conference on outcome measures in rheumatoid arthritis clinical trials: Introduction" J Rheumatol 20(3):528-530 (1993).
Vallerskog et al., "Differential effects on BAFF and APRIL levels in rituximab-treated patients with systemic lupus erythematosus and rheumatoid arthritis" Arthritis Res Ther 8:R167 (2006).
van der Heijde et al., "[FRIO201] the effect of infliximab therapy on spinal inflammationpatients with ankylosing spondylitis" Ann Rheum Dis 64(Suppl III):317 (2005).
van der Heijde et al., "[FRIO208] the effect of infliximab therapy on bone mineral density in patients with ankylosing spondylitis: Results from assert" Ann Rheum Dis 64( Suppl III):319 (2005).
van der Heijde et al., "[Sat0028] Effect of infliximab and methotrexate on radiographic progression in patients with early rheumatoid arthritis" Ann Rheum Dis 64(Suppl III):417 (2005).
van Der Heijde et al., "Biannual radiographic assessments of hands and feet in a three-year prospective followup of patients with early rheumatoid arthritis" Arthritis Rheum 35(1):26-34 (1992).
van der Heijde et al., "Development of a disease activity score based on judgment in clinical practice by rheumatologists" J Rheumatol 20(3):579-581 (1993).
van der Heijde et al., "Effects of hydroxychloroquine and sulphasalazine on progression of joint damage in rheumatoid arthritis" Lancet 1(8646):1036-8 (May 13, 1989).
van der Heijde et al., "Efficacy and safety of infliximab in patients with ankylosing spondylitis: results of a randomized, placebo-controlled trial (ASSERT)." Arthritis Rheum 52(2):582-591 (2005).
van der Heijde et al., "How should treatment effect on spinal radiographic progression in patients with ankylosing spondylitis be measured?" Arthritis Rheum 52(7):1979-85 (2005).
van der Heijde, "How to read radiographs according to the Sharp/van der Heijde method" J Rheumatol 27:261-3 (2000).
van der Heijde, "Plain x-rays in rheumatoid arthritis: overview of scoring methods, their reliability and applicability" Bailliere's Clin Rheum 10(3):435-453 (1996).
van der Pouw Kraan et al., "Discovery of distinctive gene expression profiles in rheumatoid synovium using cDNA microarray technology: evidence for the existence of multiple pathways of tissue destruction and repair" Genes and Immunity 4:187-196 (2003).

(56) References Cited

OTHER PUBLICATIONS van der Pouw Kraan et al., "Responsiveness to anti-tumour necrosis factor a therapy is related to pre-treatment tissue inflammation levels in rheumatoid arthritis patients" Ann Rheum Dis 67:563-566 (2008).
van der Pouw Kraan et al., "Rheumatoid arthritis is a heterogeneous disease" Arthritis Rheum 48(8):2132-2145 (2003).
van Everdingen et al., "Low-dose prednisone therapy for patients with early active rheumatoid arthritis: clinical efficacy, disease-modifying properties, and side effects: a randomized, double-blind, placebo-controlled clinical trial" Ann Intern Med 136(1):1-12 (2002).
Vital et al., "Management of nonresponse to rituximab in rheumatoid arthritis: predictors of outcome of re-treatment," *Arthritis Rheum.* 62(5):1273-1279 (2010).
Walton, "Giant-cell granuloma of the respiratory tract (Wegener's Granulomatosis)" Br Med J:265-270 (1958).
Wang (Qinwei) et al., "The study of porous silica gel for aqueous size exclusion chromatographic use" Chemical J Chinese Universities (Kao Teng Hsueh Hsia Hua Hsueh Hsueh Pao, abstract in English), 6:557-561 (1985).
Wassenberg et al., "Low dose prendnisolone therapy (LDPT) retards radiographically detectable destruction in early rheumatoid arthritis" Arthritis Rheum 42:S243 (1999).
Wegener's Granulomatosis Etanercept Trial (WGET) Research Group, "Etanercept plus standard therapy for Wegener's granulomatosis" N Engl J Med 352(4):351-361 (2005).
Wegener's Granulomatosis Etanercept Trial Research Group, "Limited versus severe Wegener's granulomatosis" Arthritis Rheum 48(8):2299-2309 (2003).
Weinblatt et al., "The effects of drug therapy on radiographic progression of rheumatoid arthritis. Results of a 36-week randomized trial comparing methotrexate and auranofin" Arthritis Rheum 36(5):613-619 (1993).
Wilson et al., "cDNA cloning of the B cell membrane protein CD22: A mediator of B-B cell interactions" J Exp Med 173:137-146 (1991).
Wilson et al., "Genomic structure and chromosomal mapping of the human CD22 gene" J Immunol 150(11):5013-5024 (1993).
Wolfe et al., "A core set of domains for longitudinal observation studies in rheumatic disorders: Consensus report from Omeract 4" Arthritis Rheum 41(Suppl No. 9):S204 (1998).
Wolfe et al., "Radiographic outcome of recent-onset rheumatoid arthritis" Arthritis Rheum 41(9):1571-1582 (1998).
Wolfe et al., "Radiographic progression predicts substantial income loss and work disability in rheumatoid arthritis" Arthritis Rheum 43(Suppl 9):S403 (2000).
Yan et al., "Activation and accumulation of B cells in TACI-deficient mice" Nature Immunol 2(7):638-643 (2001).
Yan et al., "Identification of a novel receptor for B lymphocyte stimulator that is mutated in a mouse strain with severe B cell deficiency" Curr Biol 11:1547-1552 (2001).
Yan et al., "Identification of a receptor for BLyS demonstrates a crucial role in humoral immunity" Nature Immunol 1(1):37-41 (2000).
Yang et al., "B cell maturation antigen, the receptor for a proliferation-inducing ligand and B cell-activating factor of the TNF family, induces antigen presentation in B cells" J Immunol 175:2814-2824 (2005).
Zhang et al., "Cutting Edge: A role for B lymphocyte stimulator in systemic lupus erythematosus" J Immunol 166:6-10 (2001).
Extended European Search Report and Search Opinion dated Jun. 8, 2015, for European Patent Application No. 12752355.3, filed on Feb. 2, 2012, 10 pages.

* cited by examiner

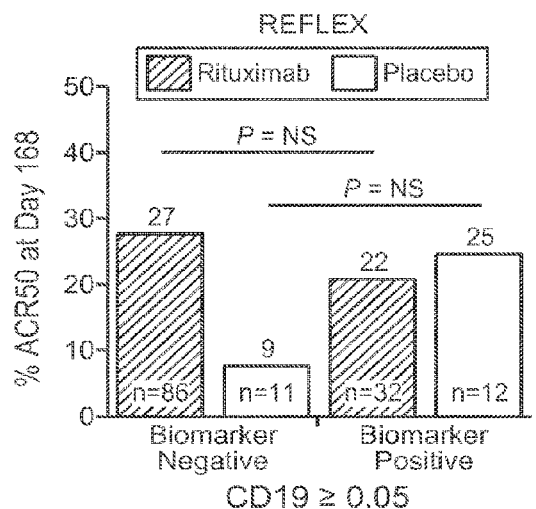
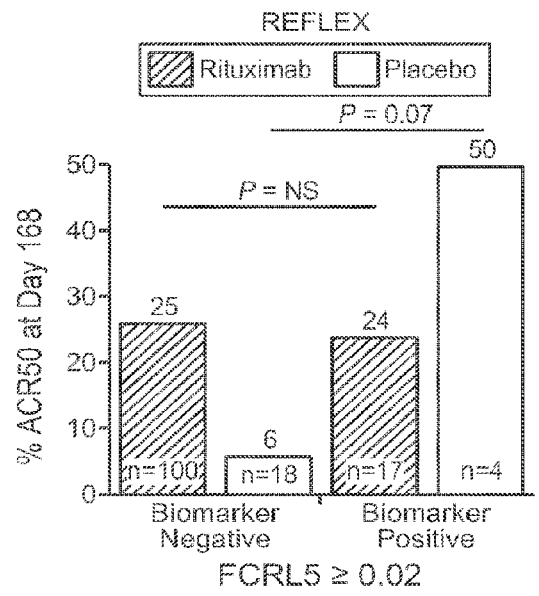
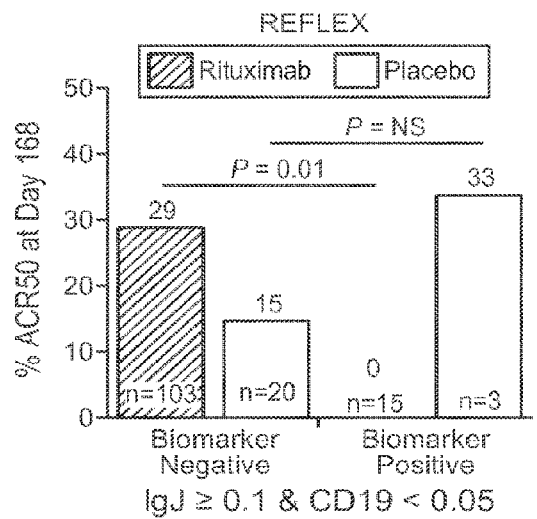
FIG. 2A
FIG. 2B
FIG. 2C

BIOLOGICAL MARKERS AND METHODS FOR PREDICTING RESPONSE TO B-CELL ANTAGONISTS

CROSS REFERENCE TO RELATED APPLICATIONS

This application is a continuation of co-pending U.S. application Ser. No. 13/974,817 filed Aug. 23, 2013, which is a continuation of International Application No. PCT/US2012/026774 having an international filing date of Feb. 27, 2012, which claims the benefit of priority of provisional U.S. Application No. 61/447,518 filed Feb. 28, 2011 and provisional U.S. Application No. 61/527,525 filed Aug. 25, 2011, all of which are hereby incorporated by reference in their entirety.

FIELD

Biological markers that predict patient responsiveness to B-cell antagonists are provided. Also provided are methods of using such biological markers. In addition, methods for identifying patients suffering from an autoimmune disease, e.g., rheumatoid arthritis, who are not likely to respond to B-cell antagonists are provided, as are methods of treating such patients. Methods for selecting therapeutic agents to treat such patients are also provided.

BACKGROUND

B lymphocytes play an important role in the pathogenesis of autoimmune diseases. Certain B-cell depleting therapeutic agents have been shown to be effective for the treatment of various autoimmune diseases, including for example, rheumatoid arthritis (RA), multiple sclerosis (MS) and anti-neutrophil cytoplasmic antibody (ANCA)-associated vasculitis.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called plasmablasts which ultimately differentiate into plasma cells. Memory B cells have a longer life span and continue to express membrane-bound antibody with the same specificity as the original parent cell. Plasma cells do not produce membrane-bound antibody, but instead produce the antibody in a form that can be secreted. Secreted antibodies are the major effector molecules of humoral immunity.

B-cell lymphomas express a cell surface antigen, CD20, and this antigen can serve as a target of therapeutic agents for the treatment of such lymphomas. In essence, such targeting can be generalized as follows: antibodies specific to the CD20 surface antigen of B cells are administered to a patient. These anti-CD20 antibodies specifically bind to the CD20 antigen of (ostensibly) both normal and malignant B cells; the antibody bound to the CD20 surface antigen may lead to the destruction and depletion of neoplastic B cells. Thus, such anti-CD20 antibodies are known as B-cell depleting therapeutic agents.

One such anti-CD20 antibody is rituximab (RITUXAN®) antibody, which is a genetically engineered chimeric murine/human monoclonal antibody directed against the CD20 antigen. Rituximab is the antibody called "C2B8" in U.S. Pat. No. 5,736,137 (Anderson et al.). Rituximab is indicated for the treatment of patients with relapsed or refractory low-grade or follicular, CD20-positive, B-cell non-Hodgkin's lymphoma. In vitro mechanism-of-action studies have demonstrated that rituximab binds human complement and lyses lymphoid B-cell lines through CDC (Reff et al., *Blood*, 83(2):435-445 (1994)). Additionally, it has significant activity in assays for ADCC. Rituximab is FDA approved for not only for therapy of diffuse large B cell lymphoma, chronic lymphocytic leukemia, but also for rheumatoid arthritis (RA) patients with previous inadequate response to TNF antagonist therapies. Importantly, rituximab spares CD20-negative early B cell lineage precursor cells and late B lineage plasma cells in the bone marrow, and treated patients usually begin to replete their peripheral blood B cell pool by 4-6 months.

Rheumatoid arthritis (RA) is a clinically important, chronic systemic autoimmune inflammatory disease affecting between 1.3 and 2.1 million persons in the United States (See, e.g., Alamanosa and Drosos, *Autoimmun. Rev.*, 4:130-136 (2005)). RA is an autoimmune disorder of unknown etiology. Most RA patients suffer a chronic course of disease that, even with currently available therapies, may result in progressive joint destruction, deformity, disability and even premature death. More than 9 million physician visits and more than 250,000 hospitalizations per year result from RA.

Diagnosis of RA typically relies on clinical and laboratory evaluation of a patient's signs and symptoms. Generally, laboratory evaluation of a patient suspected of having RA may include determination of the level of certain antibodies in serum known as rheumatoid factor (RF) and antibodies to cyclic citrullinated peptide (anti-CCP). (See, e.g., Schellekens et al., *Arthritis Rheum.*, 43:155-163 (2000); DiFranco et al., *Rev. Rheum. Engl. Ed.*, 66(5):251-255 (1999); Rantapaa-Dahlqvist et al., *Arthritis Rheum.*, 48:2741-2749 (2003); Li et al., *Bioinformatics* 22(12):1503-1507 (2006); Russell et al., *J. Rheumatol.*, 33(7):1240-1242 (2006); Ota, *Rinsho byori. Jap. J. Clin. Pathol.*, 54(8)861-868 (2006); Avouac et al., *Ann. Rheum. Dis.*, 65(7):845-851 (2006)). While these antibodies are often found in the serum of RA patients, not all RA patients have them. An additional blood test known as the erythrocyte sedimentation rate (ESR) may also be used. An elevated ESR indicates the general presence of an inflammatory process, although not necessarily RA. Further blood tests may be used to assess the level of other factors, such as C-reactive protein (CRP), that have been associated with RA. In addition, radiographic analysis of affected joints may be performed. In sum, such currently available laboratory tests to diagnose RA are imprecise and imperfect.

In certain instances, diagnosis of RA is made if a patient satisfies certain American College of Rheumatology (ACR) criteria. Certain such criteria include morning stiffness in and around the joints lasting for at least 1 hour before maximal improvement; arthritis of three or more joint areas: at least three joint areas have simultaneously had soft tissue swelling or fluid (not bony overgrowth alone) observed by a physician; the 14 possible joint areas (right and left) are proximal interphalangeal (PIP), metacarpophalangeal (MCP), wrist, elbow, knee, ankle, and metatarsophalangeal (MTP) joints; arthritis of hand joints: at least one joint area swollen as above in wrist, MCP, or PIP joint; symmetric arthritis: simultaneous involvement of the same joint areas (as in arthritis of three or more joint areas, above) on both sides of the body (bilateral involvement of PIP, MCP, or MTP joints is acceptable without absolute symmetry); rheumatoid nodules: subcutaneous nodules over bony prominences or extensor surfaces or in juxta-articular regions that are observed by a physician; serum rheumatoid factor:

demonstration of abnormal amounts of serum rheumatoid factor by any method that has been positive in fewer than five percent of normal control patients; radiographic changes: radiographic changes typical of rheumatoid arthritis on posteroanterior hand and wrist X-rays, which must include erosions or unequivocal bony decalcification localized to or most marked adjacent to the involved joints (osteoarthritis changes alone do not qualify). Diagnosis of RA is typically made if a patient satisfies at least four of the above criteria.

In certain instances, a diagnosis of RA is made if a patient has a particular Disease Activity Score (DAS) (see, e.g., Van der Heijde D. M. et al., J Rheumatol, 1993, 20(3): 579-81; Prevoo M. L. et al, Arthritis Rheum, 1995, 38: 44-8). The DAS system represents both current state of disease activity and change. The DAS scoring system uses a weighted mathematical formula, derived from clinical trials in RA. For example, the DAS 28 is 0.56(T28)+0.28(SW28)+0.70 (Ln ESR)+0.014 GH wherein T represents tender joint number, SW is swollen joint number, ESR is erythrocyte sedimentation rate, and GH is global health. Various values of the DAS represent high or low disease activity as well as remission, and the change and endpoint score result in a categorization of the patient by degree of response (none, moderate, good).

Multiple Sclerosis (MS) is an autoimmune demyelinating disorder of the central nervous system that affects the brain and spinal cord. MS generally exhibits a relapsing-remitting course or a chronic progressive course. Relapsing-remitting MS (RRMS) is characterized by partial or total recovery after attacks. Secondary-progressive MS (SPMS) is a relapsing-remitting course which becomes steadily progressive. Attacks and partial recoveries may continue to occur. Primary-progressive MS (PPMS) is progressive from the onset. Symptoms in patients with PPMS generally do not remit—i.e., decrease in intensity. Current treatments for MS include corticosteroids, beta interferons (BETAFERON®, AVONEX®, REBIF®), glatiramer acetate (COPAXONE®), methotrexate, azathioprine, cyclophosphamide, cladribine, baclofen, tizanidine, amitriptyline, carbamazepine (Berkow et al. (ed.), 1999, supra) and natalizumab (TYSABRI®). In addition, consistent with reports implicating B-cells in the pathogenesis of MS, rituximab has shown some clinical activity in RRMS (see, e.g., Cross et al., J. Neuroimmunol. 180:63-70 (2006) and in PPMS (see, e.g., Hawker K et al., Ann Neurol. 66(4):460-71 (2009)).

Wegener's granulomatosis and microscopic polyangiitis are classified as antineutrophil cytoplasmic antibody (ANCA)-associated vasculitides because most patients with generalized disease have antibodies against proteinase 3 or myeloperoxidase. (Jennette J C et al., Arthritis Rheum 37:187-192 (1994); Finkielman J D et al., Am J Med 120(7):643.e9-643.14 (2007)) The ANCA-associated vasculitides affect small-to-medium-size blood vessels, with a predilection for the respiratory tract and kidneys. (Hoffman G S et al., Ann Intern Med 116:488-498 (1992); Guillevin L et al., Arthritis Rheum 42:421-430 (1999); Reinhold-Keller E et al., Arthritis Rheum 43:1021-1032 (2000); Stone J H. Arthritis Rheum 48:2299-2309 (2003)). Cyclophosphamide and glucocorticoids have been the standard therapy for remission induction for nearly four decades. (Novack S N et al., N Engl J Med 284:938-942 (1971); Fauci A S et al., Medicine (Baltimore) 52:535-561 (1973)). More recently, a number of studies have shown that rituximab demonstrates clinical activity in Wegener's granulomatosis and ANCA-vasculitis. (Specks et al. Arthritis & Rheumatism, 44(12): 2836-2840 (2001); Keogh et al., Kidney Blood Press. Res., 26:293 (2003); Eriksson, "Kidney and Blood Pressure Research, 26:294 (2003); Jayne et al., Kidney and Blood Pressure Research, 26:294-295 (2003); Eriksson, J. Internal Med., 257:540-548 (2005); Keogh et al., Arthritis and Rheumatism, 52:262-268 (2005); Stone et al., N. England J. Med. 363(3):221-231 (2010)).

A number of published studies in RA report the attempted identification of reliable biomarkers for diagnostic and prognostic purposes, including biomarkers that can be used to predict patient responsiveness to various therapeutic agents. (See e.g., Rioja et al., Arthritis and Rheum. 58(8):2257-2267 (2008); Pyrpasopoulou et al., Mol. Diagn. Ther. 14(1):43-48 (2010); WO 2004/0009479; WO 2007/0105133; WO 2007/038501; WO 2007/135568; WO 2008/104608; WO 2008/056198; WO 2008/132176; and WO 2008/154423). No clinically validated diagnostic markers, however, e.g., biomarkers, have been identified that enable clinicians or others to accurately define pathophysiological aspects of rheumatoid arthritis, clinical activity, response to therapy, prognosis, or risk of developing the disease. Accordingly, as RA patients seek treatment, there is considerable trial and error involved in the search for therapeutic agent(s) effective for a particular patient. Such trial and error often involves considerable risk and discomfort the the patient in order to find the most effective therapy. Thus, there is a need for more effective means for determining which patients will respond to which treatment and for incorporating such determinations into more effective treatment regimens for rheumatoid arthritis patients.

It would be highly advantageous to have additional diagnostic methods, including molecular-based diagnostic methods, that can be used to objectively identify the presence of and/or classify rheumatic disease in a patient, define pathophysiologic aspects of rheumatoid arthritis, multiple scerlosis or ANCA-vasculitis, as well as clinical activity, response to therapy, including response to treatment with various therapeutic agents, prognosis, and/or risk of developing disease. In addition, it would be advantageous to have molecular-based diagnostic markers associated with various clinical and/or pathophysiological and/or other biological indicators of disease. Thus, there is a continuing need to identify new molecular biomarkers associated with rheumatoid arthritis as well as other autoimmune disorders. Such associations would greatly benefit the identification of the presence of disease in patients or the determination of susceptibility to develop the disease. Such associations would also benefit the identification of pathophysiologic aspects of RA, MS, ANCA-vasculitis, clinical activity, response to therapy, or prognosis. In addition, statistically and biologically significant and reproducible information regarding such associations could be utilized as an integral component in efforts to identify specific subsets of patients who would be expected to significantly benefit from treatment with a particular therapeutic agent, for example where the therapeutic agent is or has been shown in clinical studies to be of therapeutic benefit in such specific patient subpopulation.

The invention described herein meets certain of the above-described needs and provides other benefits.

All references cited herein, including patent applications and publications, are incorporated by reference in their entirety for any purpose.

SUMMARY

The compositions and methods of the invention are based, at least in part, on the discovery that elevated baseline blood levels of certain molecular markers for late B lineage stage plasma/plasmablast cells in RA patients, and in certain embodiments, low baseline blood levels of certain molecular markers for naïve/mature B cells in RA patients, are predictive of responsiveness of RA patients to treatment with B-cell antagonists, e.g., anti-CD20 monoclonal antibodies, and the use of such molecular markers, alone or in combination, to predict patient responsiveness to therapeutic regimens involving B-cell antagonists. In certain embodiments, such molecular markers, alone or in combination, are predictive of responsiveness of patients suffering from certain other autoimmune diseases, e.g., multiple sclerosis, lupus, and ANCA-vasculitis, to treatment with B-cell antagonists.

Accordingly, in one aspect, compositions for predicting the response of a patient to a therapy comprising a B-cell antagonist are provided. In certain embodiments, the composition comprises a biomarker comprising elevated total plasma/plasmablast cell mRNA in a biological sample obtained from a patient compared to the level of total plasma/plasmablast cell mRNA in a biological sample obtained from a control subject or compared to a threshold value for total plasma/plasmablast cell mRNA. In certain embodiments, the composition further comprises a biomarker comprising a low level of total naïve/mature B cell mRNA in the patient's biological sample compared to the level of total naïve/mature B cell mRNA in the control subject's biological sample or compared to a threshold value for total naïve/mature B cell mRNA. In certain embodiments, the biological sample is whole blood. In certain embodiments, the patient is suffering from, or is suspected of suffering from, rheumatoid arthritis. In certain embodiments, the patient is suffering from, or is suspected of suffering from, multiple sclerosis, lupus, or ANCA-vasculitis. In a further embodiment, the patient is suffering from, or is suspected of suffering from, relapsing-remitting multiple sclerosis or primary progressive multiple sclerosis. In certain embodiments, the B-cell antagonist is selected from an anti-CD22 antibody, an anti-CD20 antibody, an anti-BR3 antibody, and a BR3-Fc immunoadhesin. In certain embodiments, the B-cell antagonist is an anti-CD20 antibody. In a further embodiment, the anti-CD20 antibody is selected from rituximab, ibritumomab tiuxetan, tositumomab, ocrelizumab, 1F5, 2H7, and A20. In a still further embodiment, the anti-CD20 antibody is rituximab. In yet another embodiment, the anti-CD20 antibody is ocrelizumab. In certain embodiments, the response predicted to the therapeutic agent comprising the B-cell antagonist is non-response.

In another aspect, the composition comprises a biomarker comprising an elevated expression level of a plasma/plasmablast cell-enriched gene in a biological sample obtained from the patient compared to the expression level of the plasma/plasmablast cell-enriched gene in a biological sample obtained from a control subject. In certain embodiments, the composition comprises a biomarker comprising an elevated expression level of a plasma/plasmablast cell-enriched gene in a biological sample obtained from the patient compared to a threshold value for the plasma/plasmablast cell-enriched gene. In certain embodiments, the plasma/plasmablast cell-enriched gene is IgJ. In certain embodiments, the biomarker comprises mRNA. In certain embodiments, the biological sample is whole blood. In certain embodiments, the patient is suffering from, or is suspected of suffering from, rheumatoid arthritis. In certain embodiments, the patient is suffering from, or is suspected of suffering from, multiple sclerosis, lupus, or ANCA-vasculitis. In a further embodiment, the patient is suffering from, or is suspected of suffering from, relapsing-remitting multiple sclerosis or primary progressive multiple sclerosis. In certain embodiments, the B-cell antagonist is selected from an anti-CD22 antibody, an anti-CD20 antibody, an anti-BR3 antibody, and a BR3-Fc immunoadhesin. In certain embodiments, the B-cell antagonist is an anti-CD20 antibody. In a further embodiment, the anti-CD20 antibody is selected from rituximab, ibritumomab tiuxetan, tositumomab, ocrelizumab, 1F5, 2H7, and A20. In a still further embodiment, the anti-CD20 antibody is rituximab. In yet another embodiment, the anti-CD20 antibody is ocrelizumab. In certain embodiments, the response predicted to the therapeutic agent comprising the B-cell antagonist is non-response.

In yet another aspect, the composition comprises a biomarker comprising a low expression level of a naïve/mature B cell-enriched gene in a patient's biological sample compared to the expression level of the naïve/mature B cell-enriched gene in a control subject's biological sample. In certain embodiments, the composition comprises a biomarker comprising a low expression level of a naïve/mature B cell-enriched gene in a biological sample obtained from the patient compared to a threshold value for the naïve/mature B cell-enriched gene. In certain embodiments, the naïve/mature B cell-enriched gene is FCRL5. In certain embodiments, the naïve/mature B cell-enriched gene is CD19. In certain embodiments, the biomarker comprises mRNA. In certain embodiments, the biological sample is whole blood. In certain embodiments, the patient is suffering from, or is suspected of suffering from, rheumatoid arthritis. In certain embodiments, the patient is suffering from, or is suspected of suffering from, multiple sclerosis, lupus, or ANCA-vasculitis. In a further embodiment, the patient is suffering from, or is suspected of suffering from, relapsing-remitting multiple sclerosis or primary progressive multiple sclerosis. In certain embodiments, the B-cell antagonist is selected from an anti-CD22 antibody, an anti-CD20 antibody, an anti-BR3 antibody, and a BR3-Fc immunoadhesin. In certain embodiments, the B-cell antagonist is an anti-CD20 antibody. In a further embodiment, the anti-CD20 antibody is selected from rituximab, ibritumomab tiuxetan, tositumomab, ocrelizumab, 1F5, 2H7, and A20. In a still further embodiment, the anti-CD20 antibody is rituximab. In yet another embodiment, the anti-CD20 antibody is ocrelizumab. In certain embodiments, the response predicted to the therapeutic agent comprising the B-cell antagonist is non-response.

In yet still another aspect, the composition comprises more than one biomarker. In certain embodiments, the composition comprises a biomarker comprising an elevated expression level of a plasma/plasmablast cell-enriched gene and a biomarker comprising a low expression level of a naïve/mature B cell-enriched gene in a patient's biological sample. In certain embodiments, the expression level of the more than one biomarker in the patient's biological sample is compared to the expression level in a control subject's biological sample. In certain embodiments, the expression level of the more than one biomarker in the patient's biological sample is compared to a threshold value for the plasma/plasmablast cell-enriched gene and a threshold value for the naïve/mature B cell-enriched gene. In certain embodiments, the plasma/plasmablast cell-enriched gene is IgJ and the naïve/mature B cell-enriched gene is FCRL5. In certain embodiments, the plasma/plasmablast cell-enriched gene is IgJ and the naïve/mature B cell-enriched gene is CD19. In certain embodiments, the more than one biomarker comprises mRNA. In certain embodiments, the biological sample is whole blood. In certain embodiments, the patient is suffering from, or is suspected of suffering from, rheumatoid arthritis. In certain embodiments, the patient is suffering from, or is suspected of suffering from, multiple sclerosis, lupus, or ANCA-vasculitis. In a further embodiment, the patient is suffering from, or is suspected of suffering from, relapsing-remitting multiple sclerosis or primary progressive multiple sclerosis. In certain embodiments, the B-cell antagonist is selected from an anti-CD22 antibody, an anti-CD20 antibody, an anti-BR3 antibody, and a BR3-Fc immunoadhesin. In certain embodiments, the B-cell antagonist is an anti-CD20 antibody. In a further embodiment, the anti-CD20 antibody is selected from rituximab, ibritumomab tiuxetan, tositumomab, ocrelizumab, 1F5, 2H7, and A20. In a still further embodiment, the anti-CD20 antibody is rituximab. In yet another embodiment, the anti-CD20 antibody is ocrelizumab. In certain embodiments, the response predicted to the therapeutic agent comprising the B-cell antagonist is non-response.

In another aspect, methods for predicting the response of a patient to a therapy comprising a B-cell antagonist are provided. In certain embodiments, the method comprises measuring in a biological sample obtained from the patient the expression of at least one gene enriched in plasma/plasmablast cells and comparing the expression of the at least one gene in the patient's biological sample to the expression of the same at least one gene in a biological sample obtained from a control subject or to a threshold value for the at least one plasma/plasmablast cell-enriched gene, wherein elevated expression of the at least one gene in the patient's biological sample compared to the expression in the control subject's biological sample or to the threshold value is predictive of response of the patient to the therapy comprising the B-cell antagonist. In certain embodiments, the plasma/plasmablast cell-enriched gene is IgJ. In certain embodiments, measuring the expression of at least one gene comprises measuring mRNA. In a further embodiment, measuring mRNA comprises a PCR method or a microarray chip. In certain embodiments, the biological sample comprises whole blood. In certain embodiments, the patient is suffering from, or is suspected of suffering from, rheumatoid arthritis. In certain embodiments, the patient is suffering from, or is suspected of suffering from, multiple sclerosis, lupus, or ANCA-vasculitis. In a further embodiment, the patient is suffering from, or is suspected of suffering from, relapsing-remitting multiple sclerosis or primary progressive multiple sclerosis. In certain embodiments, the B-cell antagonist is selected from an anti-CD22 antibody, an anti-CD20 antibody, an anti-BR3 antibody, and a BR3-Fc immunoadhesin. In certain embodiments, the B-cell antagonist is an anti-CD20 antibody. In a further embodiment, the anti-CD20 antibody is selected from rituximab, ibritumomab tiuxetan, tositumomab, ocrelizumab, 1F5, 2H7 and A20. In a still further embodiment, the anti-CD20 antibody is rituximab. In yet another embodiment, the anti-CD20 antibody is ocrelizumab. In certain embodiments, the response predicted to the therapeutic agent comprising the B-cell antagonist is non-response.

In still another aspect, the method comprises measuring in the biological sample obtained from the patient the expression of at least one gene enriched in naïve/mature B cells and comparing the expression of the at least one naïve/mature B cell-enriched gene in the patient's biological sample to the expression of the same at least one naïve/mature B cell-enriched gene in the biological sample obtained from the control subject or to a threshold value for the naïve/mature B cell-enriched gene, wherein a low level of expression of the at least one naïve/mature B cell-enriched gene in the patient's biological sample compared to the expression of the same at least one naïve/mature B cell-enriched gene in the control subject's biological sample or to the threshold value for the naïve/mature B cell-enriched gene is predictive of response of the patient to the therapy comprising the B-cell antagonist. In certain embodiments, the naïve/mature B cell-enriched gene is FCRL5. In certain embodiments, the naïve/mature B cell-enriched gene is CD19. In certain embodiments, measuring the expression of at least one gene comprises measuring mRNA. In a further embodiment, measuring mRNA comprises a PCR method or a microarray chip. In certain embodiments, the biological sample comprises whole blood. In certain embodiments, the patient is suffering from, or is suspected of suffering from, rheumatoid arthritis. In certain embodiments, the patient is suffering from, or is suspected of suffering from, multiple sclerosis, lupus, or ANCA-vasculitis. In a further embodiment, the patient is suffering from, or is suspected of suffering from, relapsing-remitting multiple sclerosis or primary progressive multiple sclerosis. In certain embodiments, the B-cell antagonist is selected from anti-CD22 antibody, an anti-CD20 antibody, an anti-BR3 antibody, and a BR3-Fc immunoadhesin. In certain embodiments, the B-cell antagonist is an anti-CD20 antibody. In a further embodiment, the anti-CD20 antibody is selected from rituximab, ibritumomab tiuxetan, tositumomab, ocrelizumab, 1F5, 2H7, and A20. In a still further embodiment, the anti-CD20 antibody is rituximab. In yet another embodiment, the anti-CD20 antibody is ocrelizumab. In certain embodiments, the response predicted to the therapeutic agent comprising the B-cell antagonist is non-response.

In yet another aspect, the method comprises measuring in a biological sample obtained from the patient the expression of at least one gene enriched in plasma/plasmablast cells and the expression of at least one gene enriched in naïve/mature B cells. In certain embodiments, the expression level of the plasma/plasmablast cell-enriched gene(s) and the expression level of the naïve/mature B cell-enriched gene(s) in the patient's biological sample are compared to the expression levels of the same respective genes in a control subject's biological sample. In certain embodiments, the expression level of the plasma/plasmablast cell-enriched gene(s) and the expression level of the naïve/mature B cell-enriched gene(s) in the patient's biological sample are compared to threshold values for the plasma/plasmablast cell-enriched gene(s) and the naïve/mature B cell-enriched gene(s), respectively. In certain embodiments, the plasma/plasmablast cell-enriched gene is IgJ and the naïve/mature B cell-enriched gene is FCRL5. In certain embodiments, the plasma/plasmablast cell-enriched gene is IgJ and the naïve/mature B cell-enriched gene is CD19. In certain embodiments, measuring gene expression comprises measuring mRNA. In a further embodiment, measuring mRNA comprises a PCR method or a microarray chip. In certain embodiments, the biological sample comprises whole blood. In certain embodiments, the patient is suffering from, or is suspected of suffering from, rheumatoid arthritis. In certain embodiments, the patient is suffering from, or is suspected of suffering from, multiple sclerosis, lupus, or ANCA-vasculitis. In a further embodiment, the patient is suffering from, or is suspected of suffering from, relapsing-remitting multiple sclerosis or primary progressive multiple sclerosis. In certain embodiments, the B-cell antagonist is selected from an anti-CD22 antibody, an anti-CD20 antibody, an anti-BR3 antibody, and a BR3-Fc immunoadhesin. In certain embodiments, the B-cell antagonist is an anti-CD20 antibody. In a further embodiment, the anti-CD20 antibody is selected from rituximab, ibritumomab tiuxetan, tositumomab, ocrelizumab, 1F5, 2H7, and A20. In a still further embodiment, the anti-CD20 antibody is rituximab. In yet another embodiment, the anti-CD20 antibody is ocrelizumab. In certain embodiments, the response predicted to the therapeutic agent comprising the B-cell antagonist is non-response.

In another aspect, methods of treating autoimmune diseases in patients comprising administering a therapeutically effective amount of a therapeutic agent other than a B-cell antagonist are provided. In certain embodiments, a biological sample obtained from the patient prior to treatment has been shown to possess elevated expression of at least one gene enriched in plasma/plasmablast cells compared to the expression level of the same at least one gene in a biological sample obtained from a control subject or to a threshold value for the plasma/plasmablast cell-enriched gene. In certain embodiments, the biological sample has in addition been shown to possess a low level of expression of at least one gene enriched in naïve/mature B cells compared to the expression level of the same at least one gene enriched in naïve/mature B cells in the biological sample obtained from the control subject or to a threshold value for the naïve/mature B cell-enriched gene. In certain embodiments, the plasma/plasmablast cell-enriched gene is IgJ. In certain embodiments, the naïve/mature B cell-enriched gene is FCRL5. In certain embodiments, the naïve/mature B cell-enriched gene is CD19. In certain embodiments, the plasma/plasmablast cell-enriched gene is IgJ and the naïve/mature B cell-enriched gene is FCRL5. In certain embodiments, the plasma/plasmablast cell-enriched gene is IgJ and the naïve/mature B cell-enriched gene is CD19. In certain embodiments, the biological sample comprises whole blood. In certain embodiments, the autoimmune disease is rheumatoid arthritis, multiple sclerosis, relapsing-remitting multiple sclerosis, primary progressive multiple sclerosis, lupus, or ANCA-vasculitis.

In one aspect, gene expression is measured by microarray. In another aspect gene expression is measured by polymerase chain reaction (PCR) or real-time quantitative polymerase chain reaction (qPCR). In another aspect, gene expression is measured by multiplex-PCR. According to another embodiment, expression of a gene of interest in a patient's biological sample is considered elevated when compared to that of a control subject's biological sample if the relative mRNA level of the gene of interest in the patient's sample is greater than 2 fold of the level of the control subject's mRNA. According to another embodiment, the relative mRNA level of the gene of interest in the patient's sample is greater than 3 fold, 5 fold, 10 fold, 15 fold, 20 fold, 25 fold, or 30 fold compared to the level in the control subject's sample. In another embodiment, expression of a gene of interest in a patient's biological sample is considered low when compared to that of a control subject's biological sample if the relative mRNA level of the gene of interest in the patient's sample is less than 2 fold of the level of the control subject's mRNA. According to another embodiment, expression of a gene of interest in a patient's biological sample is considered low when compared to that of a control subject's biological sample if the relative mRNA level of the gene of interest in the patient's sample is less than 3 fold, 5 fold, 10 fold, 15 fold, 20 fold, 25 fold, or 30 fold compared to the level in the control subject's sample.

In another aspect, the gene expression level is measured by a PCR method or a microarray method. In one embodiment, the microarray method comprises the use of a microarray chip having one or more nucleic acid molecules that can hybridize under stringent conditions to a nucleic acid molecule encoding a gene mentioned above. In one embodiment, the PCR method is qPCR. In one embodiment, the PCR method is multiplex-PCR.

In yet another aspect, methods of a selecting a therapeutic agent for treatment of a patient suffering from an autoimmune disease are provided. In certain embodiments, the method comprises obtaining a biological sample from the patient; measuring in the biological sample obtained from the patient the expression of at least one gene enriched in plasma/plasmablast cells; comparing the expression of the at least one gene in the patient's biological sample to the expression of the same at least one gene in a biological sample obtained from a control subject or to a threshold value for the at least one plasma/plasmablast cell-enriched gene; determining whether the expression of the at least one gene in the patient's biological sample is elevated compared to the expression in the control subject's biological sample or to the threshold value; and selecting a therapeutic agent other than a B-cell antagonist provided the the expression of the at least one gene in the patient's biological sample is elevated. In a further embodiment, the method comprises measuring in the biological sample obtained from the patient the expression of at least one gene enriched in naïve/mature B cells; comparing the expression of the at least one naïve/mature B cell-enriched gene in the patient's biological sample to the expression of the same at least one naïve/mature B cell-enriched gene in the biological sample obtained from the control subject or to a threshold value for the naïve/mature B cell-enriched gene; determining whether the expression of the at least one naïve/mature B cell-enriched gene in the patient's biological sample is low compared to the expression in the same at least one naïve/mature B cell-enriched gene in the control subject's biological sample or to the threshold value for the naïve/mature B cell-enriched gene; and selecting a therapeutic agent other than a B-cell antagonist provided the expression of the at least one naïve/mature B cell-enriched gene is low. In certain embodiments, the plasma/plasmablast cell-enriched gene is IgJ. In certain embodiments, the naïve/mature B cell-enriched gene is FCRL5. In certain embodiments, the naïve/mature B cell-enriched gene is CD19. In certain embodiments, the plasma/plasmablast cell-enriched gene is IgJ and the naïve/mature B cell-enriched gene is FCRL5. In certain embodiments, the plasma/plasmablast cell-enriched gene is IgJ and the naïve/mature B cell-enriched gene is CD19. In certain embodiments, measuring gene expression comprises measuring mRNA. In a further embodiment, measuring mRNA comprises a PCR method or a microarray chip. In certain embodiments, the biological sample comprises whole blood. In certain embodiments, the autoimmune disease is selected from rheumatoid arthritis, multiple sclerosis, relapsing-remitting multiple sclerosis, primary progressive multiple sclerosis, lupus, and ANCA-vasculitis.

BRIEF DESCRIPTION OF THE DRAWINGS

(FIG. 1A) CD19 positive B cells in blood (y axis; cells/µl) compared to CD20 mRNA expression levels (x axis); (FIG. 1B) correlation coefficients between RT-qPCR expression levels of plasmablast and mature B cell markers and various B cell subsets; the shading bar at the bottom indicates relative expression level from low (left side) to high (right side); (FIG. 1C) Pearson correlation coefficient for IgJ expression levels (RT-qPCR; y axis) compared to whole genome mRNA microarray analysis (x axis) in whole blood RNA from patients receiving rituximab at baseline, day 15 and day 84; (FIG. 1D) comparison of baseline IgJ mRNA levels in ACR50 nonresponders (left side) and responders (right side); the dotted line indicates the 0.1 expression unit threshold; individuals with IgJ levels above the 0.1 expression unit threshold are shown as open circles (ACR50 nonresponders, left side) and open squares (ACR50 responders, right side).

FIGS. 2A-2C show ACR50 response rates in patient groups from the REFLEX trial, stratified based on the baseline expression of single biomarkers CD19 (FIG. 2A), FCRL5 (FIG. 2B) and combination biomarker IgJ$^{hi}$ CD19$^{lo}$ (FIG. 2C) as described in Example 1. Hatched bars: ACR50 response rates at 6 months (day 168) for patients treated with rituximab; open bars: ACR50 response rates at 6 months (day 168) for patients that received placebo. The horizontal lines above the bars in panels FIGS. 2A-C refer to the summary statistics calculated for the ACR50 percentage difference for the active rituximab arm and placebo arm between the biomarker positive and negative subgroups. P values were calculated using the Fisher exact test. "n" refers to the number of individual patients in each subgroup. In these experiments, the threshold values were: IgJ expression ≥0.1, FCRL5 expression ≥0.02, and CD19 ≥0.05. The IgJ$^{hi}$ CD19$^{lo}$ subgroup (FIG. 2C) had IgJ expression ≥0.1 and CD19 expression ≥0.05.

(FIG. 3A) IgJ biomarker in baseline mRNA samples from the REFLEX (rituximab) trial; (FIG. 3B) IgJ biomarker in baseline mRNA samples from the DANCER (rituximab) trial; (FIG. 3C) IgJ biomarker in baseline mRNA samples from the SERENE (rituximab) trial; (FIG. 3D)) IgJ biomarker in baseline mRNA samples from the SCRIPT (ocrelizumab) trial; (FIG. 3E) Odds ratios and 95% c.i. for the enrichment of ACR50 responses in the IgJ$^{lo}$ subgroup as compared to the IgJ$^{hi}$ subgroup for the individual trials, the replication trials in aggregate (DANCER, SERENE and SCRIPT), and for all trials together.

(FIG. 4A) IgJ$^{hi}$ FCRL5$^{lo}$ biomarkers in baseline mRNA samples from the REFLEX trial; (FIG. 4B) IgJ$^{hi}$ FCRL5$^{lo}$ biomarkers in baseline mRNA samples from the DANCER trial; (FIG. 4C) IgJ$^{hi}$ FCRL5$^{lo}$ biomarkers in baseline mRNA samples from the SERENE trial; (FIG. 4D) IgJ$^{hi}$ FCRL5$^{lo}$ biomarkers in baseline mRNA samples from the SCRIPT trial. (FIG. 4E) Odds ratios and 95% C.I. for the enrichment of ACR50 responses in the IgJ$^{hi}$ FCRL5$^{lo}$ subgroup as compared to remaining patients for the individual trials, the replication trials in aggregate (DANCER, SERENE and SCRIPT), and for all trials together.

DETAILED DESCRIPTION

Figure 1A:
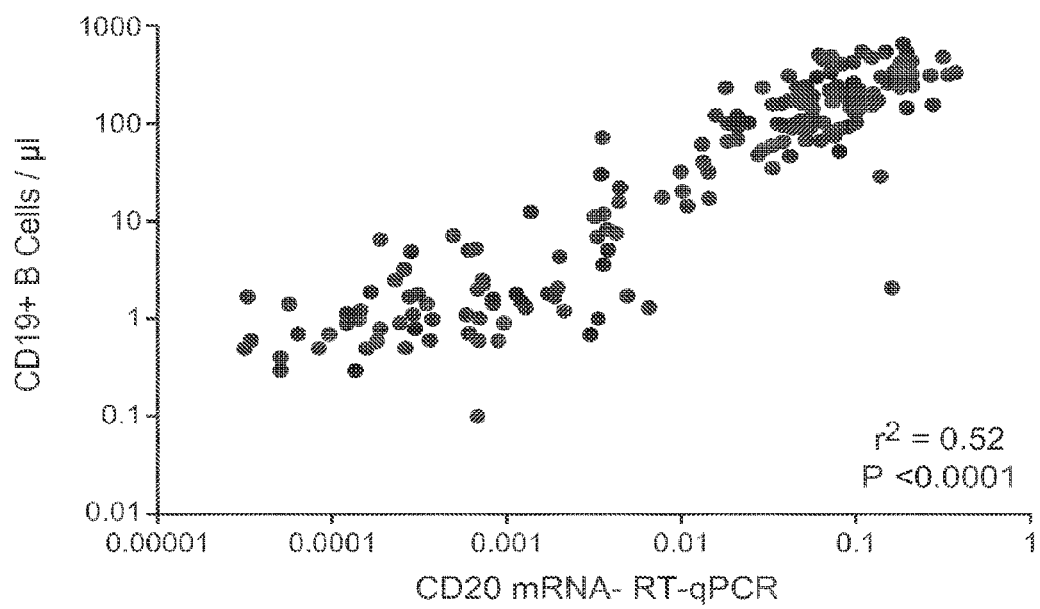
FIGS. 1A-1D show blood mRNA biomarkers for B cells and plasmablasts as described in Example 1.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Certain Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

The term "autoimmune disease" refers to a disease or disorder arising from and/or directed against an individual's own tissues or organs, or a co-segregate or manifestation thereof, or resulting condition therefrom. Typically, various clinical and laboratory markers of autoimmune diseases may exist including, but not limited to, hypergammaglobulinemia, high levels of autoantibodies, antigen-antibody complex deposits in tissues, clinical benefit from corticosteroid or immunosuppressive treatments, and lymphoid cell aggregates in affected tissues.

"Rheumatoid arthritis," (RA) refers to a chronic systemic autoimmune inflammatory disease that mainly involves the synovial membrane of multiple joints with resultant injury to the articular cartilage, resulting in joint destruction. The main presenting symptoms in RA are pain, stiffness, swelling, and/or loss of function of one or more joints.

"Multiple sclerosis" (MS) is an autoimmune demyelinating disorder. MS generally exhibits a relapsing-remitting course or a chronic progressive course.

As used herein, "relapsing-remitting MS" (RRMS) is characterized by partial or total recovery after attacks.

The term "secondary-progressive MS" (SPMS) refers to a relapsing-remitting course of MS which becomes steadily progressive. Attacks and partial recoveries may continue to occur.

The term "primary-progressive MS" (PPMS) refers to MS that is progressive from the onset. Symptoms in patients with PPMS generally do not remit—i.e., decrease in intensity.

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, refers to short, single stranded polynucleotides that are at least about seven nucleotides in length and less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single stranded polynucleotide that is capable of hybridizing to a nucleic acid and allowing the polymerization of a complementary nucleic acid, generally by providing a free 3'-OH group.

The term "array" or "microarray" refers to an ordered arrangement of hybridizable array elements, preferably polynucleotide probes (e.g., oligonucleotides), on a substrate. The substrate can be a solid substrate, such as a glass slide, or a semi-solid substrate, such as nitrocellulose membrane.

The term "amplification" refers to the process of producing one or more copies of a reference nucleic acid sequence or its complement. Amplification may be linear or exponential (e.g., PCR). A "copy" does not necessarily mean perfect sequence complementarity or identity relative to the template sequence. For example, copies can include nucleotide analogs such as deoxyinosine, intentional sequence alterations (such as sequence alterations introduced through a primer comprising a sequence that is hybridizable, but not fully complementary, to the template), and/or sequence errors that occur during amplification.

The term "detection" includes any means of detecting, including direct and indirect detection.

"Elevated expression" or "elevated levels" refers to an increased expression of a mRNA or a protein in a patient relative to a control, such as an individual or individuals who are not suffering front an autoimmune disease, e.g., RA, or relative to a pre-established threshold or cut-off value.

The term "multiplex-PCR" refers to a single PCR reaction carried out on nucleic acid obtained from a single source (e.g., a patient) using more than one primer set for the purpose of amplifying two or more DNA sequences in a single reaction.

As used herein, "rheumatoid factor," or "RF," refers to IgM, IgG, or IgA isotypes, singly or in any combination, of antibodies detected in patient serum and directed to antigenic determinants present on human and animal IgG.

The term "positive for RF" refers to a result of an assay for RF, e.g., an ELISA assay, where the result is above a threshold or cutoff value for that assay for samples that are considered to reproducibly contain detectable levels of RF.

The term "negative for RF" refers to a result of an assay for RF, e.g., an ELISA assay, where the result is at or below a threshold or cutoff value for that assay for samples that are considered to reproducibly contain undetectable levels of RF.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/ 0.1% sodium dodecyl sulfate at 50 C; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42 C, with a 10 minute wash at 42 C in 0.2×SSC (sodium chloride/ sodium citrate) followed by a 10 minute high-stringency wash consisting of 0.1×SSC containing EDTA at 55 C.

"Moderately stringent conditions" can be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50 C. The skilled artisan will recognize how to adjust the temperature, ionic strength, etc. as necessary to accommodate factors such as probe length and the like.

The term "biomarker" as used herein refers to an indicator of a phenotype of a patient, e.g, a pathological state or likely responsiveness to a therapeutic agent, which can be detected in a biological sample of the patient. Biomarkers include, but are not limited to, DNA, RNA, protein, carbohydrate, or glycolipid-based molecular markers.

The term "diagnosis" is used herein to refer to the identification or classification of a molecular or pathological state, disease or condition. For example, "diagnosis" may refer to identification of a particular type of RA. "Diagnosis" may also refer to the classification of a particular subtype of RA, e.g., by histopathological criteria (e.g., lymphoid infiltration or follicle-like lymphoid cluster), or by molecular features (e.g., a subtype characterized by expression of one or a combination of particular genes or proteins encoded by said genes).

The term "aiding diagnosis" is used herein to refer to methods that assist in making a clinical determination regarding the presence, or nature, of a particular type of symptom or condition. For example, a method of aiding diagnosis of RA can comprise measuring the expression of certain genes in a biological sample from an individual.

The term "prognosis" is used herein to refer to the prediction of the likelihood of autoimmune disorder-attributable disease symptoms of an autoimmune disease such as RA.

The term "prediction" is used herein to refer to the likelihood that a patient will respond either favorably or unfavorably to a drug (therapeutic agent) or set of drugs or a therapeutic regimen. In one embodiment, the prediction relates to the extent of those responses. In one embodiment, the prediction relates to whether and/or the probability that a patient will survive or improve following treatment, for example treatment with a particular therapeutic agent, or for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

An "individual," "subject" or "patient" is a vertebrate. In certain embodiments, the vertebrate is a mammal. Mammals include, but are not limited to, primates (including human and non-human primates) and rodents (e.g., mice and rats). In certain embodiments, a mammal is a human.

A "control subject" refers to a healthy subject who has not been diagnosed as having a particular disease, e.g., RA, and who does not suffer from any sign or symptom associated with that disease.

The term "sample," as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue" or "cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like. A "reference sample", "reference cell", "reference tissue", "control sample", "control cell", or "control tissue", as used herein, refers to a Sample, cell or tissue obtained from a source known, or believed, not to be afflicted with the disease or condition for which a method or composition of the invention is being used to identify. In one embodiment, a reference sample, reference cell, reference tissue, control sample, control cell, or control tissue is obtained from a healthy part of the body of the same subject or patient in whom a disease or condition is being identified using a composition or method of the invention. In one embodiment, a reference sample, reference cell, reference tissue, control sample, control cell, or control tissue is obtained from a healthy part of the body of an individual who is not the subject or patient in whom a disease or condition is being identified using a composition or method of the invention.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

A "medicament" is an fictive; drug to treat a disease, disorder, and/or condition.

The term "increased resistance" to a particular therapeutic agent or treatment option, when used in accordance with the invention, means decreased response to a standard dose of the drug or to a standard treatment protocol.

The term "decreased sensitivity" to a particular therapeutic agent or treatment option, when used in accordance with the invention, means decreased response to a standard dose of the agent or to a standard treatment protocol, where decreased response can be compensated for (at least partially) by increasing the dose of agent, or the intensity of treatment.

"Patient response" or "response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of autoimmune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment.

The term "gene signature" is used interchangeably with "gene expression signature" and refers to one or a combination of genes whose expression is indicative of a particular subtype or disease state characterized by certain molecular, pathological, histological, and/or clinical features. In certain embodiments, a gene expression signature is predictive of patient responsiveness to a particular therapeutic agent or treatment regimen. In certain embodiments, the expression of one or more genes comprising the gene signature is elevated compared to that in control subjects. In certain embodiments, the expression of one or more genes comprising the gene signature is decreased compared to that in control subjects. In certain embodiments, the expression of one or more genes comprising the gene signature is differentially regulated in test subjects (e.g., patients) compared to the expression of those gene(s) in control subjects.

The term "protein signature" is used interchangeably with "protein expression signature" and refers to one or a combination of proteins whose expression is indicative of a particular subtype or disease state characterized by certain molecular, pathological, histological, and/or clinical features. In certain embodiments, a protein expression signature is predictive of patient responsiveness to a particular therapeutic agent or treatment regimen. In certain embodiments, the expression of one or more proteins comprising the protein signature is elevated compared to that in control subjects. In certain embodiments, the expression of one or more proteins comprising the protein signature is decreased compared to that in control subjects. In certain embodiments, the expression of one or more proteins comprising the protein signature is differentially regulated in test subjects (e.g., patients) compared to the expression of those protein(s) in control subjects.

A "RA therapeutic agent," a "therapeutic agent effective to treat RA," and grammatical variations thereof, as used herein, refer to an agent that when provided in an effective amount is known, clinically shown, or expected by clinicians to provide a therapeutic benefit in a subject who has RA.

An "MS therapeutic agent," a "therapeutic agent effective to treat MS," and grammatical variations thereof, as used herein, refer to an agent that when provided in an effective amount is known, clinically shown, or expected by clinicians to provide a therapeutic benefit in a subject who has MS.

An "ANCA-vaculitis therapeutic agent," a "therapeutic agent effective to treat ANCA-vasculitis," and grammatical variations thereof, as used herein, refer to an agent that when provided in an effective amount is known, clinically shown, or expected by clinicians to provide a therapeutic benefit in a subject who has ANCA-vasculitis.

A "B-cell surface marker" or "B-cell surface antigen" herein is an antigen expressed on the surface of a B cell that can be targeted with an antagonist that binds thereto. Exemplary B-cell surface markers include the CD10, CD19, CD20 (MS4A1), CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85, and CD86 leukocyte surface markers (for descriptions, see The Leukocyte Antigen Facts Book, 2nd Edition. 1997, ed. Barclay et al. Academic Press, Harcourt Brace & Co., New York). Other B-cell surface markers include RP105, FcRH2, B-cell CR2, CCR6, P2X5, HLA-DOB, CXCR5, FCER2, BR3, Btig, NAG14, SLGC16270, FcRH1, IRTA2, ATWD578, FcRH3, IRTA1, FcRH6, BCMA, and 239287. The B-cell surface marker of particular interest is preferentially expressed on B cells compared to other non-B-cell tissues of a mammal and may be expressed on both precursor B cells and mature B cells.

An "antibody that binds to a B-cell surface marker" is a molecule that, upon binding to a B-cell surface marker, destroys or depletes B cells in a mammal and/or interferes with one or more B-cell functions, e.g. by reducing or preventing a Immoral response elicited by the B cell. The antibody in certain instances is able to deplete B cells (i.e. reduce circulating B-cell levels) in a mammal treated therewith. Such depletion may be achieved via various mechanisms such as antibody-dependent cell-mediated cytotoxicity (ADCC) and/or complement-dependent cytotoxicity (CDC), inhibition of B-cell proliferation, and/or induction of B-cell death (e.g. via apoptosis).

An "antagonist" refers to a molecule capable of neutralizing, blocking, inhibiting, abrogating, reducing or interfering with the activities of a particular or specified protein, including its binding to one or more receptors in the case of a ligand or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of the protein, and fusion proteins, receptor molecules and derivatives which bind specifically to the protein thereby sequestering its binding to its target, antagonist variants of the protein, antisense molecules directed to the protein, RNA aptamers, and ribozymes against the protein.

A "B-cell antagonist" is a molecule that, upon binding to a B-cell surface marker, destroys or depletes B cells in a mammal and/or interferes with one or more B-cell functions, e.g. by reducing or preventing a humoral response elicited by the B cell. The antagonist in certain instances is able to deplete B cells (i.e. reduce circulating B-cell levels) in a mammal treated therewith. Such depletion may be achieved via various mechanisms such as ADCC and/or CDC, inhibition of B-cell proliferation, and/or induction of B-cell death (e.g. via apoptosis). Exemplary antagonists include synthetic or native-sequence peptides, fusion proteins, and small-molecule antagonists that hind to the B-cell marker, optionally conjugated with or fused to a cytotoxic agent. Examples include but are not limited to, e.g., CD22 antibodies, CD20 antibodies, BR3 antibodies (e.g., WO0224909), and BR3-Fc immunoadhesin.

Examples of CD20 antibodies include: "C2B8," which is now called "rituximab" ("RITUXAN®") (U.S. Pat. No. 5,736,137); the yttrium-[90]-labeled 2B8 murine antibody designated "Y2B8" or "ibritumomab tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "tositumomab," optionally labeled with $^{131}$I to generate the "$^{131}$I-B1" or "iodine I$^{131}$ tositumomab" antibody (BEXXAR™) commercially available from Corixa (see, also, U.S. Pat. No. 5,595,721); murine monoclonal antibody "1F5" (Press et al. Blood 69(2):584-591 (1987) and variants thereof including "framework-patched" or humanized 1F5 (WO 2003/002607, Leung, S.; ATCC deposit HB-96450); murine 2H7 and chimeric 2H7 antibody (U.S. Pat. No. 5,677,180); humanized 2H7 (see, e.g., WO04/056312; US20060024295); HUMAX-CD20™ antibodies (Genmab, Denmark); the human monoclonal antibodies set forth in WO 2004/035607 (Teeling et al.); AME-133™ antibodies (Applied Molecular Evolution); A20 antibody or variants thereof such as chimeric or humanized A20 antibody (cA20, hA20, respectively) (US 2003/0219433, Immunomedics); and monoclonal antibodies L27, G28-2, 93-1 B3, B-C1 or NU-B2 available from the International Leukocyte Typing Workshop (Valentine et al., In: Leukocyte Typing III (McMichael, Ed., p. 440, Oxford University Press (1987)).

The terms "BAFF," "BAFF polypeptide," "TALL-1" or "TALL-1 polypeptide," "BLyS", and "THANK" when used herein encompass "native-sequence BAFF polypeptides" and "BAFF variants." "BAFF" is a designation given to those polypeptides that have the human BAFF sequence as set forth in, for example, U.S. Pat. Pub. No. 2006/0110387, and homologs and fragments and variants thereof, which have the biological activity of the native-sequence BAFF. A biological activity of BAFF can be selected from the group consisting of promoting B-cell survival, promoting B-cell maturation, and binding to BR3. The term "BAFF" includes those polypeptides described in Shu et al., J. Leukocyte Biol., 65:680 (1999); GenBank Accession No. AF136293; WO 1998/18921; EP 869,180; WO 1998/27114; WO 1999/12964; WO 1999/33980; Moore et al., Science, 285:260-263 (1999); Schneider et al., J. Exp. Med., 189:1747-1756 (1999); and Mukhopadhyay et al., J. Biol. Chem., 274: 15978-15981 (1999).

The term "BAFF antagonist" as used herein is used in the broadest sense, and includes any molecule that (1) binds a native-sequence BAFF polypeptide or binds a native-sequence BR3 polypeptide to block, partially or fully, BR3 interaction with BAFF polypeptide, and (2) partially or fully blocks, inhibits, or neutralizes native-sequence BAFF signaling. Native-sequence BAFF polypeptide signaling promotes, among other things, B-cell survival and B-cell maturation. The inhibition, blockage, or neutralization of BAFF signaling results in, inter alia, a reduction in the number of B cells. A BAFF antagonist as defined herein will partially or fully block, inhibit, or neutralize one or more biological activities of a BAFF polypeptide, in vitro or in vivo. In one embodiment, a biologically active BAFF potentiates any one or a combination of the following events in vitro or in vivo: an increased survival of B cells, an increased level of IgG and/or IgM, an increased numbers of plasma cells, and processing of NF-κb2/100 to p52 NF-κβ splenic B cells (e.g., Batten et al., J. Exp. Med. 192:1453-1465 (2000); Moore et al., Science 285:260-263 (1999); and Kayagaki et al., Immunity, 10:515-524 (2002)).

In some embodiments, a BAFF antagonist as defined herein includes anti-BAFF antibodies, BAFF-binding polypeptides (including immunoadhesins and peptides), and BAFF-binding small molecules. BAFF antagonists include, for example, the BAFF-binding antibodies described in WO 2002/02641 (e.g., antibodies comprising the amino acid sequence of any of SEQ ID NOS:1-46, 321-329, 834-872, 1563-1595, 1881-1905 of Table 1 thereof). In a further embodiment, the immunoadhesin comprises a BAFF-binding region of a BAFF receptor (e.g., an extracellular domain of BR3, BCMA, or TACI). In a still further embodiment, the immunoadhesin is BR3-Fc. Other examples of BAFF-binding Fc proteins can be found in WO 2002/66516, WO 2000/40716, WO 2001/87979, WO 2003/024991, WO 2002/16412, WO 2002/38766, WO 2002/092620, and WO 2001/12812. Methods of making BAFF antagonists are described, for example, in US 2005/0095243 and US 2005/0163775.

The terms "BR3", "BR3 polypeptide" or "BR3 receptor" when used herein encompass native-sequence BR3 polypeptides and BR3 variants, as defined hereinbelow. "BR3" is a designation given to those polypeptides comprising, for example, the human BR3 sequence set forth in WO 2003/14294 and US 2005/0070689. BR3 polypeptides can be isolated from a variety of sources, such as from human tissue types or from another source, or prepared by recombinant and/or synthetic methods. The term BR3 includes the BR3 polypeptides described in WO 2002/24909, WO 2003/14294, and US 2005/0070689. Anti-BR3 antibodies can be prepared in accordance with methods set for in, for example, WO 2003/14294 and US 2005/0070689.

A "native-sequence" BR3 polypeptide or "native BR3" comprises a polypeptide having the same amino acid sequence as the corresponding BR3 polypeptide derived from nature. Such native-sequence BR3 polypeptides can be isolated from nature or can be produced by recombinant and/or synthetic means. The term "native-sequence BR3 polypeptide" specifically encompasses naturally occurring truncated, soluble or secreted forms (e.g., an extracellular domain sequence), naturally occurring variant forms (e.g., alternatively spliced forms) and naturally occurring allelic variants of the polypeptide. The BR3 polypeptides of the invention include the BR3 polypeptide comprising or consisting of the contiguous sequence of amino acid residues 1 to 184 of a human BR3 (see WO 2003/14294 and US 2005/0070689).

A BR3 "extracellular domain" or "ECD" refers to a form of the BR3 polypeptide that is essentially free of the transmembrane and cytoplasmic domains. ECD forms of BR3 include a polypeptide comprising any one of the amino acid sequences selected from the group consisting of amino acids 1-77, 2-62, 2-71, 1-61, 7-71, 23-38 and 2-63 of human BR3. In certain embodiments, BAFF antagonists are polypeptides comprising any one of the above-mentioned ECD forms of human BR3 and variants and fragments thereof that bind a native BAFF.

"BR3 variant" means a BR3 polypeptide having at least about 80% amino acid sequence identity with the amino acid sequence of a native-sequence, full-length BR3 or BR3 ECD and binds a native-sequence BAFF polypeptide. Optionally, the BR3 variant includes a single cysteine-rich domain. Such BR3 variant polypeptides include, for instance, BR3 polypeptides wherein one or more amino acid residues are added, or deleted, at the N- and/or C-terminus, as well as within one or more internal domains, of the full-length amino acid sequence. Fragments of the BR3 ECD that bind a native sequence BAFF polypeptide are also contemplated.

The term "APRIL antagonist" as used herein is used in the broadest sense, and includes any molecule that (1) binds a native-sequence APRIL polypeptide or binds a native-sequence ligand to APRIL to block, partially or fully, the ligand's interaction with APRIL polypeptide, and (2) partially or fully blocks, inhibits, or neutralizes native-sequence APRIL signaling. Native-sequence APRIL polypeptide signaling promotes, among other things, B-cell survival and B-cell maturation. APRIL (a proliferation-inducing ligand) is a TNF family member with a shared receptor to BAFF. Examples of APRIL antagonists include but are not limited to atacicept (same as TACI-Ig immunoadhesin and a BAFF/APRIL antagonist (soluble BCMA-Fc).

The term "cytokine" is a generic term for proteins released by one cell population that act on another cell as intercellular mediators. Examples of such cytokines are lymphokines, monokines; interleukins (ILs) such as IL-1, IL-1a, IL-2, IL-3, IL-4, IL-5, IL-6, IL-7, IL-8, IL-9, IL-11, IL-12, IL-15, IL-17A, IL-17F, IL-17A/F; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native-sequence cytokines, including synthetically produced small-molecule entities and pharmaceutically acceptable derivatives and salts thereof.

As used herein, "tumor necrosis factor-alpha (TNF-alpha)" refers to a human TNF-alpha molecule comprising the amino acid sequence as described in Pennica et al., Nature, 312:721 (1984) or Aggarwal et al., JBC, 260:2345 (1985).

A "TNF-alpha inhibitor" herein is an agent that inhibits, to some extent, a biological function of TNF-alpha, generally through binding to TNF-alpha and neutralizing its activity. Examples of TNF-alpha inhibitors specifically contemplated herein are etanercept (ENBREL®), infliximab (REMICADE®), adalimumab (HUMIRA®), golimumab (SIMPONI™), and certolizumab pegol (CIMZIA®).

Examples of "disease-modifying anti-rheumatic drugs" or "DMARDs" include hydroxycloroquine, sulfasalazine, methotrexate (plus oral and subcutaneous methrotrexate), leflunomide, azathioprine, D-penicillamine, Gold (oral), Gold (intramuscular), minocycline, cyclosporine, *Staphylococcal* protein A immunoadsorption, including salts and derivatives thereof, etc.

"CTLA4" is expressed on activated T lymphocytes and is involved in down-regulation of the immune response. Other names for CTLA4 in the literature include cytotoxic T-lymphocyte-associated antigen 4, cytotoxic T-lymphocyte-associated protein 4, cell differentiation antigen CD152, and cytotoxic T-lymphocyte-associated granule serine protease 4.

A therapeutic agent that has "marketing approval," or that has been "approved as a therapeutic agent," or grammatical variations thereof of these phrases, as used herein, refer to an agent (e.g., in the form of a drug formulation, medicament) that is approved, licensed, registered or authorized by a relevant governmental entity (e.g., federal, state or local regulatory agency, department, bureau) to be sold by and/or through and/or on behalf of a commercial entity (e.g., a for-profit entity) for the treatment of a particular disorder (e.g., RA) or a patient subpopulation (e.g., patients of a particular ethnicity, gender, lifestyle, disease risk profile, etc.). A relevant governmental entity includes, for example, the Food and Drug Administration (FDA), European Medicines Agency (EMA), and equivalents thereof.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is a minimum antibody fragment which contains a complete antigen-binding site. In one embodiment, a two-chain Fv species consists of a dimer of one heavy- and one light-chain variable domain in tight, non-covalent association. Collectively, the six CDRs of an Fv confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature,* 256: 495 (1975); Harlow et al., *Antibodies: A Laboratory Manual,* (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633, 425; 5,661,016; Marks et al., *Bio. Technology* 10: 779-783 (1992); Lonberg et al., *Nature* 368: 856-859 (1994); Morrison, *Nature* 368:812-813 (1994); Fishwild et al., *Nature Biotechnol.* 14: 845-851 (1996); Neuberger, *Nature Biotechnol.* 14: 826 (1996) and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6855-9855 (1984)).

"Humanized" forms of non-human (e.g., murine) antibodies are chimeric antibodies that contain minimal sequence derived from non-human immunoglobulin, in one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al., *J. Mol. Biol.,* 222: 581-597 (1991) and Hoogenboom et al., *Nucl. Acids Res.,* 19: 4133-4137 (1991)); using human myeloma and mouse-human heteromyeloma cell lines for the production of human monoclonal antibodies (see, e.g., Kozbor *J. Immunol.*, 133: 3001 (1984); Brodeur et al., *Monoclonal Antibody Production Techniques and Applications*, pp. 55-93 (Marcel Dekker, Inc., New York, 1987); and Boerner et al., *J. Immunol.*, 147: 86 (1991)); and generating monoclonal antibodies in transgenic animals (e.g., mice) that are capable of producing a full repertoire of human antibodies in the absence of endogenous immunoglobulin production (see, e.g., Jakobovits et al., *Proc. Natl. Acad. Sci USA*, 90: 2551 (1993); Jakobovits et al., *Nature*, 362: 255 (1993); Bruggermann et al., *Year in Immunol.*, 7: 33 (1993)). This definition of a human antibody specifically excludes a humanized antibody comprising antigen-binding residues from a non-human animal.

An "affinity matured" antibody is one with one or more alterations in one or more CDRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of HVR and/or framework residues is described by: Barbas et al. *Proc Nat. Acad. Sci. USA* 91:3809-3813 (1994); Schier et al. *Gene* 169:147-155 (1995): Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking antibody" or an "antagonist antibody" is one which inhibits or reduces a biological activity of the antigen it binds. Certain blocking antibodies or antagonist antibodies partially or completely inhibit the biological activity of the antigen.

As used herein, "growth-inhibitory" antibodies are those that prevent or reduce proliferation of a cell expressing an antigen to which the antibody binds. For example, the antibody may prevent or reduce proliferation of B cells in vitro and/or in vivo.

Antibodies that "induce apoptosis" refer to antibodies that induce programmed cell death, e.g. of B cell, as determined by standard apoptosis assays, such as binding of annexin V, fragmentation of DNA, cell shrinkage, dilation of endoplasmic reticulum, fragmentation, and/or formation of membrane vesicles (called apoptotic bodies).

Antibody "effector functions" refer to those biological activities attributable to the Fc region (a native-sequence Fc region or amino-acid-sequence-variant Fc region) of an antibody, and vary with the antibody isotype. Examples of antibody effector functions include but are not limited to: C1q binding and complement-dependent cytotoxicity (CDC); Fc-receptor binding; antibody-dependent cell-mediated cytotoxicity (ADCC); phagocytosis; down-regulation of cell-surface receptors (e.g. B-cell receptor); and B-cell activation.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is typically defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise herein, the numbering of the residues in an immunoglobulin heavy chain is that of the EU index as in Kabat (Kabat et al., *Sequences of Proteins of Immunological Interest*, Ed. 5 (Public Health Service, National Institutes of Health, Bethesda, Md., 1991)). The "EU index as in Kabat" refers to the residue numbering of the human IgG1 EU antibody.

A "functional Fc region" possesses an "effector function" of a native-sequence Fc region. Exemplary "effector functions" include but are not limited to C1q binding; CDC; Fc-receptor binding; ADCC; phagocytosis; down-regulation of cell-surface receptors (e.g. B-cell receptor; BCR), etc. Such effector functions generally require the Fc region to be combined with a binding domain (e.g. an antibody-variable domain) and can be assessed using various assays as disclosed, for example, herein.

A "native-sequence Fc region" comprises an amino acid sequence identical to the amino acid sequence of an Fc region found in nature. Native-sequence human Fc regions include a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence which differs from that of a native-sequence Fc region by virtue of at least one amino acid modification, typically one or more amino acid substitution(s).

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering the nucleic acid encoding the antibody. Accordingly, a composition comprising an antibody having an Fc region can comprise an antibody with K447, with all K447 removed, or a mixture of antibodies with and without the K447 residue.

"Fc receptor" or "FcR" describes a receptor that binds to the Fc region of an antibody. In some embodiments, an FcR is a native-human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward, *Immunology Today*, 18 (12):592-8 (1997); Ghetie et al., *Nature Biotechnology*, 15 (7):637-40 (1997); Hinton et al., *J. Biol. Chem.*, 279(8):6213-6 (2004); WO 2004/92219 (Hinton et al.).

Binding to human FcRn in vivo and serum hall-life of human FcRn high-affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See, also, for example, Shields et al., *J. Biol. Chem.*, 9(2): 6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural-killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g., NK cells, neutrophils, and macrophages) enables these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol.*, 9:457-492 (1991). To assess ADCC activity of a molecule of interest, an in vitro ADCC assay, such as that described in U.S. Pat. No. 5,500,362 or U.S. Pat. No. 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al., *Proc. Natl. Acad. Sci.* (*USA*), 95:652-656 (1998).

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g. as described in Gazzano-Santoro et al., *J. Immunol. Methods*, 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 and WO 1999/51642. See, also, e.g., Idusogie et al., *J. Immunol.* 164:4178-4184 (2000).

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The word "label" when used herein refers to a detectable compound or composition. The label is typically conjugated or fused directly or indirectly to a reagent, such as a nucleic acid probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

An "isolated" biological molecule, such as a nucleic acid, polypeptide, or antibody, is one which has been identified and separated and/or recovered from at least one component of its natural environment.

Reference to "about" a value or parameter herein includes (and describes) embodiments that are directed to that value or parameter per se. For example, description referring to "about X" includes description of "X."

The term "pharmaceutical formulation" refers to a sterile preparation that is in such form as to permit the biological activity of the medicament to be effective, and which contains no additional components that are unacceptably toxic to a subject to which the formulation would be administered.

A "sterile" formulation is aseptic or free from all living microorganisms and their spores.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments and the like.

A "kit" is any manufacture (e.g a package or container) comprising at least one reagent, e.g., a medicament for treatment of RA or joint damage, or a probe for specifically detecting a biomarker gene or protein of the invention. In certain embodiments, the manufacture is promoted, distributed, or sold as a unit for performing the methods of the present invention.

A "target audience" is a group of people or an institution to whom or to which a particular medicament is being promoted or intended to be promoted, as by marketing or advertising, especially for particular uses, treatments, or indications, such as individual patients, patient populations, readers of newspapers, medical literature, and magazines, television or internet viewers, radio or internet listeners, physicians, drug companies, etc.

The term "serum sample" refers to any serum sample obtained from an individual. Methods for obtaining sera from mammals are well known in the art.

The term "whole blood" refers to any whole blood sample obtained from an individual. Typically, whole blood contains all of the blood components, e.g., cellular components and plasma. Methods for obtaining whole blood from mammals are well known in the art.

The expression "not responsive to," "non-response" and grammatical variants thereof, as it relates to the reaction of subjects or patients to one or more of the medicaments (therapeutic agents) that were previously administered to them, describes those subjects or patients who, upon administration of such medicament(s), did not exhibit any or adequate signs of treatment of the disorder for which they were being treated, or they exhibited a clinically unacceptably high degree of toxicity to the medicament(s), or they did not maintain the signs of treatment after first being administered such medicament(s), with the word treatment being used in this context as defined herein. The phrase "not responsive" includes a description of those subjects who are resistant and/or refractory to the previously administered medication(s), and includes the situations in which a subject or patient has progressed while receiving the medicament(s) that he or she is being given, and in which a subject or patient has progressed within 12 months (for example, within six months) after completing a regimen involving the medicament(s) to which he or she is no longer responsive. The non-responsiveness to one or more medicaments thus includes subjects who continue to have active disease following previous or current treatment therewith. For instance, a patient may have active disease activity after about one to three months, or three to six months, or six to 12 months, of therapy with the medicament(s) to which they are non-responsive. Such responsiveness may be assessed by a clinician skilled in treating the disorder in question.

For purposes of non-response to medicament(s), a subject who experiences "a clinically unacceptably high level of toxicity" from previous or current treatment with one or more medicaments experiences one or more negative side-effects or adverse events associated therewith that are considered by an experienced clinician to be significant, such as, for example, serious infections, congestive heart failure, demyelination (leading to multiple sclerosis), significant hypersensitivity, neuropathological events, high degrees of autoimmunity, a cancer such as endometrial cancer, non-Hodgkin's lymphoma, breast cancer, prostate cancer, lung cancer, ovarian cancer, or melanoma, tuberculosis (TB), and the like.

The "amount" or "level" of a biomarker associated with an increased clinical benefit to a patient suffering from a certain disease or disorder, or predictive of response to a particular therapeutic agent or treatment regimen, is a detectable level in a biological sample. These can be measured by methods known to one skilled in the art and also disclosed herein. The expression level or amount of biomarker assessed can be used to determine the response or the predicted response to a treatment or therapeutic agent.

The terms "level of expression" or "expression level" in general are used interchangeably and generally refer to the amount of a polynucleotide or an amino acid product or protein in a biological sample. "Expression" generally refers to the process by which gene-encoded information is converted into the structures present and operating in the cell. Therefore, as used herein, "expression" of a gene may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. "Expressed genes" include those that are transcribed into a polynucleotide mRNA and then translated into a protein, and also those that are transcribed into RNA but not translated into a protein (for example, transfer and ribosomal RNAs).

Autoimmune Diseases

Autoimmune diseases remain clinically important diseases in humans. As the name implies, autoimmune diseases act through the body's own immune system. While the pathological mechanisms differ among individual types of autoimmune diseases, one general mechanism involves the generation of antibodies (referred to herein as self-reactive antibodies or autoantibodies) directed against specific endogenous proteins. Physicians and scientists have identified more than 70 clinically distinct autoimmune diseases, including RA, multiple sclerosis (MS), vasculitis, immune-mediated diabetes, and lupus such as systemic lupus erythematosus (SLE). While many autoimmune diseases are rare—affecting fewer than 200,000 individuals—collectively, these diseases afflict millions of Americans, an estimated five percent of the population, with women disproportionately affected by most diseases. The chronic nature of these diseases leads to an immense social and financial burden.

Inflammatory arthritis is a prominent clinical manifestation in diverse autoimmune disorders including RA, psoriatic arthritis (PsA), SLE, Sjögren's syndrome, and polymyositis. Most of these patients develop joint deformities on physical examination but typically only RA and PsA patients manifest bone erosions on imaging studies.

Rheumatoid Arthritis

RA is a chronic inflammatory disease that affects approximately 0.5 to 1% of the adult population in northern Europe and North America, and a slightly lower proportion in other parts of the world. Alamanos and Drosos, *Autoimmun. Rev.*, 4: 130-136 (2005). It is a systemic inflammatory disease characterized by chronic inflammation in the synovial membrane of affected joints, which ultimately leads to loss of daily function due to chronic pain and fatigue. The majority of patients also experience progressive deterioration of cartilage and bone in the affected joints, which may eventually lead to permanent disability. The long-term prognosis of RA is poor, with approximately 50% of patients experiencing significant functional disability within 10 years from the time of diagnosis. Keystone, *Rheumatology*, 44 (Suppl. 2): ii8-ii12 (2005). Life expectancy is reduced by an average of 3-10 years. Alamanos and Drosos, supra. Patients with a high titer of rheumatoid factor (RF) (approximately 80% of patients) have more aggressive disease (Bukhari et al., *Arthritis Rheum.*, 46: 906-912 (2002)), with a worse longterm outcome and increased mortality over those who are RF negative. Heliovaara et al., *Ann. Rheum. Dis.*, 54: 811-814 (1995)).

The pathogenesis of chronic inflammatory bone diseases, such as RA, is not fully elucidated. Such diseases are accompanied by bone loss around affected joints due to increased osteoclastic resorption. This process is mediated largely by increased local production of pro-inflammatory cytokines. Teitelbaum, *Science*, 289:1504-1508 (2000); Goldring and Gravallese, *Arthritis Res.*, 2(1):33-37 (2000). These cytokines can act directly on cells in the osteoclast lineage or indirectly by affecting the production of the essential osteoclast differentiation factor, receptor activator of NFγB ligand (RANKL), and/or its soluble decoy receptor, osteoprotegerin (OPG), by osteoblast/stromal cells. Hossbauer et al., *J. Bone Min. Res.*, 15(1):2-12 (2000). Tumor necrosis factor-alpha (TNF-β) is a major mediator of inflammation. Its importance in the pathogenesis of various forms of bone loss is supported by several lines of experimental and clinical evidence. Feldmann et al., *Cell*, 85(3):307-310 (1996). However, TNF-α is not essential for osteoclastogenesis (Douni et al., *J. Inflamm.*, 47:27-38 (1996)), erosive arthritis (Campbell et al., *J. Clin. Invest.*, 107(12):1519-1527 (2001)), or osteolysis (Childs et al., *J. Bon. Min. Res.*, 16:338-347 (2001)), as these can occur in the absence of TNF-α.

In RA specifically, an immune response is thought to be initiated/perpetuated by one or several antigens presenting in the synovial compartment, producing an influx of acute inflammatory cells and lymphocytes into the joint. Successive waves of inflammation lead to the formation of an invasive and erosive tissue called pannus. This contains proliferating fibroblast-like synoviocytes and macrophages that produce proinflammatory cytokines such as TNF-α and interleukin-1 (IL-1). Local release of proteolytic enzymes, various inflammatory mediators, and osteoclast activation contributes to much of the tissue damage. There is loss of articular cartilage and the formation of bony erosions. Surrounding tendons and bursa may become affected by the inflammatory process. Ultimately, the integrity of the joint structure is compromised, producing disability.

The precise contributions of B cells to the immunopathogenesis of RA are not completely characterized. However, there are several possible mechanisms by which B cells may participate in the disease process. Silverman and Carson, *Arthritis Res. Ther.*, 5 Suppl. 4: S1-6 (2003).

Historically, B cells were thought to contribute to the disease process in RA predominantly by serving as the precursors of autoantibody-producing cells. A number of autoantibody specificities have been identified including antibodies to Type II collagen, and proteoglycans, as well as RFs. The generation of large quantities of antibody leads to immune complex formation and the activation of the complement cascade. This in turn amplifies the immune response and may culminate in local cell lysis. Increased RF synthesis and complement consumption has been correlated with disease activity. The presence of RF itself is associated with a more severe form of RA and the presence of extra-articular features.

Evidence exists (Janeway and Katz, *J. Immunol.*, 38:1051 (1998); Rivera et al., *Int. Immunol.*, 13: 1583-1593 (2001)) showing that B cells are highly efficient antigen-presenting cells (APC). RF-positive B cells may be particularly potent APCs, since their surface immunoglobulin would readily allow capture of any immune complexes regardless of the antigens present within them. Many antigens may thus be processed for presentation to T cells. In addition, it has been recently suggested that this may also allow RF-positive B cells to self-perpetuate. Edwards et al., *Immunology*, 97: 188-196 (1999).

For activation of T cells, two signals need to be delivered to the cell; one via the T-cell receptor (TCR), which recognizes the processed peptide in the presence of major histocompatibility complex (MHC) antigen, and a second, via co-stimulatory molecules. When activated, B cells express co-stimulatory molecules on their surface and can thus provide the second signal for T-cell activation and the generation of effector cells.

B cells may promote their own function as well as that of other cells by producing cytokines. Harris et al., *Nat. Immunol.*, 1: 475-482 (2000). TNF-α, IL-1, lymphotoxin-α, IL-6, and IL-10 are amongst some of the cytokines that B cells may produce in the RA synovium.

Although T-cell activation is considered to be a key component in the pathogenesis of RA, recent work using human synovium explants in severe combined immunodeficiency disorders (SCID) mice has demonstrated that T-cell activation and retention within the joint is critically dependent on the presence of B cells. Takemura et al., *J. Immunol.*, 167: 4710-4718 (2001). The precise role of B cells in this is unclear, since other APCs did not appear to have the same effect on T cells.

Structural damage to joints is an important consequence of chronic synovial inflammation. Between 60% and 95% of patients with RA develop at least one radiographic erosion within 3-8 years of disease onset. Paulus et al., *J. Rheumatol.*, 23: 801-805 (1996); Hulsmans et al., *Arthritis Rheum.*, 43: 1927-1940 (2000). In early RA, the correlation between radiographic damage scores and functional capacity is weak, but after 8 years of disease, correlation coefficients can reach as high as 0.68. Scott et al., *Rheumatology*, 39:122-132 (2000). In 1,007 patients younger than age 60 years who had RA for at least four years, Wolfe et al. (*Arthritis Rheum*, 43 Suppl. 9:S403 (2000)) found a significant association among the rate of progression of the Larsen radiographic damage score (Larsen et al., *Acta Radiol. Diagn.* 18:481-491 (1977)), increasing Social Security disability status, and decreasing family income.

Diagnosis of RA may be according to current American College of Rheumatology (ACR) criteria and may include include morning stiffness in and around the joints lasting for at least 1 hour before maximal improvement; arthritis of three or more joint areas: at least three joint areas have simultaneously had soft tissue swelling or fluid (not bony overgrowth alone) observed by a physician; the 14 possible joint areas (right and left) are proximal interphalangeal (PIP), metacarpophalangeal (MCP), wrist, elbow, knee, ankle, and metatarsophalangeal (MTP) joints; arthritis of hand joints: at least one joint area swollen as above in wrist, MCP, or PIP joint; symmetric arthritis: simultaneous involvement of the same joint areas (as in arthritis of three or more joint areas, above) on both sides of the body (bilateral involvement of PIP, MCP, or MTP joints is acceptable without absolute symmetry); rheumatoid nodules: subcutaneous nodules over bony prominences or extensor surfaces or in juxta-articular regions that are observed by a physician; serum rheumatoid factor: demonstration of abnormal amounts of serum rheumatoid factor by any method that has been positive in fewer than five percent of normal control patients; radiographic changes: radiographic changes typical of rheumatoid arthritis on posteroanterior hand and wrist X-rays, which must include erosions or unequivocal bony decalcification localized to or most marked adjacent to the involved joints (osteoarthritis changes alone do not qualify). Diagnosis of RA is typically made if a patient satisfies at least four of the above criteria.

In certain instances, a diagnosis of RA is made if a patient has a particular Disease Activity Score (DAS) (see, e.g., Van der Heijde D. M. et al., J Rheumatol, 1993, 20(3); 579-81; Prevoo M. L. et al, Arthritis Rheum, 1995, 38: 44-8). The DAS system represents both current state of disease activity and change. The DAS scoring system uses a weighted mathematical formula, derived from clinical trials in RA. For example, the DAS 28 is 0.56(T28)+0.28(SW28)+0.70 (Ln ESR)+0.014 GH wherein T represents tender joint number, SW is swollen joint number, ESR is erythrocyte sedimentation rate, and GH is global health. Various values of the DAS represent high or low disease activity as well as remission, and the change and endpoint score result in a categorization of the patient by degree of response (none, moderate, good).

A number of therapeutic agents, including biological agents, are available for the treatment of RA. Furst et al., *Ann. Rheum. Dis.* 67:2-25 (2008). Prevention or retardation of radiographic damage is one of the goals of RA treatment. Edmonds et al., *Arthritis Rheum.*, 36:336-340 (1993). Controlled clinical trials of 6 or 12 months' duration have documented that the progression of radiographic damage scores was more rapid in the placebo group than in groups that received methotrexate (MTX) (Sharp et al., *Arthritis Rheum.*, 43: 495-505 (2000)), leflunomide (Sharp et al., supra), sulfasalazine (SSZ) (Sharp et al., supra), prednisolone (Kirwan et al., *N. Engl. J. Med.*, 333:142-146 (1995); Wassenburg et al., *Arthritis Rheum*, 42: Suppl 9:S243 (1999)), interleukin-1 receptor antagonist (Bresnihan et al., *Arthritis Rheum*, 41: 2196-2204 (1998)), or an infliximab/MTX combination. Lipsky et al., *N. Eng. J. Med.*, 343: 1594-1604 (2000). Clinical trials have also documented that radiographic progression following treatment with etanercept was less rapid than that following treatment with MTX. Bathon et al., *N. Engl. J. Med.*, 343:1586-1593 (2000). Other studies have evaluated radiographic progression in patients treated with corticosteroids (Joint Committee of the Medical Research Council and Nuffield Foundation, *Ann Rheum. Dis.*, 19:331-337 (1960); Van Everdingen et al., *Ann. Intern. Med.*, 136:1-12 (2002)), cyclosporin A (Pasero et al., *J. Rheumatol.*, 24:2113-2118 (1997); Forre, *Arthritis Rheum.*, 37:1506-1512 (1994)), MTX versus azathioprine (Jeurissen et al., *Ann. Intern. Med.*, 114:999-1004 (1991)), MTX versus auranofin (Weinblatt et al., *Arthritis Rheum.*, 36:613-619 (1993)), MTX (meta-analysis) (Alarcon et al., *J. Rheumatol.*, 19:1868-1873 (1992)), hydroxychloroquine (HCQ) versus SSZ (Van der Heijde et al., *Lancet*, 1:1036-1038), SSZ (Hannonen et al., *Arthritis Rheum.*, 36:1501-1509 (1993)), the COBRA (Combinatietherapei Bij Reumatoide Artritis) combination of prednisolone, MTX, and SSZ (Boers et al., *Lancet*, 350:309-318 (1997); Landewe et al., *Arthritis Rheum.*, 46: 347-356 (2002)), combinations of MTX, SSZ, and HCQ (O'Dell et al., *N. Engl. J. Med.*, 334:1287-1291 (1996); Mottonen et al., *Lancet*, 353:1568-1573 (1999)), the combination of cyclophosphamide, azathioprine, and HCQ (Csuka et al., *JAMA*, 255:2115-2119 (1986)), and the combination of adalimumab with MTX. Keystone et al., *Arthritis Rheum.*, 46 Suppl. 9:S205 (2002).

The FDA has now approved labeling claims that certain medications, e.g., leflunomide, etanercept, and infliximab, slow the progression of radiographic joint damage. These claims are based on the statistically significant differences in progression rates observed between randomly assigned treatment groups and control groups. However, the progression rates in individuals within the treatment and control groups overlap to a considerable extent. Therefore, despite significant differences between treatment groups, these data cannot be used to estimate the probability that a patient who is starting a treatment will have a favorable outcome with respect to progression of radiographic damage. Various methods have been suggested to categorize paired radiographs from individual patients as not progressive, e.g., damage scores of 0 at both time points, no increase in damage scores, no new joints with erosions, and a change in score not exceeding the smallest detectable difference (i.e., 95% confidence interval for the difference between repeated readings of the same radiograph). Lassere et al., *J. Rheumatol.*, 26: 731-739 (1999).

Determining whether there has been increased structural damage in an individual patient during the interval between paired radiographs obtained at the beginning and end of a 6- or 12-month clinical trial has been difficult, for several reasons. The rate of radiographic damage is not uniform within a population of RA patients; a few patients may have rapidly progressing damage, but many may have little or no progression, especially if the be interval is relatively short. The methods for scoring radiographic damage, e.g., Sharp (Sharp et al., *Arthritis Rheum.*, 14: 706-720 (1971); Sharp et al., *Arthritis Rheum.*, 28: 1326-1335 (1985)), Larsen (Larsen et al., *Acta Radiol. Diagn.*, 18: 481-491 (1977)), and modifications of these methods (Van der Heijde, *J. Rheumatol.*, 27: 261-263 (2000)), depend on the judgment and the interpretation of the reader as to what is real. Factors to determine are whether an apparent interruption of the subchondral cortical plate is real, or whether a decrease in the distance between the cortices on opposite sides of a joint is real, or is due to a slight change in the position of the joint relative to the film and the radiographic beam, to a change in radiographic exposure, or to some other technical factor.

Therefore, the recorded score is an approximation of the true damage, and for many subjects, the smallest detectable difference between repeat scores of the same radiographs is larger than the actual change that has occurred during the interval between the baseline and final radiographs. If the reader is blinded to the temporal sequence of the films, these unavoidable scoring errors may be in either direction, leading to apparent "healing" when the score decreases or to apparent rapid progression when reading error increases the difference between films. When the study involves a sufficiently large population of patients who have been randomly assigned to receive an effective treatment as compared with placebo, the positive and negative reading errors offset each other, and small but real differences between treatment groups can be detected.

The imprecision of the clinical measures that are used to quantitate RA disease activity has caused a similar problem. Statistically significant differences between certain outcome measures from clinical trials were not useful for estimating the probability of improvement for an individual who was starting the treatment. Paulus et al., *Arthritis Rheum.*, 33:477-484 (1990). Attribution of individual improvement became practical with the creation of the American College of Rheumatology (ACR) 20% composite criteria for improvement (ACR20), which designated a patient as improved if there was 20% improvement in the tender and swollen joint counts and 20% improvement in at least three of five additional measures (pain, physical function, patient global health assessment, physician global health assessment, and acute-phase reactant levels). Felson et al., *Arthritis Rheum.*, 38:727-735 (1995). All of these measures have large values for the smallest detectable difference, but by requiring simultaneous improvement in five of the seven aspects of the same process (disease activity), the randomness of the seven measurement errors is constrained, and it is easier to attribute real improvement to the individual.

In RA, joint damage is a prominent feature. Radiologic parameters of joint destruction are seen as a key outcome measure in descriptions of disease outcome. In the recent OMERACT (Outcome Measures in Rheumatology Clinical Trials) consensus meeting, radiology was chosen as part of the core set of outcome measures for longitudinal observational studies. Wolfe et al., *Arthritis Rheum.*, 41 Supp 9: S204 (1998) abstract. Radiology is also part of the WHO/ILAR (World Health Organization/International League of Associations for Rheumatology) required core set of measures for long-term clinical trials. Tugwell and Boers, *J. Rheumatol.*, 20:528-530 (1993).

Available data on the outcome of radiologic damage in RA have been obtained in both short-term and long-term studies. In short-term studies of RA patients with recent-onset disease, radiographs obtained every six months showed that after an initial rapid progression, there was diminution of the progression rate of radiologic damage in the hands and feet after two to three years. Van der Heijde et al., *Arthritis Rheum.*, 35: 26-34 (1992); Fex et al., *Br. J. Rheumatol.*, 35: 1106-1055 (1996). In long-term studies with radiographs taken less frequently, a constant rate of progression was found, with relentless deterioration of damage up to 25 years of disease duration. Wolfe and Sharp, *Arthritis Rheum.*, 41:1571-1582 (1998); Graudal et al., *Arthritis Rheum.*, 41:1470-1480 (1998); Plant et al., *J. Rheumatol.*, 25:417-426 (1998); Kaarela and Kautiainen, *J. Rheumatol.*, 24:1285-1287 (1997). Whether these differences in radiographic progression pattern are due to differences in the scoring techniques is not clear.

The scoring systems used differ in the number of joints being scored, the presence of independent scores for erosions (ERO) and joint space narrowing (JSN), the maximum score per joint, and the weighing of a radiologic abnormality. As yet, there is no consensus on the scoring method of preference. During the first three years of follow-up in a cohort study of patients with early arthritis, JSN and ERO were found to differ in their contribution to the measured progression in radiologic damage of the hands and feet. Van der Heijde et al., *Arthritis Rheum.*, 35:26-34 (1992). Furthermore, methods that independently score ERO and JSN, such as the Sharp and Kellgren scores, were found to be more sensitive to change in early RA than methods using an overall measure, such as the Larsen score. Plant et al., *J. Rheumatol.*, 21:1808-1813 (1994); Cuchacovich et al., *Arthritis Rheum.*, 35:736-739 (1992). The Sharp score is a very labor-intensive method. Van der Heijde, *Baillieres Clin. Rheumatol.*, 10:435-533 (1996). In late or destructive RA, the Sharp and the Larsen methods were found to provide similar information. However, the sensitivity to change of the various scoring methods late in the disease has not yet been investigated, and it can be argued that the scoring methods that independently measure ERO and JSN provide useful information. Pincus et al., *J. Rheumatol.*, 24:2106-2122 (1997). See also Drossaers-Bakker et al. *Arthritis Rheum.*, 43:1465-1472 (2000), which compared the three radiologic scoring systems for the long-term assessment of RA.

Paulus et al., *Arthritis Rheum.*, 50: 1083-1096 (2004) categorized radiographic joint damage as progressive or non-progressive in individuals with RA participating in clinical trials, and concluded that RA joint damage in an observational cohort can be classified as progressive or non-progressive with the use of a composite definition that includes a number of imprecise and related, but distinct, measures of structural joint damage. It appears that in day-to-day clinical management of an RA patient, an interval change between a pair of radiographs of at least five Sharp radiographic damage score units should be present before one considers the structural change to be real and uses it as the basis for a treatment decision.

Certain RA Therapeutic Agents

Initial therapy of RA typically involves administration of one or more of the following drugs: nonsteroidal antiinflammatory drugs (NSAIDs), e.g., acetylsalicylic acid (e.g., aspirin), ibuprofen (Motrin), naproxen (Naprosyn), indomethacin (Indocin), nabumetone (Relafen), tolmetin (Tolectin); glucocorticoid (via joint injection); and low-dose prednisone. See "Guidelines for the management of rheumatoid arthritis," Arthritis & Rheumatism 46(2): 328-346 (February, 2002). The majority of patients with newly diagnosed RA are started with disease-modifying antirheumatic drug (DMARD) therapy within 3 months of diagnosis. DMARDs commonly used in RA are hydroxychloroquine, sulfasalazine, methotrexate (plus oral and subcutaneous methotrexate), leflunomide, azathioprine, D-penicillamine, Gold (oral), Gold (intramuscular), minocycline, cyclosporine, *Staphylococcal* protein A immunoadsorption. In certain instances, patients are treated with immunomodulating agents such as azathioprine or cyclophosphamide. Additional RA therapeutic agents include an anti-cytokine agent (e.g., anti-tumor necrosis factor α, anti-interleukin-1-receptor (e.g., anakinra), anti-interleukin 10, anti-interleukin 6 receptor, anti-interleukin 6, anti-interferon alpha, anti-B-lymphocyte stimulator), an inhibitor of costimulation (e.g., anti-CD154, CTLA4-Ig (e.g., abatacept)).

In certain instances, TNFα inhibitors have been used for therapy of RA. Exemplary TNFα inhibitors include etanercept (sold under the trade name ENBREL®), infliximab (sold under the trade name REMICADE®), adalimumab (sold under the trade name HUMIRA®), golimumab (sold under the trade name SIMPONI™) and certolizumab pegol (sold under the trade name CIMZIA®).

Etanercept (sold under the trade name ENBREL®) is an injectable drug approved in the U.S. for therapy of active RA. Etanercept binds to TNFα and serves to remove most TNFα from joints and blood, thereby preventing TNFα from promoting inflammation and other symptoms of rheumatoid arthritis. Etanercept is an "immunoadhesin" fusion protein consisting of the extracellular ligand binding portion of the human 75 kD (p75) tumor necrosis factor receptor (TNFR) linked to the Fc portion of a human IgG1. The drug has been associated with negative side effects including serious infections and sepsis, and nervous system disorders such as multiple sclerosis (MS). See, e.g., www.remicade-infliximab.com/pages/enbrel_embrel.html.

Infliximab, sold under the trade name REMICADE®, is an immune-suppressing drug prescribed to treat RA and Crohn's disease. Infliximab is a chimeric monoclonal antibody that binds to TNFα and reduces inflammation in the body by targeting and binding to TNFα which produces inflammation. Infliximab has been linked to certain fatal reactions such as heart failure and infections including tuberculosis as well as demyelination resulting in MS. See, e.g., www.remicade-infliximab.com.

In 2002, Abbott Laboratories received FDA approval to market adalimumab (sold under the trade name HUMIRA®), previously known as D2E7. Adalimumab is a human monoclonal antibody that binds to TNFα and is approved for reducing the signs and symptoms and inhibiting the progression of structural damage in adults with moderately to severely active RA who have had insufficient response to one or more traditional disease modifying DMARDs.

In April 2009, Centocor Ortho Biotech Inc. received FDA approval to market golimumab (sold under the trade name SIMPONI™) for patients with moderate to severe RA, psoriatic arthritis, and ankylosing spondylitis. Golimumab is a human IgG1κ monoclonal antibody specific for human TNFα and which is self-administered by patients subcutaneously once every month. Golimumab binds to both soluble and transmembrane bioactive forms of TNFα. Similar to other agents that inhibit TNFα, golimumab has been associated with certain adverse events such as risk of infection, including serious and life-threatening fungal infections.

In May 2009, certolizumab pegol (sold under the trade name CIMZIA®) was approved by the FDA for treatment of patients with RA. It is administered by a healthcare professional by subcutaneous injection every two weeks during induction and then every four weeks during maintenance. Certolizumab pegol is a recombinant, humanized antibody Fab' fragment, with specificity for human TNFα, conjugated to an approximately 40 kDa polyethylene glycol (PEG2MAL40K). Certolizumab pegol has also been associated with certain safety risks such as increased risk of serious infection, similar to other TNFα inhibitors.

In certain instances, the rituximab antibody (sold under the trade name RITUXAN®) has been used as a therapy for RA. Rituximab is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.).

Another anti-CD20 antibody is ocrelizumab. Ocrelizumab is a humanized variant of an anti-CD20 antibody, 2H7. Such humanized 2H7 variants are described, for example, in International Publication No. WO 2004/056312 (International Application No. PCT/US2003/040426).

RA therapeutic agents having B-cell antagonist activity can be identified, for example, by screening compounds for certain biological properties. For example, a method of screening can be employed as described in Sundberg et al., *Cancer Research* 66, 1775-1782 (2006) wherein a compound was screened for inhibition of B-cell proliferation by targeting c-myc protein for rapid and specific degradation. See also Mackay et al., *Annual Review of Immunology*, 21: 231-264 (2003) regarding BAFF, APRIL, and a tutorial on B-cell survival and screening, and Thangarajh et al., *Scandinavian J. Immunol.*, 65(1):92 (2007) on B-cell proliferation and APRIL. In addition, Sakurai et al., *European J. Immunol.*, 37(1):110 (2007) discloses that TACI attenuates antibody production co-stimulated by BAFF-R and CD40. Further, Acosta-Rodriguez et al., *European J. Immunol.*, 37(4):990 (2007) discloses that BAFF and LPS cooperate to induce B cells to become susceptible to CD95/Fas-mediated cell death. Further screening methods can be found in Martin and Chan, "B Cell Immunobiology in Disease: Evolving Concepts from the Clinic Annual Review of Immunology," 24:467-496 (2006), Pillai et al., "Marginal Zone B Cells" *Annual Review of Immunology*, 23:161-196 (2005), and Hardy and Hayakawa, "B Cell Development Pathways," *Annual Review of Immunology*, 19:595-621 (2001). From these and other references the skilled artisan can screen for the appropriate antagonists. Microarrays can be used for this purpose (Hagmann, *Science*, 290:82-83 (2000)), as well as RNA interference (RNAi) (Ngo et al., *Nature*, 441:106-110 (2006)).

B-cell antagonists included within the scope of the present invention include antibodies, synthetic or native-sequence peptides, immunoadhesins, and small-molecule antagonists that bind to a B-cell surface marker or a B-cell specific survival or proliferation factor, optionally conjugated with or fused to another molecule. In certain embodiments, the antagonist comprises an antibody or immunoadhesin. It includes BLyS antagonists such as immunoadhesins, including, but not limited to, anti-CD23 (e.g., lumiliximab), anti-CD20, anti-CD22, or anti-BR3 antibodies, APRIL antagonists, and/or BLyS immunoadhesins. In certain embodiments, the BLyS immunoadhesin is selected from BR3 immunoadhesin comprising the extracellular domain of BR3, TACI immunoadhesin comprising the extracellular domain of TACI, and BCMA immunoadhesin comprising the extracellular domain of BCMA. Certain embodiments of BR3 immunoadhesin include hBR3-Fc as described in WO 2005/00351, U.S. Pat. Pub. No. 2005/0095243, U.S. Pat. Pub. No. 2005/0163775 and WO 2006/068867. In certain embodiments, the BLyS antagonist is an anti-BLyS antibody, wherein the anti-BLyS antibody binds BLyS within a region of BLyS comprising residues 162-275, or an anti-BR3 antibody, wherein the anti-BR3 antibody binds BR3 in a region comprising residues 23-38 of human BR3. In certain embodiments, the immunoadhesins are selected from TACI-Ig (atacicept) and BR3-Ig. In certain embodiments, the B-cell antagonist is to CD20, CD22, BAFF, or APRIL. In certain such embodiments, the antagonist is an antibody or TACI-Ig.

The CD22 antigen, or CD22, also known as BL-CAM or Lyb8, is a type 1 integral membrane glycoprotein with molecular weight of about 130 (reduced) to 140 kD (unreduced). It is expressed in both the cytoplasm and cell membrane of B-lymphocytes. CD22 antigen appears early in B-cell lymphocyte differentiation at approximately the same stage as the CD19 antigen. Unlike certain other B-cell markers, CD22 membrane expression is limited to the late differentiation stages comprised between mature B cells (CD22+) and plasma cells (CD22−). The CD22 antigen is described, for example, in Wilson et al., *J. Exp. Med.*, 173:137 (1991) and Wilson et al., *J. Immunol.*, 150:5013 (1993).

Certain exemplary anti-CD22 antibodies include those described in EP 1,476,120 (Tedder and Tuscano), EP 1,485,130 (Tedder), and EP 1,504,035 (Popplewell et al.), as well as those described in U.S. Pat. Pub. No. 2004/0258682 (Leung et al.), U.S. Pat. No. 5,484,892 (Dana-Farber), U.S. Pat. No. 6,183,744 (Immunomedics, epratuzumab), and U.S. Pat. No. 7,074,403 (Goldenberg and Hansen).

BLyS (also known as BAFF, TALL-1, THANK, TNFSF13B, or zTNF4) is a member of the TNF1 ligand superfamily that is essential for B-cell survival and maturation. BAFF overexpression in transgenic mice leads to B-cell hyperplasia and development of severe autoimmune disease (Mackay et al., *J. Exp. Med.*, 190:1697-1710 (1999); Gross et al., *Nature*, 404:995-999 (2000); Khare et al., *Proc. Natl. Acad. Sci. U.S.A*, 97:3370-3375 (2000)). BAFF levels are elevated in human patients with a variety of autoimmune disorders, such as SLE, RA, and Sjögren's syndrome (Cheema et al., *Arthritis Rheum.*, 44:1313-1319 (2001); Groom et al, *J. Clin. Invest.*,109:59-68 (2002); Zhang et al., *J. Immunol.*, 166:6-10 (2001)). Furthermore, BAFF levels correlate with disease severity, suggesting that BAFF can play a direct role in the pathogenesis of these illnesses. BAFF acts on B cells by binding to three members of the TNF receptor superfamily, TACI, BCMA, and BR3 (also known as BAFF-R) (Gross et al., supra; Thompson et al., Science, 293:2108-2111 (2001); Yan et al., Curr. Biol. 11:1547-1552 (2001); Yan et al., Nat. Immunol., 1:37-41 (2000); Schiemann et al., Science, 293:2111-2114 (2001)).

Of the three, only BR3 is specific for BAFF; the other two also bind the related TNF family member, A proliferation-inducing ligand (APRIL). Comparison of the phenotypes of BAFF and receptor knockout or mutant mice indicates that signaling through BR3 mediates the B-cell survival functions of BAFF (Thompson et al., supra; Yan et al., supra, 2001; Schiemann et al., supra). In contrast, TACI ap-pears to act as an inhibitory receptor (Yan, Nat. Immunol., 2:638-643 (2001)), while the role of BCMA is unclear (Schiemann et al., supra). US 2007/0071760 discloses treating B-cell malignancies using a TACI-Ig fusion molecule in an amount sufficient to suppress proliferation-inducing functions of BlyS and APRIL.

BR3 is a 184-residue type III transmembrane protein expressed on the surface of B cells (Thompson et al., supra; Yan, Nat. Immun., supra). The intracellular region bears no sequence similarity to known structural domains or protein-protein interaction motifs. Nevertheless, BAFF-induced signaling through BR3 results in processing of the transcription factor NF-B2/p100 to p52 (Claudio et al., Nat. Immunol., 3:958-965 (2002); Kayagaki et al., Immunity, 10:515-524 (2002)). The extracellular domain (ECD) of BR3 is also divergent. TNFR family members are usually characterized by the presence of multiple cysteine-rich domains (CRDs) in their extracellular region; each CRD is typically composed of about 40 residues stabilized by six cysteines in three disulfide bonds. Conventional members of this family make contacts with ligand through two CRDs interacting with two distinct patches on the ligand surface (Bodmer et al., Trends Biochem. Sci., 27:19-26 (2002)). However, the BR3 ECD contains only four cysteine residues, capable of forming a partial CRD at most, raising the question of how such a small receptor imparts high-affinity ligand binding.

It has been shown that the BAFF-binding domain of BR3 resides within a 26-residue core region (Kayagaki et al., supra). Six BR3 residues, when structured within a β-hairpin peptide (bhpBR3), were sufficient to confer BAFF binding and block BR3-mediated signaling. Others have reported polypeptides purported to interact with BAFF (e.g., WO 2002/24909, WO 2003/035846, WO 2002/16312, and WO 2002/02641).

Loss of function and radiographic change occur early in the course of the disease. These changes can be delayed or prevented with the use of certain DMARDs. Although several DMARDs are initially clinically effective and well tolerated, many of these drugs become less effective or exhibit increased toxicity over time. Based on its efficacy and tolerability, MTX has become the standard therapy by which other treatments are measured. Bathon et al., N. Eng. J. Med., 343:1586-1593 (2000); Albert et al., J. Rheumatol., 27:644-652 (2000).

Recent studies have examined radiographic progression in patients with late-stage RA who have taken leflunomide, MTX, or placebo (Strand et al., Arch. Intern. Med., 159: 2542-2550 (1999)) as well as patients who have taken infliximab plus MTX or placebo plus MTX following a partial response to MTX. Lipsky et al., N. Engl. J. Med., 343:1594-1602 (2000); Maini et al., Lancet, 354:1932-1939 (1999). In the first year of the ENBREL™ ERA (early RA) trial, etanercept was shown to be significantly more effective than MTX in improving signs and symptoms of disease and in inhibiting radiographic progression. Bathon et al., N. Eng. J. Med., 343:1586-1593 (2000). Genovese et al., Arthritis Rheum. 46:1443-1450 (2002) reports results from the second year of the study, concluding that etanercept as monotherapy was safe and superior to MTX in reducing disease activity, arresting structural damage, anti decreasing disability over two years in patients with early aggressive RA. Also studied was the safety and clinical activity of ocrelizumab (a humanized antibody targeting C D20+B cells) in combination with MTX in moderate-to-severe RA patients (Ph I/II ACTION study). Genovese et al., Arthritis Rheum., 54(9): S66-S67 (September 2006).

Further, reduction in radiographic progression in the hands and feet was observed in patients with early RA after receiving infliximab in combination with MTX. Van der Heijde et al., Annals Rheumatic Diseases, 64:417 (2005). Patients with early RA achieved a clinically meaningful and sustained improvement in physical function after treatment with infliximab. Smolen et al., Annals Rheumatic Diseases, 64:418-419 (2005).

The effect of infliximab therapy on hone mineral density in patients with ankylosing spondylitis (AS) resulting from a randomized, placebo-controlled trial named ASSERT) is reported by Van der Heijde et al., Annals Rheumatic Diseases, 64:319 (2005). The ASSERT trial showed that infliximab improved fatigue and pain in patients with AS. Van der Heijde et al., Annals Rheumatic Diseases, 64:318-319 (2005). The efficacy and safety of infliximab in AS patients treated according to ASSERT are described by van der Heijde et al., Arthritis Rheum., 5:582-591 (2005). The authors conclude that infliximab was well tolerated and effective in a large cohort of patients with AS during a 24-week study period. In addition, the effect of infliximab therapy on spinal inflammation was assessed by magnetic resonance imaging in a randomized, placebo-controlled trial of 279 patients with AS. Van der Heijde et al., Annals Rheumatic Diseases, 64:317 (2005). The manner in which the treatment effect on spinal radiographic progression in patients with AS should be measured is addressed by van der Heijde et al., Arthritis Rheum. 52:1979-1985 (2005).

The results of radiographic analyses of the infliximab multinational PsA controlled trial (IMPACT) after one year are reported by Antoni et al., Annals Rheumatic Diseases 64:107 (2005). Evidence of radiographic benefit of treatment with infliximab plus MTX in RA patients who had no clinical improvement, with a detailed subanalysis of data from the anti-TNF trial in RA with concomitant therapy study, is reported by Smolen et al., Arthritis Rheum. 52:1020-1030 (2005). Radiographic progression (as measured by mean change in modified Sharp/van der Heijde score) was much greater in patients receiving MTX plus placebo than in patients receiving infliximab plus MTX. The authors conclude that even in patients without clinical improvement, treatment with infliximab plus MTX provided significant benefit with regard to the destructive process, suggesting that in such patients these two measures of disease are dissociated. The association between baseline radiographic damage and improvement in physical function after treatment of patients having RA with infliximab is described by Breedveld et al., Annals Rheumatic Diseases, 64:52-55 (2005). Structural damage was assessed using the van der Heijde modification of the Sharp score. The authors conclude that greater joint damage at baseline was associated with poorer physical function at baseline and less improvement in physical function after treatment, underlining the importance of early intervention to slow the progression of joint destruction.

Rheumatoid Arthritis Molecular Biomarkers

A number of investigators have carried out microarray gene expression profiling studies of synovial tissue isolated from RA patients. The published studies include van der Pouw Kraan T C et al., Discovery of distinctive gene expression profiles in rheumatoid synovium using cDNA microarray technology: evidence for the existence of multiple pathways of tissue destruction and repair, *Genes Immun* April; 4(3):187-96 (2003); van der Pouw Kraan T C, et al., Rheumatoid arthritis is a heterogeneous disease: evidence for differences in the activation of the STAT-1 pathway between rheumatoid tissues, *Arthritis Rheum August;* 48(8): 2132-45 (2003); Finis K et al., Analysis of pigmented villonodular synovitis with genome-wide complementary DNA microarray and tissue array technology reveals insight into potential novel therapeutic approaches, *Arthritis Rheum* March; 54(3):1009-19 (2006); Lindberg J, et al., Effect of infliximab mRNA expression profiles in synovial tissue of rheumatoid arthritis patients, *Arthritis Res Ther.* 8(6):R179 (2006); van der Pouw Kraan T C et al., Responsiveness to anti-tumour necrosis factor alpha therapy is related to pretreatment tissue inflammation levels in rheumatoid arthritis patients, *Ann Rheum Dis.* April; 67(4):563-6 (2008); Huber R et al., Identification of intra-group, inter-individual, and gene-specific variances in mRNA expression profiles in the rheumatoid arthritis synovial membrane, *Arthritis Res Ther* 10(4):R98 (2008); Badot V et al., Gene expression profiling in the synovium identifies a predictive signature of absence of response to adalimumab therapy in rheumatoid arthritis, *Arthritis Res Ther.* 11(2):R57 (2009), Epub 2009 Apr. 23.

International Patent Application No. PCT/US2010/047734 (Intn'l Pub. No. WO2011/028945) describes a statistically rigorous interrogation of genome-wide transcription in a large set of RA synovial tissues. RA joints were stratified into four molecular phenotypes that differed transcriptionally but not in disease duration, radiographic state or systemic measures of inflammation. Meta-analysis revealed that each phenotype expressed distinct transcriptional programs reflecting biological differences with pathological relevance. Gene expression modules were developed for each phenotype, refined using statistical learning procedures and validated on independent data sets. In addition, phenotype-intrinsic modules were used to identify molecular biomarkers to stratify new patients into subtypes of RA with predictable responses to B cell targeted therapy, such as anti-CD20 monoclonal antibodies.

Multiple Sclerosis and Certain Therapeutic Agents

Multiple Sclerosis (MS) is a disorder of the central nervous system that affects the brain and spinal cord. MS generally exhibits a relapsing-remitting course or a chronic progressive course. Relapsing-remitting MS (RRMS) is characterized by partial or total recovery after attacks. Secondary-progressive MS (SPMS) is a relapsing-remitting course which becomes steadily progressive. Attacks and partial recoveries may continue to occur. Primary-progressive MS (PPMS) is progressive from the onset. Symptoms in patients with PPMS generally do not remit—i.e., decrease in intensity.

Common signs and symptoms of MS include paresthesias in one or more extremities, in the trunk, or on one side of the face; weakness or clumsiness of a leg or hand; or visual disturbances (such as partial blindness and pain in one eye), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances (Berkow et al. (ed.), 1999, Merck Manual of Diagnosis and Therapy: 17th Ed). The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4− T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood. Current treatments for MS include corticosteroids, beta interferons (BETAFERON®), AVONEX®, REBIF®), glatiramer acetate (COPAXONE®), methotrexate, azathioprine, cyclophosphamide, cladribine, baclofen, tizanidine, amitriptyline, carbamazepine (Berkow et al. (ed.), 1999, supra) and natalizumab (TYSABRI®).

ANCA-Vasculitis and Certain Therapeutic Agents

Wegener's granulomatosis and microscopic polyangiitis are classified as antineutrophil cytoplasmic antibody (ANCA)-associated vasculitides because most patients with generalized disease have antibodies against proteinase 3 or myeloperoxidase. (Jennette J C et al., Arthritis Rheum 37:187-192 (1994); Finkielman J D et al., Am J Med 120(7):643.e9-643.14 (2007)) The ANCA-associated vasculitides affect small-to-medium-size blood vessels, with a predilection for the respiratory tract and kidneys. (Hoffman G S et al., Ann Intern Med 116:488-498 (1992); Guillevin L et al., Arthritis Rheum 42:421-430 (1999); Reinhold-Keller E et al., Arthritis Rheum 43:1021-1032 (2000); Stone J H. Arthritis Rheum 48:2299-2309 (2003)). Cyclophosphamide and glucocorticoids have been the standard therapy for remission induction for nearly four decades. (Novack S N et al., N Engl J Med 284:938-942 (1971); Fauci A S et al., Medicine (Baltimore) 52:535-561 (1973)). This regimen transformed the usual treatment outcome of severe ANCA-associated vasculitis from death to a strong likelihood of disease control and temporary remission. (Hoffman G S et al., supra; Guillevin L et al., supra; Reinhold-Keller supra; Walton E W., BMJ 2:265-270 (1958); Jayne D et al., N Engl J Med 349:36-44 (2003); The Wegener's Granulomatosis Etanercept Trial (WGET) Research Group, N Engl J Med 352:351-361 (2005). However, not all patients have a remission with this combination of drugs, and those who do often have disease flares that require repeated treatment. Moreover, side effects of cyclophosphamide, including infertility, cytopenias, infections, bladder injury, and cancer, as well as the multiple adverse effects of lengthy courses of glucocorticoid treatment, are major causes of long-term disease and death. (Hoffman G S et al., supra; Guillevin L et al., supra; Reinhold-Keller supra; Jane et al., supra; WGET supra; Stone J H, et al., Arthritis Rheum 54:1608-1618 (2006); Pagnoux C, et al., Arthritis Rheum 58:2908-2918 (2008)).

A number of studies have shown that rituximab demonstrates clinical activity in Wegener's granulomatosis and ANCA-vasculitis. For example, Specks et al. disclosed successful use of four infusions of 375 mg/m² of rituximab and high-dose glucocorticoids to treat Wegener's granulomatosis. (Specks et al. *Arthritis & Rheumatism*, 44(12): 2836-2840 (2001)). In another study rituximab was found to be a well-tolerated, effective remission induction agent for severe ANCA-associated vasculitis, when used in a dose of 375 mg/m²×four along with oral prednisone at 1 mg/kg/day, which was reduced to 40 mg/day by week four, and to total discontinuation over the following 16 weeks. Four patients were re-treated with rituximab alone for recurring/rising ANCA titers. Other than glucocorticoids, no additional immunosuppressive agents seem necessary for remission induction and maintenance of sustained remission (six months or longer). Keogh et al., *Kidney Blood Press. Res.*, 26:293 (2003) reported that eleven patients with refractory ANCA-associated vasculitis went into remission upon treatment with four weekly 375 mg/m² doses of rituximab and high-dose glucocorticoids. Patients with refractory ANCA-associated vasculitis were administered rituximab along with immunosuppressive medicaments such as intravenous CTX, mycophenolate mofetil, azathioprine, or leflunomide, with apparent efficacy. See also, Eriksson, "*Kidney and Blood Pressure Research*, 26:294 (2003) (five patients with ANCA-associated vasculitis treated with rituximab 375 mg/m² once a week for four weeks responded to the treatment); Jayne et al., *Kidney and Blood Pressure Research*, 26:294-295 (2003) (six patients with refractory vasculitis receiving four weekly infusions of rituximab at 375 mg/m² with CTX along with background immunosuppression and prednisolone experienced major falls in vasculitic activity). A further report of using rituximab along with intravenous CTX at 375 mg/m² per dose in four doses for administering to patients with refractory systemic vasculitis is provided in Smith and Jayne, "A prospective, open label trial of B-cell depletion with rituximab in refractory systemic vasculitis" poster 998 (11$^{th}$ International Vasculitis and ANCA workshop), American Society of Nephrology, *J. Am. Soc. Nephrol.*, 14:755A (2003). See also Eriksson, *J. Internal Med.*, 257:540-548 (2005) regarding nine patients with ANCA-positive vasculitis who were successfully treated with two or four weekly doses of 500 mg of rituximab; and Keogh et al., *Arthritis and Rheumatism*, 52:262-268 (2005), who reported that in 11 patients with refractory ANCA-associated vasculitis, treatment or re-treatment with four weekly 375 mg/m² doses of rituximab induced remission by B-lymphocyte depletion (study conducted from January 2000 to September 2002). More recently, Stone et al. reported noninferiority of rituximab therapy (375 mg/m² per week for 4 weeks) compared to cyclosphosphamide treatment for induction of remission in severe ANCA-associated vasculitis and possible superiority in relapsing disease. (Stone et al., N. England J. Med. 363(3):221-231 (2010)).

Certain Additional Autoimmune Diseases

An autoimmune disease can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). Exemplary diseases include autoimmune rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary binary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathics), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)).

Specific examples of other autoimmune disorders as defined herein, which in some cases encompass those listed above, include, but are not limited to, arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, hives, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scrod, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, agranulocytosis, vasculitides (including large-vessel vasculitis such as polymyalgia rheumatica and giant-cell (Takayasu's) arteritis, medium-vessel vasculitis such as Kawasaki's disease and polyarteritis nodosa/periarteritis nodosa, immunovasculitis, CNS vasculitis, cutaneous vasculitis, hypersensitivity vasculitis, necrotizing vasculitis such as fibrinoid necrotizing vasculitis and systemic necrotizing vasculitis, ANCA-negative vasculitis, and ANCA-associated vasculitis such as Churg-Strauss syndrome (CSS), Wegener's granulomatosis, and microscopic polyangiitis), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated, diseases, anti-glomerular basement membrane disease, anti-phospholipid antibody syndrome, motoneuritis, allergic neuritis, Behcet's disease/syndrome, Castleman's syndrome, Goodpasture's syndrome, Reynaud's syndrome, Sjögren's syndrome, Stevens-Johnson syndrome, pemphigoid pemphigus such as pemphigoid bullous, cicatricial (mucous membrane) pemphigoid, skin pemphigoid, pemphigus vulgaris, paraneoplastic pemphigus, pemphigus foliaceus, pemphigus mucus-membrane pemphigoid, and pemphigus erythematosus, epidermolysis bullosa acquisita, ocular inflammation, including allergic ocular inflammation such as allergic conjunctivis, linear IgA bullous disease, autoimmune-induced conjunctival inflammation, autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, Grave's eye disease (ophthalmopathy or thyroid-associated ophthalmopathy), polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs. NSIP, Guillain-Barré syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, keratitis such as Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, eyelids such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryogbulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica (sympathetic ophthalmitis), neonatal ophthalmitis, optic neuritis, orchids granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the present invention can be generated using standard techniques known in the art.

Gene expression signatures and biomarkers associated with predicting responsiveness of RA patients and patients suffering with other autoimmune diseases such as MS and ANCA-vasculitis to certain therapeutic agents are provided herein. These signatures as well as expression levels of the mRNA or individual proteins encoded by the genes constitute biomarkers for predicting responsiveness to RA therapeutic agents, MS therapeutic agents, and/or ANCA-vasculitis therapeutic agents. Accordingly, the invention disclosed herein is useful in a variety of settings, e.g., in methods and compositions related to diagnosis and therapy of autoimmune diseases.

Detection of Gene Expression Levels

Nucleic acid, according to any of the methods described herein may be RNA transcribed from genomic DNA or cDNA generated from RNA or mRNA. Nucleic acid may be derived from a vertebrate, e.g., a mammal. A nucleic acid is said to be "derived from" a particular source if it is obtained directly from that source or if it is a copy of a nucleic acid found in that source.

Nucleic acid includes copies of the nucleic acid, e.g., copies that result from amplification. Amplification may be desirable in certain instances, e.g., in order to obtain a desired amount of material for detecting variations. The amplicons may then be subjected to a variation detection method, such as those described below, to determine expression of certain genes.

Levels of mRNA may be measured and quantified by various methods well-known to those skilled in the art, including use of commercially available kits and reagents. One such method is polymerase chain reaction (PCR). Another method, for quantitative use, is real-time quantitative PCR, or qPCR. See, e.g., "PCR Protocols, A Guide to Methods and Applications," (M. A. Innis et al., eds., Academic Press, Inc., 1990); "Current Protocols in Molecular Biology" (F. M. Ausubel et al., eds., 1987, and periodic updates); and "PCR: The Polymerase Chain Reaction", (Mullis et al., eds., 1994).

A microarray is a multiplex technology that typically uses an arrayed series of thousands of nucleic acid probes to hybridize with, e.g, a cDNA or cRNA sample under high-stringency conditions. Probe-target hybridization is typically detected and quantified by detection of fluorophore-, silver-, or chemiluminescence-labeled targets to determine relative abundance of nucleic acid sequences in the target. In typical microarrays, the probes are attached to a solid surface by a covalent bond to a chemical matrix (via epoxy-silane, amino-silane, lysine, polyacrylamide or others). The solid surface is for example, glass, a silicon chip, or microscopic beads. Various microarrays are commercially available, including those manufactured, for example, by Affymetrix, Inc. and Illumina, Inc.

A biological sample may be obtained using certain methods known to those skilled in the art. Biological samples may be obtained from vertebrate animals, and in particular, mammals. In certain instances, a biological sample is synovial tissue, serum or peripheral blood mononuclear cells (PBMC). By screening such body samples, a simple early diagnosis can be achieved for diseases such as RA, MS, or ANCA-vasculitis. In addition, the progress of therapy can be monitored more easily by testing such body samples for variations in expression levels of target nucleic acids (or encoded polypeptides).

Subsequent to the determination that a subject, or the tissue or cell sample comprises a gene expression signature or relative levels of certain serum biomarkers disclosed herein, it is contemplated that an effective amount of an appropriate therapeutic agent may be administered to the subject to treat the particular disease in the subject, e.g., RA, MS, or ANCA-vasculitis. Clinical diagnosis in mammals of the various pathological conditions described herein can be made by the skilled practitioner. Clinical diagnostic techniques are available in the art which allow, e.g., for the diagnosis or detection of autoimmune diseases in a mammal, e.g., RA, MS, or ANCA-vasculitis.

A therapeutic agent can be administered in accordance with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Optionally, administration may be performed through mini-pump infusion using various commercially available devices.

Kits

For use in the applications described or suggested herein, kits or articles of manufacture are also provided. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a polynucleotide specific for a polynucleotide comprising one or more genes of a gene expression signature. Where the kit utilizes nucleic acid hybridization to detect the target nucleic acid, the kit may also have containers containing nucleotide(s) for amplification of the target nucleic acid sequence and/or a container comprising a reporter means, such as a biotin-binding protein, such as avidin or streptavidin, bound to a reporter molecule, such as an enzymatic, florescent, or radioisotope label.

Kits will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above. Other optional components in the kit include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

Methods of Marketing

The invention herein also encompasses a method for marketing a therapeutic agent or a pharmaceutically acceptable composition thereof comprising promoting to, instructing, and/or specifying to a target audience, the use of the agent or pharmaceutical composition thereof for treating a patient or patient population with a particular disease, e.g., RA, MS, or ANCA-vasculitis, from which a sample has been obtained showing a gene expression signature or levels of serum biomarkers as disclosed herein.

Marketing is generally paid communication through a non-personal medium in which the sponsor is identified and the message is controlled. Marketing for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The marketing of the diagnostic method herein may be accomplished by any means. Examples of marketing media used to deliver these messages include television, radio, movies, magazines, newspapers, the internet, and billboards, including commercials, which are messages appearing in the broadcast media.

The type of marketing used will depend on many factors, for example, on the nature of the target audience to be reached, e.g., hospitals, insurance companies, clinics, doctors, nurses, and patients, as well as cost considerations and the relevant jurisdictional laws and regulations governing marketing of medicaments and diagnostics. The marketing may be individualized or customized based on user characterizations defined by service interaction and/or other data such as user demographics and geographical location.

EXAMPLES

The following are examples of the methods and compositions of the invention. It is understood that various other embodiments may be practiced, given the general description provided above.

Example 1

Introduction

Randomized and placebo controlled clinical trials have shown that rituximab is efficacious for RA patients who have failed methotrexate (MTX) and/or anti-TNF therapy (Emery P, et al., Arthritis Rheum. 2006; 54 (5):1390-400; Cohen S B, et al., Arthritis Rheum. 2006; 54 (9): 2793-806). Similar to other immunology biologics, rituximab is associated with certain risks such as infusion reactions and infection, among other possible side effects. To improve the benefit/risk equation for rituximab therapy in RA, we have been interested in identifying baseline predictive clinical features or molecular biomarkers that identify patient subpopulations with an increased response rate. Similarly, there is interest in identifying patient subsets that receive no benefit from rituximab so that alternative therapies can be prescribed. A recent study suggests that elevated levels of autoantibodies (rheumatoid factor and/or anti-CCP antibodies) and the acute phase reactant C-reactive protein enrich for responders to rituximab in RA (Sellam et al., Arthritis & Rheumatism 2011; 63:93-938; Dorner et al., Pharmacol Ther 2010; 125:464-475).

The aims of the current study were to validate an mRNA-based methodology to quantitate the levels of B lineage cells in peripheral blood, and then determine whether differences in B cell subset composition prior to therapy correlated with clinical response to rituximab in RA. The data support the concept that elevated baseline blood levels of molecular markers for late B lineage stage plasmablasts are predictive of non-response to anti-CD20 therapy in RA.

Methods and Subjects

Clinical Study Designs and Sample Collection

REFLEX was a multicenter, randomized, double-blind, placebo-controlled, phase III clinical study of rituximab (2×1000 mg) treatment in 518 patients with active RA and an inadequate response to 1 or more anti-TNF agents (TNF-IR) (Cohen S B, et al., Arthritis Rheum. 2006; 54 (9): 2793-806). DANCER was a randomized, multicenter, double-blind, placebo-controlled phase II clinical trial that enrolled 462 RA patients. Subjects were randomized to receive placebo, rituximab 2×500 mg, or rituximab 2×1000 mg, with or without glucocorticoids. A complete characterization of patient demographics, baseline clinical features and outcomes from the DANCER trial has been published (Emery P, et al., Arthritis Rheum, 2006; 54 (5):1390-400.). SERENE was a phase III randomized placebo-controlled trial to assess efficacy of two dose regimens of rituximab (2×500 mg and 2×1000 mg) in 512 RA patients with an inadequate response to methotrexate (MTX-IR) (Emery P, et al., Ann Rheum Dis. 2010 September; 69(9):1629-35. Epub 2010 May 20). Inclusion criteria for the three trials included: diagnosis of rheumatoid arthritis according to the revised American College of Rheumatology criteria at least 6 months prior to enrollment, age between 18-80 years, swollen joint counts ≥8 (66 joint count) and tender joint counts ≥8 (68 joint count) at time of screening at baseline and screening, either ESR ≥28 mm/hr or CRP ≥1.5 mg/dL (REFLEX, DANCER) or ESR ≥28 mm/hr or CRP ≥0.6 mg/dL (SERENE) at time of screening, and receiving MTX at a dose 10-25 mg/week for at least 12 weeks with the last 4 weeks at a stable dose. Additional requirements for REFLEX included a wash out period from etanercept for ≥4 weeks and Infliximab for ≥8 weeks and radiographic evidence of erosion in at least one joint. In all three trials, rituximab or placebo were administered by intravenous infusion on days one and 15 with concomitant methotrexate (10-25 mg/week as prescribed by the treating physician). In all patients, 100 mg intravenous infusion methylprednisolone was administered at least 30 minutes prior to rituximab or placebo infusion. All patients also received 5 mg/week folate.

SCRIPT was a multicenter, randomized, double-blind, placebo-controlled phase III clinical trial of ocrelizumab, a humanized anti-CD20 monoclonal antibody, in 840 TNF-IR RA patients. Patients were on a concomitant background of non-biologic DMARD therapy. Subjects were randomized into three trial arms and received 2 courses of placebo or 200 mg or 500 mg of ocrelizumab and were assessed for clinical benefit throughout 48 weeks after dosing. Inclusion criteria for the trial included RA diagnosis for at least 3 months using the 1987 ACR criteria for classification of RA, swollen joint count (66 joints) ≥4, tender joint count (68 joints) ≥4, CRP ≥0.6 mg/dL and positive rheumatoid factor and/or anti-CCP antibody status.

Baseline demographics and clinical activity measures for each of the trial populations are summarized in Tables 2 and 3 below.

For development of the mRNA-based biomarkers (see below) we used samples from the ACTION trial. ACTION was a combined phase I/II dose-ranging study of MTX plus placebo versus MTX and ocrelizumab in RA patients. Complete patient demographics, clinical findings and outcomes for the ACTION trial have been published (Genovese M C, et al, Arthritis Rheum. 2008 September; 58(9):2652-61). Whole blood PaxGene samples for RT-qPCR and microarray gene expression analysis as well as EDTA blood for FACS analysis were obtained at baseline and pre-defined timepoints in all patients enrolled in the study.

Baseline PaxGene blood RNA sample collection in all of the anti-CD20 trials was optional and obtained following informed consent. Thus, RNA samples were available from a subset only of each trial population (27%, 31%, 30% and 49% of samples from REFLEX, DANCER, SERENE and SCRIPT, respectively).

Methods

Microarray Methods and Analysis

RNA was purified at Covance (Princeton, N.J.) using the manufacturer's recommended protocol and reagents (PAXgene™ blood RNA kit, Qiagen Inc, Valencia, Calif.). The amount and quality of RNA extracted were assessed with NanoDrop (ND1000, Celbio, Mich.) and Agilent 2100 Bioanalyzer (Agilent Technologies Inc, Headquarters Santa Clara, Calif.).

RNA from a subset of 24 study patients was profiled on Agilent Whole Human Genome 4×44 microarrays (Part ID G4112-60510, Agilent Technologies Inc, Headquarters Santa Clara, Calif.). Microarray images were analyzed using Agilent's Feature Extraction (FE) software, version 9.5. Differential gene expression analysis was performed using Partek software (Partek Inc., St. Louis, Mo.). In brief, gene expression data was log-transformed and quantile normalized. A list of most significantly different genes based on fold-change and p-values between depleters and non-depleters (as determined by FACS analysis) at baseline and at day 84 post riuximab (RTX) treatment was derived using a 3 way ANOVA. The initial list constituted mainly of immunoglobulin chain genes, as well as established plasma cell markers and B cell markers. From the top 30 genes, 7 genes were chosen for further analysis, based on their performance, specificity, and preliminary in vitro experiments (data not shown).

Gene Expression Analysis

Reagents and Instrumentation

TaqMan Universal Master Mix, TaqMan PreAmp Master Mix and gene expression assays were from Applied Biosystems (Applied Biosystems, Foster City, Calif.). Pre-amplification reactions were performed using a GeneAmp PCR System 9700 (Applied Biosystems). Real-time PCR reactions were performed using either the Fluidigm digital array gene expression technology (Fluidigm Corporation, South San Francisco, Calif.) or in 384 well plates utilizing the ABI Prism 7900HT instrument (Applied Biosystems. Foster City, Calif.). Both real-time PCR methods were validated against each other in a series of QC experiments (data not shown).

Candidate mRNA Biomarker Selection

The following B cell genes were initially selected for multiplex RT-qPCR gene expression analysis: 1) genes enriched in naïve and memory B cells (CD19, CD20, POU2AF1, FCRL5 splice variant—FCRL5/IRTA2c, inventoried ABI assay HS01070204_m1, shown in preliminary experiments to be expressed predominantly on naïve and mature B cells, as opposed to IRTA 2a and b which are expressed predominantly in bone marrow plasma cells (Polson A G, et al., Int Immunol. 2006 September; 18(9):1363-73. Epub 2006 Jul. 18); 2) genes enriched in plasmablasts/plasma cells (Ig-J chain, BCMA); and 3) genes found in both B cells and (at higher levels in) plasma cells (Ig light chain). POU2AF1 did not perform well likely due its low abundance, and IgL did not discriminate mature B cells from plasmablasts in our hands; thus, these two markers were not considered further. All data were normalized for the housekeeping gene GAPDH. All primer/probe sets were TaqMan Gene Expression Assays (Applied Biosystems, Foster City, Calif.).

RNA, cDNA and qPCR

RNA was extracted from whole blood using PAXgene™ blood RNA kits, according to manufacturer's protocol (Qiagen Inc, Valencia, Calif.). The amount and quality of RNA extracted were assessed using both NanoDrop (ND1000, Celbio, Mich.) and Agilent 2100 Bioanalyzer (Agilent Technologies Inc, Santa Clara, Calif.) technologies.

In the initial step of the qPCR multiplex assay, 100 ng RNA per sample was reversed transcribed to cDNA using BioRad iScript cDNA Synthesis kit (BioRad, Hercules, Calif.) except that for the SCRIPT samples, 300 ng RNA was used and, after synthesis, diluted with water to 10 ng/ul input RNA. Subsequently, a preliminary cDNA amplification step employing specific primer pairs was performed using a commercially available cDNA preamplification kit (TaqMan PreAmp Master Mix Kit, Applied Biosystems), as previously described (Ciotti P, et al., Diagn Mol Pathol. 2009 June; 18(2):112-8). Preamplification product was diluted 1:5 with TE buffer according to the manufacturer's protocol. Samples from the SCRIPT trial were not preamplified. Quantitative PCR was performed using either the Fluidigm digital array gene expression technology (Fluidigm Corporation, South San Francisco, Calif.) or the ABI 7900HT instrument (Applied Biosystems, Foster City, Calif.). For the Fluidigm dynamic arrays, 2.25 ul preamplified cDNA per reaction was used and for the Taqman assays, 2 ul of preamplified or non-amplified cDNA (SCRIPT) was used per reaction.

To assess potential biases between pre-amplified and non-amplified product in the qPCR reactions, a range of preamplified (50 ng to 5 ng) and non-amplified RNA templates from human B cell lines and tonsil RNA were tested. Expression of each gene was measured in duplicate in each experiment, and the average of the replicates was normalized to human GAPDH to generate a delta Ct ($\Delta$Ct) value for each gene. Duplicate samples generally varied by no more than 5%. Data was analyzed using BioMark Gene Expression Data Analysis software (Fluidigm Corporation, South San Francisco, Calif.) to obtain Ct values. Expression data was then calculated as relative abundance, using the formula $2^{-\Delta Ct}$.

Assessment of Gene Expression in B Cell Lineages

Human B cells were sorted from peripheral blood or leukopacks from healthy donors using markers to distinguish between naïve B cells, unswitched and switched memory B cells and plasma cells as previously described (Abbas et al., Genes Immun 2005; 6: 319-331). Naïve B cells were CD19+CD27-IgG/A−, unswitched memory B cells were CD19+CD27+IgG/A−, and switched memory B cells were CD19+CD27+IgM−. Plasma cells were CD19+CD138+. RNA was purified and hybridized to Affymetrix® HGU133A and HGU133B GeneChips®. Mean probe expression levels for IgJ, FcRL5/IRTA2c, CD19 and BCMA were determined from the respective normalized fluorescence values for each B cell population.

Statistical Analyses

Select clinical case report form data was transferred from clinical trial databases at Genentech into a customized Oracle database designed to facilitate biomarker discovery. Data analysis was performed using JMP software (SAS, Cary, N.C.), and all statistical analysis was performed using GraphPad Prism software (GraphPad, La Jolla, Calif.).

Differences in expression between ACR50 responders vs. non-responders in the active and placebo arms with respect to the linearly transformed values were assessed using the nonparametric Mann-Whitney test.

A threshold sensitivity method was applied, to baseline RNA samples from the REFLEX trial in order to identify candidate biomarker thresholds that enriched for placebo corrected lack of response as defined by failure to achieve ACR50 at 24 weeks. The threshold sensitivity method and analysis were carried out as follows.

To identify subgroups with increased clinical benefit, the study population from REFLEX was stratified using baseline clinical characteristics and serological biomarkers measured in patients for whom serum samples were available. The baseline characteristics for the patient subgroups that had matching biomarker serum samples were comparable with the overall patient group in the clinical trial. For surveys of each continuous biomarker (where a range of discrete values was possible) and outcome measure ACR50 at week 24, a plot was generated presenting subgroup efficacy differentials versus a range of potential threshold values (20th-80th biomarker percentiles in 5-percentile increments) to control bias. The threshold giving the largest efficacy differential ($\Delta$high-$\Delta$low) was then identified. For this threshold, a permutation test was used to address statistical significance. For each permutation, biomarker values were permuted and both treatment assignment and the outcome measure were fixed. The largest efficacy differential was computed for the permutated data set, which was compared to the largest efficacy differential observed from the original data. Permutation p-values were based on 2000 permutations. A 95% confidence interval on the largest efficacy differential was calculated. Four biomarkers with the highest efficacy differentials (CRP, IgG-anti-CCP, IgA-RF and sCD25) that identified subgroups in REFLEX with enhanced clinical benefit in rituximab-treated patients were then prioritized and further investigated in the SERENE trial dataset. In addition, five of their two-biomarker (bivariate) combinations were also studied. The sixth combination, IgG-anti-CCP and IgA-RF, was not considered due to a high correlation between the two markers. Because CRP is one of the components of the ACR efficacy measure, also DAS-ESR was prioritized for testing in the SERENE data set.

Recently, it was reported that there were no significant differences in either clinical or safety outcomes between rituximab doses in the SERENE trial (500 mg and 1000 mg) (Emery P, et al., Ann Rheum Dis. 2010 September; 69(9): 1629-35. Epub 2010 May 20). Because ACR50 response rates were similar between the rituximab 500-mg (26.3%; n=167) and rituximab 1000-mg (25.9%; n=170) dose groups at 24 weeks in SERENE and pharmacodynamic properties were comparable between the two doses (Emery P, et al., Arthritis Rheum. 2006; 54 (5):1390-400), we combined both doses as a single treatment group for this analysis. Each biomarker was analyzed as described for REFLEX. Each of five bivariate subgroup candidates was constructed using an "and" rule and applying the same direction (i.e. high or low) that defined the best subgroup for the individual biomarkers. Bivariate subgroup candidates were formed by comparing patients with both elevated CRP and elevated IgA RE to patients who were not in this subgroup; subgroups were determined by 30th, 40th, 50th, 60th and 70th percentiles of either CRP or IgA-RF with the constraint that at least 20% of the patients were in each subgroup to control bias. Exploratory analyses of other non-prioritized baseline biomarkers (e.g. IgM-RF, IgG-RF, and IgG-anti-CCP) and combinations of biomarkers were also performed.

The thresholds for the predictive biomarkers and two-biomarker combinations once established in the REFLEX trial were then prospectively tested following a pre-specified diagnostic plan using data from the replication cohort, which was comprised of samples combined from the SERENE and DANCER trials.

Figure 6:
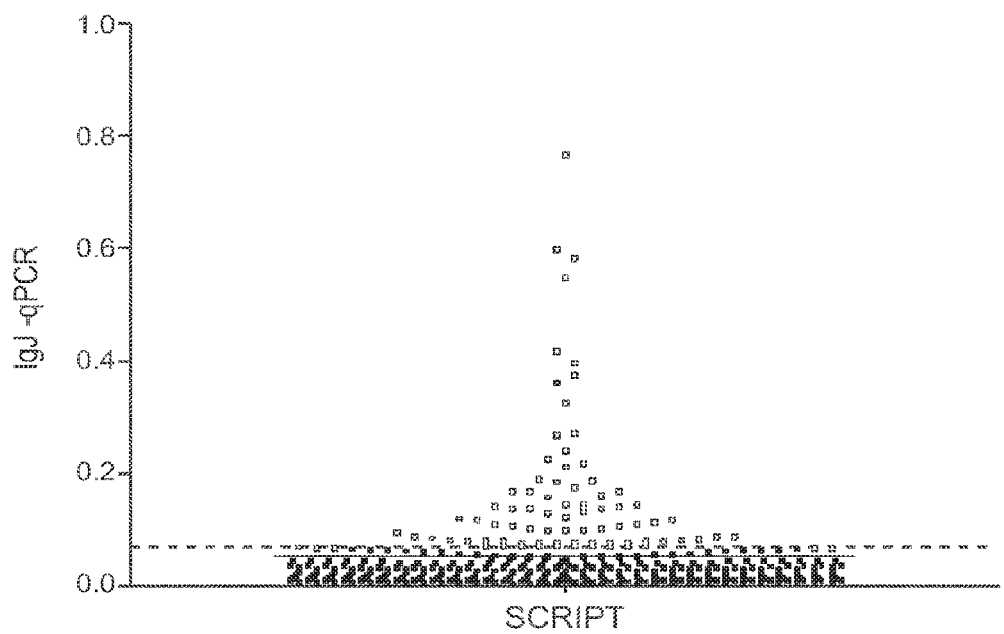
FIG. 6 shows baseline IgJ mRNA levels assayed by RT-qPCR in the SCRIPT ocrelizumab trial as described in Example 1.

For SCRIPT, due to our use of non-amplified RNA, we prospectively applied the overall percentage thresholds derived from the active arm samples from the three rituximab studies in the analysis. Thus for SCRIPT, $IgJ^{hi}$ was defined as the top 20% of samples (FIG. 6), and $FCRL5^{lo}$ was defined as the bottom 15% of samples. The prospectively defined cutoff of the highest 20th percentile of IgJ abundance used to determine $IgJ^{hi}$ biomarker status in SCRIPT is indicated by the dotted line in FIG. 6. Individual with IgJ levels above the 20% threshold are shown as open squares.

Differences in ACR20, ACR50, ACR70, ACRn, and DAS28 responses between active and placebo arms for the biomarker positive and negative patient subsets in the test and replication cohorts were calculated, and P-values determined. For categorical variables (ACR20, ACR50, ACR70) two separate contingency tables, one for the active arm and one for the placebo arm, were created for each cohort (test, replication and all) to compare the proportion of responders in the biomarker positive vs. biomarker negative subsets. Statistical significance was calculated using Fisher's exact test, and 2-tailed P-values were calculated. Odds ratios and inferential statistical calculations were performed using the R Language for Statistical Computing. Confidence intervals for odds ratios were based on the two-tailed Fisher's Exact test. P-values for DAS28 scores were derived from the two-tailed Student's t-test. Correlation coefficients were calculated using Pearson correlation coefficients. Clustering was performed using Treeview software (Page, R. D. M., Computer Applications in the Biosciences 1996 12: 357-358.).

Results

RT-qPCR mRNA Assays for B Lineage Cells in Whole Blood

We first set out to develop an mRNA-based method to detect and quantify B cells in whole blood. Multiplex reverse transcriptase-quantitative PCR (RT-qPCR) analysis was performed on whole blood RNA samples from patients receiving B cell depletion (rituximab or ocrelizumab) therapy, including samples from pre-therapy baseline, and days 15 and 84 post-B cell depletion. RT-qPCR assays were designed for CD19, CD20 and a B cell specific splice variant of FCRL5/IRTA2c, all markers of mature B cells. Additional assays were designed for J-chain (IgJ) and BCMA, genes highly enriched in B plasmablasts and plasma cells. Flow cytometry was performed at baseline and days 15 and 84 post-therapy, and Agilent gene expression microarray data were generated for a subset of the samples (baseline and day 84) (see Methods above).

Figure 1B:
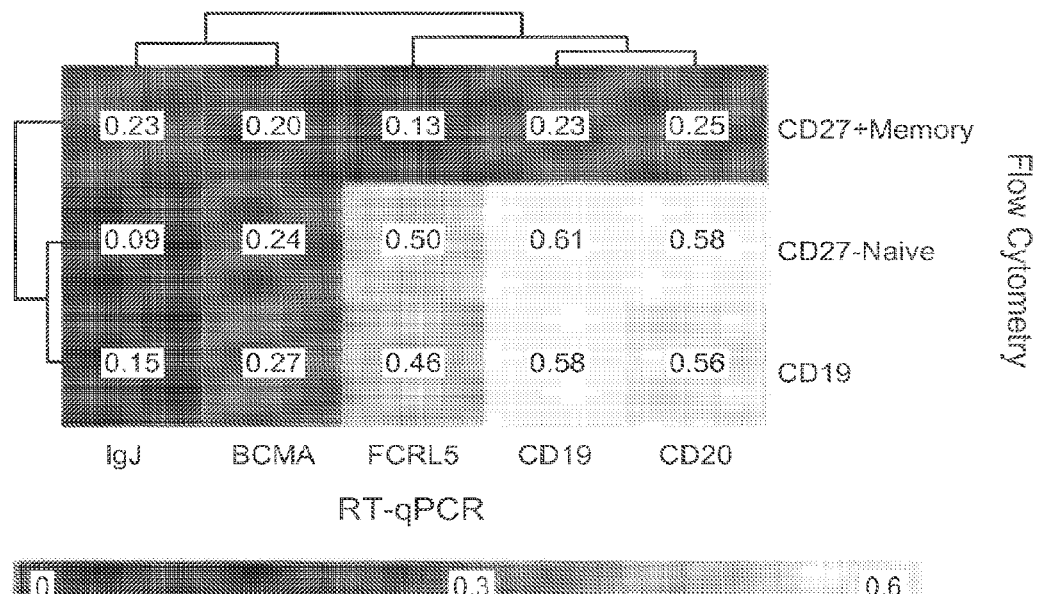

We found high-level concordance between B cell gene expression levels as determined by CD20 mRNA RT-qPCR analysis and absolute CD19+ cell counts as determined by flow cytometry ($r^2$=0.52, P<0.0001) (FIG. 1A). For the experiment shown in FIG. 1A, CD19 positive B cells in blood (cells/µl; y axis) were quantitated using flow cytometry in a total of 186 samples collected at various timepoints from patients undergoing anti-CD20 B cell depletion therapy. Whole blood RNAs sampled at the same time were assayed for CD20 expression levels (x axis) using RT-qPCR (see Methods above), and a Pearson correlation coefficient was calculated. Importantly, the RT-qPCR method retained high sensitivity at low B cell levels. Using multivariate correlation plots and unsupervised clustering, the 5 tested genes partitioned into two independent marker sets (FIG. 1B). For the results shown in FIG. 1B, correlation coefficients were calculated between RT-qPCR mRNA expression levels of plasmablasts (IgJ and BCMA) and mature B cell markers (FCRL5, CD19 and CD20) and various B cell subsets as determined by flow cytometry, and then visualized using unsupervised clustering. Expression of CD19, CD20 and FCRL5 correlated with each other (r>0.75) and with absolute CD19+ and CD27− naïve B cell counts (r>0.45). IgJ and BCMA were correlated with each other (r>0.8), but were poorly correlated with CD19+, CD27− naïve or CD27+ memory B cell counts. The two mRNA marker groups showed only low-level correlation with each other (r<0.4) (FIG. 1B and Table 1).

TABLE 1

Correlation coefficients for RT-qPCR mRNA levels between plasmablast/plasma cell markers (BCMA, IgJ) and mature/memory B cell markers (CD19, CD20, FCRL5).

|       | BCMA | IgJ  | CD19 | CD20 | FCRL5 |
|-------|------|------|------|------|-------|
| BCMA  | 1.00 | 0.87 | 0.38 | 0.42 | 0.40  |
| IgJ   | 0.87 | 1.00 | 0.13 | 0.15 | 0.18  |
| CD19  | 0.38 | 0.13 | 1.00 | 0.86 | 0.74  |
| CD20  | 0.42 | 0.15 | 0.86 | 1.00 | 0.74  |
| FCRL5 | 0.40 | 0.18 | 0.74 | 0.74 | 1.00  |

Figure 1C:
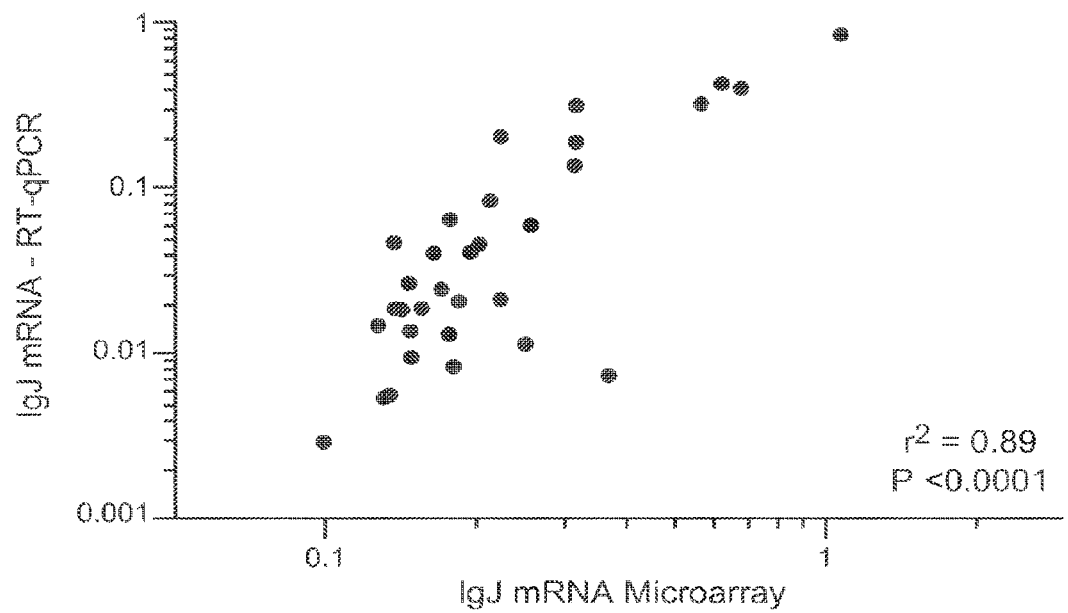

Blood B cell transcript levels measured by RT-qPCR were significantly correlated with mRNA levels quantified using Agilent whole-genome gene expression microarrays (FIG. 1C), however the dynamic range for detection of low abundance transcripts was significantly extended using the RT-qPCR method. This was important for the overall strategy of using these assays for the detection and quantitation of rare B lineage cells in whole blood. For the results shown in FIG. 1C, whole blood RNAs from patients receiving B cell depletion therapy at baseline (n=10), day 15 (n=10) and day 84 (n=10) were assayed for IgJ using RT-qPCR (y axis) and by Agilent whole genome mRNA microarray analysis (x axis), and a Pearson correlation coefficient was calculated.

Baseline IgJ and FCRL5 mRNA Levels as Biomarkers for Rituximab Response

The REFLEX trial of rituximab therapy in anti-TNF inadequate responders (Cohen S B, et al., Arthritis Rheum. 2006; 54 (9): 2793-806) was used as a training set to identify baseline mRNA biomarkers predictive of treatment response. Baseline RNA was available from 141 REFLEX study participants (118 in the rituximab treatment arm, 23 in the placebo arm). Clinical and laboratory data at baseline for the REFLEX cohort are provided in Table 2. There were no significant differences in baseline parameters between the training set studied here and the overall REFLEX study population (Table 3).

TABLE 2

Baseline clinical and demographic data for the REFLEX, DANCER, SERENE and SCRIPT RA cohorts.

| Baseline Characteristics | REFLEX N = 141 Mean ± SD | DANCER N = 142 Mean ± SD | SERENE N = 151 Mean ± SD | P value[a] | SCRIPT N = 413 Mean ± SD |
|---|---|---|---|---|---|
| Age (years) | 52 ± 12 | 52 ± 12 | 49 ± 13 | 0.044 | 54 ± 11 |
| Gender (% female) | 80 | 82 | 85 | NS | 77 |
| RA duration (years) | 12 ± 8 | 11 ± 9 | 6 ± 6 | $3.2 \times 10^{-10}$ | 12 ± 9 |
| Rheumatoid Factor (% positive) | 76 | 77 | 84 | NS | 92 |
| Swollen Joint Count | 14 ± 6 | 13 ± 5 | 14 ± 6 | NS | 18.3 ± 11.8 |
| Tender Joint Count | 17 ± 7 | 17 ± 6 | 15 ± 7 | 0.022 | 29.5 ± 15.8 |
| DAS28 | 6.8 ± 0.9 | 6.7 ± 0.8 | 6.5 ± 1 | 0.036 | 6.0 ± 1.0 |
| C-Reactive Protein (mg/dl) | 3.6 ± 4 | 3.2 ± 4 | 2 ± 2 | $3.2 \times 10^{-5}$ | 2.6 ± 2.7 |
| IgG | 13 ± 4 | 12 ± 3 | 13 ± 4 | NS | |
| IgM | 1.7 ± 0.9 | 1.5 ± 0.7 | 1.5 ± 0.9 | NS | |
| IgA | 3 ± 2 | 3 ± 1 | 3 ± 1 | NS | |

[a]For continuous variables, P-values were derived from one way ANOVA. For categorical variables, P-values were derived from a $X^2$ statistical test. Significant p-values (<0.05) are shown; NS = not signficant.
IgG (normal range 5.5-16.5 g/L),
IgM (normal range 0.4-2.0 g/L),
IgA (normal range 0.8-4.0 g/L).

TABLE 3

Baseline demographics and clinical features in sampled subsets as compared to the overall trial populations.

| Baseline Characteristics | REFLEX All N = 518 | REFLEX Sample N = 141 | DANCER All N = 462 | DANCER Sample N = 142 | SERENE All N = 509 | SERENE Sample N = 151 | SCRIPT All N = 840 | SCRIPT Sample N = 413 |
|---|---|---|---|---|---|---|---|---|
| Age (years) | 52 ± 12 | 52 ± 12 | 51 ± 12 | 52 ± 12 | 52 ± 13 | 49 ± 13 | 54 ± 11 | 54 ± 11 |
| Gender (% female) | 82 | 80 | 81 | 82 | 82 | 85 | 80 | 77 |
| RA duration (years) | 12 ± 8 | 12 ± 7 | 10 ± 8 | 11 ± 9 | 7 ± 7 | 6 ± 5 | 12 ± 9 | 12 ± 9 |
| Rheumatoid factor (%) | 76 | 76 | 80 | 77 | 86 | 84 | 89 | 92 |
| Swolien joint count (28 joints assessed) | 14.7 ± 5.9 | 14.3 ± 5.9 | 13.9 ± 5.6 | 13.4 ± 5.1 | 13.1 ± 5.6 | 13.4 ± 5.9 | 17.0 ± 11.3 | 18.3 ± 11.8 |
| Tender joint count (28 joints assessed) | 17.0 ± 7.1 | 16.9 ± 7.2 | 17.6 ± 6.4 | 16.7 ± 6.4 | 15.0 ± 6.8 | 14.9 ± 7.1 | 26.2 ± 15.7 | 29.5 ± 15.8 |

TABLE 3-continued

Baseline demographics and clinical features in sampled subsets as compared to the overall trial populations.

| Baseline Characteristics | REFLEX | | DANCER | | SERENE | | SCRIPT | |
|---|---|---|---|---|---|---|---|---|
| | All N = 518 | Sample N = 141 | All N = 462 | Sample N = 142 | All N = 509 | Sample N = 151 | All N = 840 | Sample N = 413 |
| DAS28 | 6.9 ± 1.0 | 6.8 ± 0.9 | 6.8 ± 0.9 | 6.7 ± 0.9 | 6.5 ± 1.0 | 6.5 ± 1.0 | 5.9 ± 1.1 | 6.0 ± 1.0 |
| CD19 (cells/ul) | 197 ± 157 | 201 ± 189 | 174 ± 143 | 162 ± 117 | 199 ± 171 | 228 ± 145 | | |
| C-Reactive Protein (mg/dl) | 3.8 ± 3.9 | 3.6 ± 3.6 | 3.1 ± 3.2 | 3.2 ± 3.6 | 2.1 ± 2.3 | 2.0 ± 1.9 | 2.8 ± 2.9 | 2.6 ± 2.7 |
| IgG* | 13 ± 4 | 13 ± 4 | 13 ± 4 | 12 ± 3 | 14 ± 4 | 13 ± 4 | | |
| IgM* | 1.6 ± 0.9 | 1.7 ± 0.8 | 1.6 ± 0.8 | 1.5 ± 0.7 | 1.5 ± 0.8 | 1.5 ± 0.9 | | |
| IgA* | 3 ± 1 | 3 ± 1 | 3 ± 1 | 3 ± 1 | 3 ± 1 | 3 ± 2 | | |

*IgG (normal range 5.5-16.5 g/L), IgM (normal range 0.4-2.0 g/L), IgA (normal range 0.8-4.0 g/L).

The ACR50 response rate at 24 weeks, which denotes a 50% improvement in signs and symptoms of active RA, was used as the primary outcome measure for this study. The ACR50 rate in the active arm of the REFLEX patient cohort for which mRNA samples were available was 25%, compared with 17% in the placebo arm. In comparison, the overall REFLEX trial population had an ACR50 rate of 27% in the active arm (n=298), and 5% in the placebo arm (n=201).

Figure 1D:
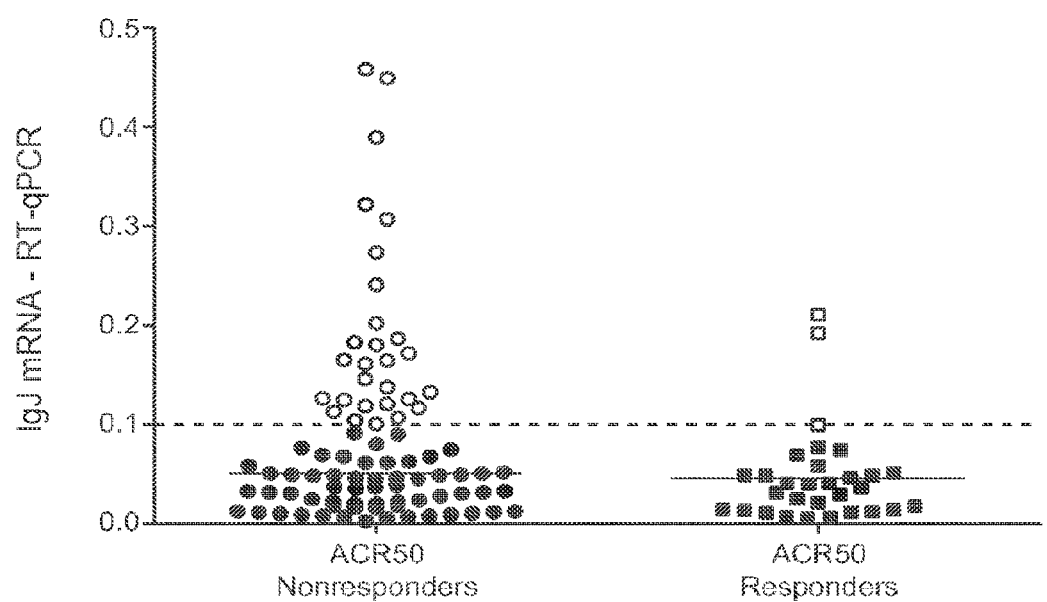

Baseline IgJ mRNA levels assayed by RT-qPCR in whole blood were compared in ACR50 nonresponders (n=88) and responders (n=30) from the active arm of the REFLEX trial of rituximab in RA. As shown in FIG. 1D, mean baseline mRNA expression levels of IgJ (and BCMA, data not shown) were slightly higher in patients who failed to achieve ACR50 response rates at week 24 (P=0.03), and there was a significant enrichment of ACR50 nonresponders in the subgroup of patients with baseline IgJ above a threshold of 0.1 mRNA expression units. There were no statistically significant differences in baseline expression of CD20, CD19 or FCRL5 between the two patient subgroups (data not shown). Formal threshold analysis indicated that baseline IgJ and BCMA expression had the best ability to distinguish between ACR50 responders and non-responders (see below). In contrast, as shown in FIGS. 2A and B, CD19 and FCRL5 (also CD20, data not shown), as single baseline markers, did not significantly stratify the population for response. Biomarker thresholds were established using a formal threshold analysis technique as described in the Methods above.

We next applied the IgJ$^{hi}$ biomarker to the available samples from two additional independent rituximab RA studies, DANCER (Emery et al., Arthritis Rheum. 2006; 54:1390-1400) and SERENE (Emery et al., Ann. Rheum. Dis. 2010; 69:1629-1635), and the ocrelizumab RA study SCRIPT. DANCER was a phase II study that enrolled both TNF-inadequate responders (TNF-IR) and methotrexate-IR (MTX-IR) subjects, SERENE was a phase III study that enrolled only MTX-IR subjects, and SCRIPT was a phase III study that enrolled TNF-IR subjects (see Methods above). Together, the three replication cohorts comprised 475 anti-CD20-treated (297 TNF-IR and 178 MTX-IR) and 228 placebo-treated (144 TNF-IR and 84 MTX-IR) subjects. Analysis of baseline clinical and demographic data showed a generally balanced distribution of subject age, gender, and seropositivity between the replication cohorts and the original REFLEX test cohort (Table 2). The observed baseline differences in disease duration, tender, and swollen joint counts and CRP reflected individual trial inclusion criteria (Table 2).

As shown in FIG. 3, an RA subgroup was defined by an IgJ mRNA biomarker that demonstrated reduced efficacy after anti-CD20 therapy. FIG. 3A shows the identification of optimal biomarker thresholds for IgJ as a predictor of ACR50 response rates at 6 months (day 168) following assessment of baseline mRNA samples from the REFLEX trial of rituximab in RA. In FIGS. 3A-D, subjects treated with anti-CD20 are indicated by hatched bars; subjects who received placebo are indicated by open bars. The biomarker threshold (IgJ ≥ or <0.1 expression units) was then tested prospectively in baseline mRNA samples from the DANCER and SERENE trials of rituximab in RA. Biomarker thresholds for the SCRIPT trial of ocrelizumab in RA were based on percentage thresholds from rituximab studies.

Figure 3A:
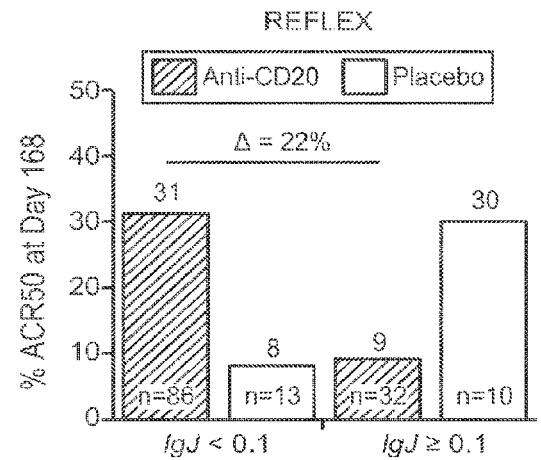
FIGS. 3A-3E show IgJ biomarker in mRNA samples from patients following anti-CD20 therapy or placebo as described in Example 1.
Figure 3B:
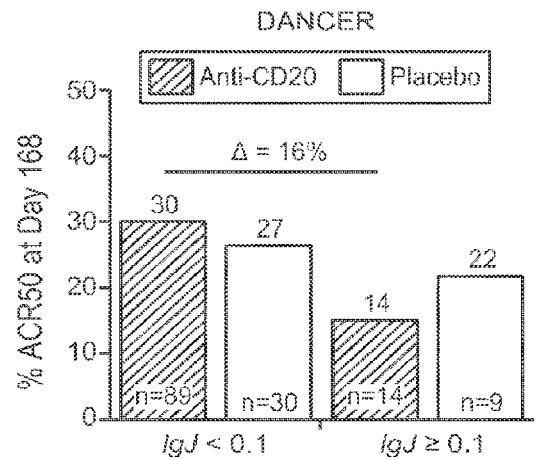
Figure 3C:
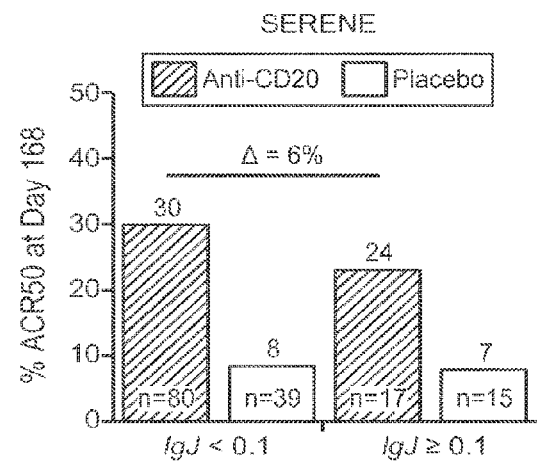
Figure 3D:
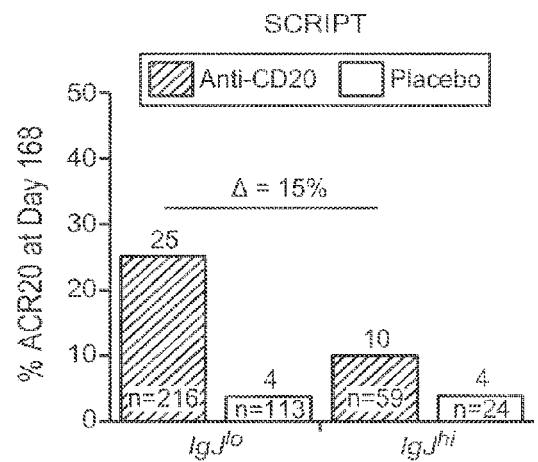
Figure 3E:
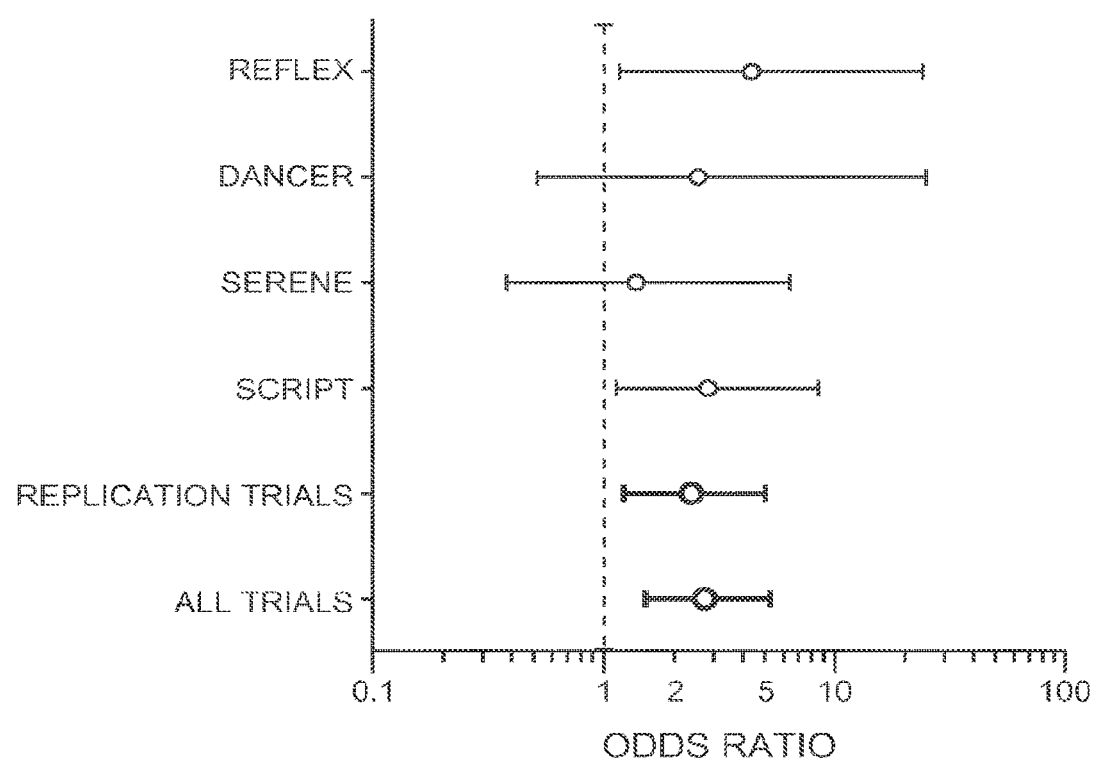

Application of the pre-established IgJ single biomarker threshold (IgJ ≥0.1 units) to DANCER resulted in a 16% enrichment of ACR50 rates for the IgJ$^{lo}$ subset (30% in IgJ$^{lo}$ vs. 14% in IgJ$^{hi}$; FIG. 3B), and a 6% enrichment in SERENE (30% in IgJ$^{lo}$ vs. 24% in IgJ$^{hi}$; FIG. 3C). For SCRIPT, non-amplified RNA was used for the biomarker assays and thus the precise expression threshold established in REFLEX could not be applied to SCRIPT samples. Instead, the pre-determined overall percentage threshold from the rituximab studies –IgJ$^{hi}$ defined as the top 20% of samples— was applied prospectively to the SCRIPT IgJ biomarker analysis. Using this threshold, there was a 15% enrichment in ACR50 rates in the SCRIPT IgJ$^{lo}$ as compared to the IgJ$^{hi}$ subset (25% in IgJ$^{lo}$ vs. 10% in IgJ$^{hi}$; FIG. 3D). In FIGS. 3A-D, Δ denotes the ACR50 percentage difference for the active anti-CD20 arm between the IgJ$^{hi}$ and IgJ$^{lo}$ subgroups, "n" refers to the number of individual subjects I each subgroup, and the number above the bars is the % ACR50 for each subgroup. FIG. 3E shows odds ratios and 95% c.i. for the enrichment of ACR50 responses in the IgJ$^{lo}$ subgroup as compared to the IgJ$^{hi}$ subgroup for the individual trials, the replication trials in aggregate (DANCER, SERENE and SCRIPT), and for all trials together. Each of the trials showed similar trends of improved ACR50 rates in the IgJ$^{lo}$ as compared to IgJ$^{hi}$ subsets (biomarker odds ratios for the four trials were 4.4, 2.6, 1.4 and 2.9 for REFLEX, DANCER, SERENE and SCRIPT, respectively). In a combined analysis of the three replication cohorts (DANCER, SERENE and SCRIPT), the overall ACR50 response rate was 27% for the IgJ$^{lo}$ group (n=385) and 13% for the IgJ$^{hi}$ group (n=90) ($P_{REPLICATION}$=0.006; OR=2.4, 95% c.i. (1.2, 5.0); FIG. 2E), with non-significant differences between the placebo arms (9% and 8%, respectively; P=1.0). When all four trials were combined, the ACR50 response rate in the active arms was 28% for the IgJ$^{lo}$ group (n=47) and 12% for the IgJ$^{hi}$ group (n=122) (OR=2.7; 95% c.i. (1.5, 5.3); FIG. 3E).

Figure 4A:
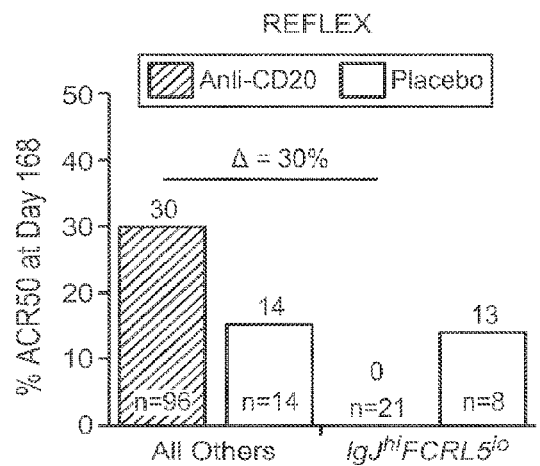
FIGS. 4A-4E show IgJ/FCRL5 biomarkers in mRNA samples from patients following anti-CD20 therapy or placebo as described in Example 1.
Figure 4B:
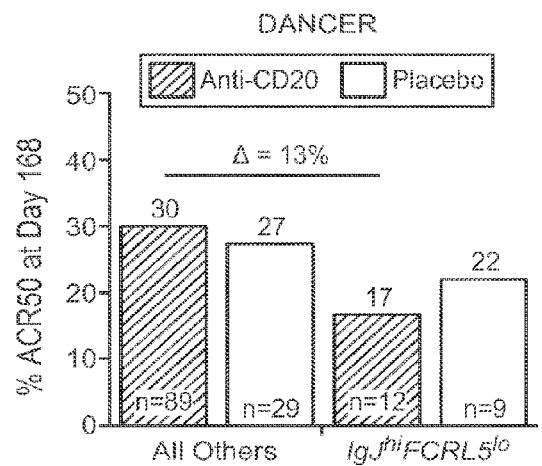
Figure 4C:
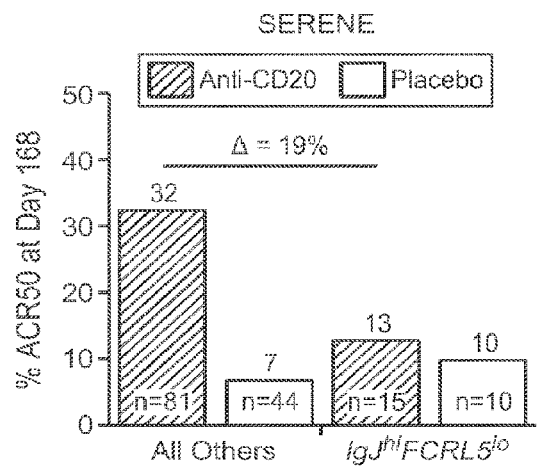
Figure 4D:
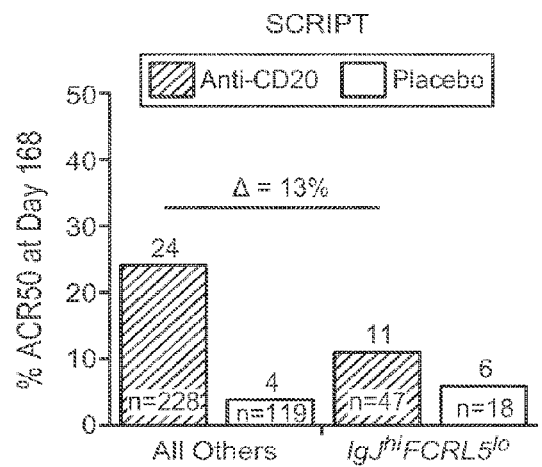
Figure 4E:
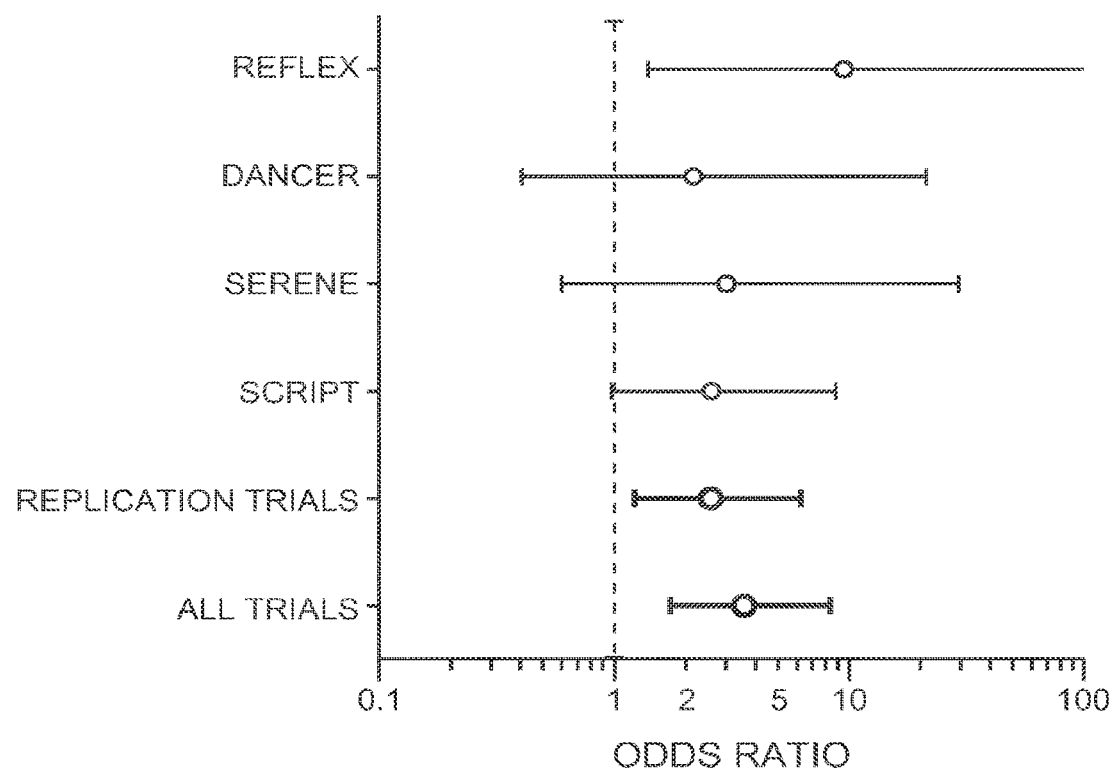

Having established that a single plasmablast biomarker could enrich for anti-CD20 non-responders across these trials, we next sought to determine whether a second biomarker could further increase the test predictive value. The combination of IgJ and BCMA, both plasmablast markers, showed no further significant enrichment over IgJ alone (data not shown). However, the combination of IgJ ≥0.1 (IgJ$^{hi}$) and low levels of FCRL5 (<0.02, FCRL5$^{lo}$) excluded all the ACR50 responders in the active arm as shown in FIG. 4A. The response rates for the two biomarker-defined groups (IgJ$^{hi}$ FCRL5$^{lo}$ vs. all others) were highly different (0% ACR50 for IgJ$^{hi}$ FCRL5$^{lo}$, 30% ACR50 for all others). Subsetting the placebo arm using the two-biomarker combination resulted in similar ACR50 response rates, suggesting that this biomarker combination was predictive, rather than prognostic, for response to rituximab (FIG. 4A). An IgJ$^{hi}$ CD19$^{lo}$ biomarker combination showed similar ability to discriminate subsets for ACR50 (FIG. 2C) and other outcome measures (not shown), suggesting that the combination of high levels of plasmablast mRNA and low levels of naïve/memory B cell mRNA at baseline was a negative predictor of efficacy for anti-CD20.

Application of the IgJ$^{hi}$/FCRL$^{lo}$ combination biomarker thresholds to the samples from DANCER, SERENE, and SCRIPT resulted in enriched ACR50 response rates in the biomarker negative subsets (FIGS. 4, B, C and D, respectively). For the rituximab trials, the IgJ$^{hi}$ FCRL5$^{lo}$ biomarker was defined as IgJ expression ≥0.1 and FCRL5 expression <0.02. For SCRIPT, the combination biomarker was based on pre-defined percentage thresholds based on the rituximab studies: IgJ$^{hi}$—highest 20th percentile; FCRL5$^{lo}$—the lowest 15th percentile. The "All Others" subgroups were comprised of those individuals in each trial who were IgJ$^{lo}$ together with those who were IgJ$^{hi}$ FCRL5$^{hi}$. "n" refers to the number of individual subjects in each subgroup, and the number above the bars is the % ACR50 for each subgroup. For the replication samples, the overall ACR50 rate in the treatment group was 27% for the biomarker negative subgroup (n=398) and 12% for the IgJ$^{hi}$ FCRL5$^{lo}$ group (n=74) ($P_{REPLICATION}$=0.008; OR2.7, 95% c.i. (1.3, 6.3); FIG. 4E), with non-significant differences between the placebo arms (8% and 11%, respectively; P=0.5). When data from the four trials were combined, the ACR50 response rate for the treatment groups was 28% for the biomarker negative subgroup (n=494) and 9% for the IgJ$^{hi}$ FCRL5$^{lo}$ group (n=95) (OR=3.6, 95% c.i. (1.8, 8.4); FIG. 4E). In total, the IgJ$^{hi}$ FCRL5$^{lo}$ non-responder subgroup comprised 17% of the subjects studied.

Application of the IgJ and IgJ-FCRL5 Biomarkers to Other Clinical Outcomes

Figure 5A:
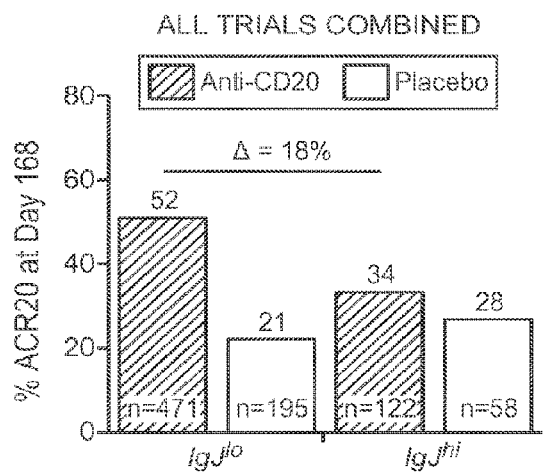
FIGS. 5A-5F show ACR20 (FIGS. 5A, 5D), ACR70 (FIGS. 5B, 5E) and Δ DAS28 (FIGS. 5C, 5F) results stratified by the IgJ (FIGS. 5A-5C) and IgJ$^{hi}$ FCRL5$^{lo}$ (FIGS. 5D-5F) biomarkers across all trials as described in Example 1.
Figure 5B:
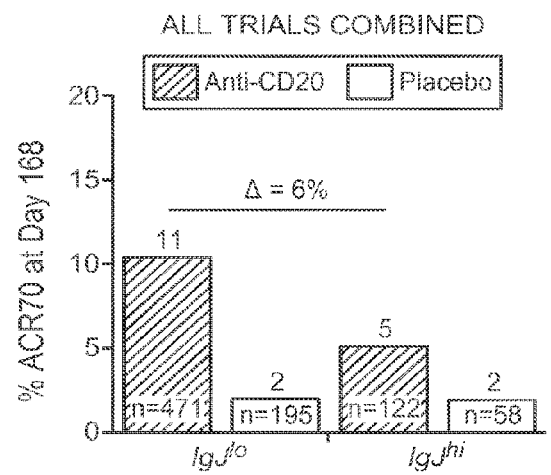
Figure 5C:
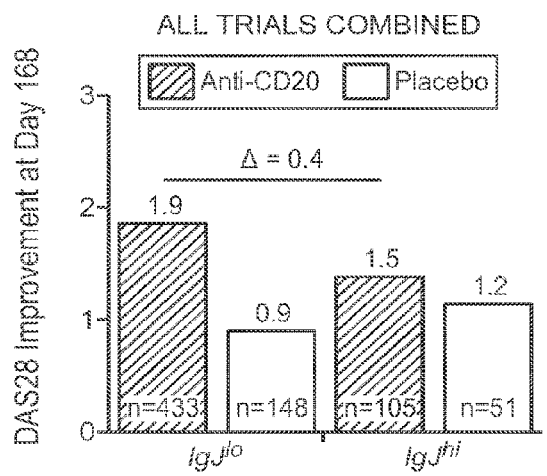
Figure 5D:
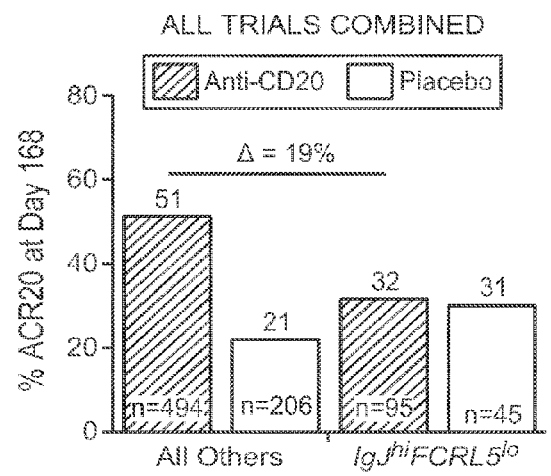
Figure 5E:
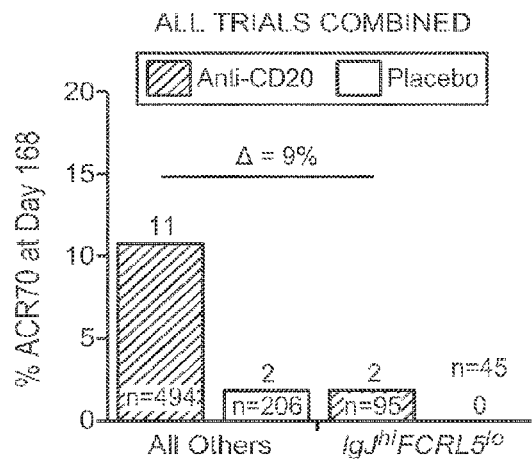
Figure 5F:
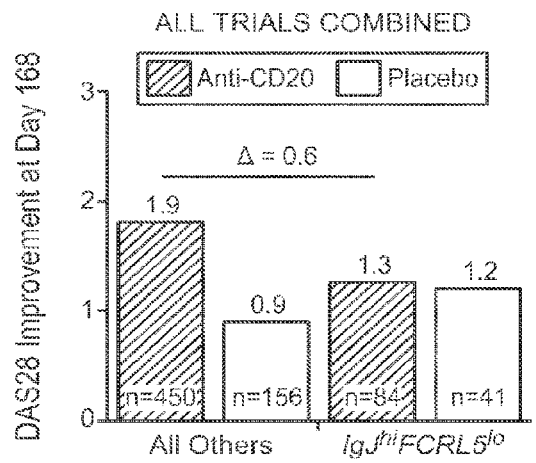

In the combined sample of all four trials, active arm subsets defined by both the IgJ biomarker (FIGS. 5A-C) and the IgJ-FCRL5 combination biomarker (FIGS. 5D-F) also showed differences in ACR20, ACR70, and DAS28 response rates at 6 months. In the figure, hatched bars show the indicated response rates at 6 months (day 168) for patients treated with anti-CD20; open bars show the indicated response rates at 6 months (day 168) for patients that received placebo. Δ in each of the panels denotes the respective ACR percentage difference for the active anti-CD20 arm between the IgJ$^{lo}$ and IgJ$^{hi}$ (A-C) subgroups or between all others and IgJ$^{hi}$ FCRL5$^{lo}$ (D-F). "n" refers to the number of individual patients in each subgroup, and the number above the bars is the % for each subgroup. The IgJ$^{hi}$ FCRL5$^{lo}$ subgroup had IgJ expression ≥0.1 and FCRL5 expression <0.02. The "All Others" subgroups in panels D-F were comprised of all individuals with baseline IgJ <0.1 plus the individuals who were IgJ ≥0.1 and FCRL5 ≥0.02.

An analysis of baseline clinical and demographic data between the biomarker defined IgJ$^{hi}$ and IgJ$^{lo}$ subgroups showed that the two subsets were highly similar (Table 4). Similarly, no significant differences were observed in baseline clinical and demographic data defined by the IgJ-FCRL5 combination biomarker (Table 6). We also compared baseline parameters and clinical outcomes for the TNF-IR and MTX-IR subgroups across the three rituximab trials. Consistent with more severe disease overall, TNF-IR subjects had a longer duration of disease, higher CRP levels, and higher baseline DAS28 scores than MTX-IR subjects (Table 5). Of interest, data from the rituximab studies indicated that the IgJ$^{hi}$ biomarker subset was enriched in TNF-IR as compared to MTX-IR subjects (30% vs. 18%, respectively; P=0.01), suggesting the possibility that the IgJ$^{hi}$ subset of RA may also be somewhat resistant to treatment with anti-TNF agents.

TABLE 4

Baseline demographic and clinical data in the IgJ$^{lo}$ and IgJ$^{hi}$ biomarker subgroups[a].

| Baseline Characteristics | IgJ$^{lo}$ | | IgJ$^{hi}$ | | |
|---|---|---|---|---|---|
| | Mean ± SD | N | Mean ± SD | N | P-value[b] |
| Age (years) | 52 ± 12 | 667 | 52 ± 12 | 180 | NS |
| RA duration (years) | 10 ± 9 | 667 | 11 ± 9 | 180 | NS |
| Swollen joint count (28 joints assessed) | 16.2 ± 9.7 | 666 | 15.7 ± 8.6 | 180 | NS |
| Tender Joint Count (28 joints assessed) | 23.0 ± 14.5 | 666 | 21.2 ± 11.0 | 180 | NS |
| DAS28 | 6.3 ± 1.0 | 661 | 6.4 ± 1.1 | 180 | NS |
| C-Reactive Protein (mg/dl) | 2.9 ± 3.0 | 661 | 2.4 ± 2.5 | 179 | NS |
| | (%) | N | (%) | N | P-value[c] |
| Gender (% female) | 79 | 667 | 84 | 180 | NS |
| Rheumatoid Factor (%) | 86 | 618 | 78 | 171 | NS |

[a]Data were pooled from the REFLEX, DANCER, SERENE, and SCRIPT trials.
[b]2-tailed P-values were derived from non-parametric Wilcoxon test. NS—not significant, P ≥ 0.05.
[c]2-tailed P-values were derived from Fisher Exact test. NS—not significant, P ≥ 0.05.

TABLE 5

Baseline demographic and clinical data for methotrexate (MTX-IR) and TNF (TNF-IR) inadequate responders from the rituximab studies[a].

| Baseline Characteristics | MTX-IR N = 262 Mean ± SD | TNF-IR N = 172 Mean ± SD | P value[b] |
|---|---|---|---|
| Age (years) | 51 ± 13 | 52 ± 12 | NS |
| RA duration (years) | 8 ± 8 | 11 ± 8 | 1.9 × 10$^{-8}$ |
| Swollen joint count (28 joints assessed) | 13.5 ± 5.5 | 14.4 ± 5.8 | NS |
| Tender Joint Count (28 joints assessed) | 15.6 ± 6.8 | 16.9 ± 7.1 | NS |
| DAS28 | 6.6 ± 0.9 | 6.8 ± 0.9 | 0.013 |
| C-Reactive Protein (mg/dl) | 2.5 ± 2.8 | 3.5 ± 3.6 | 1.6 × 10$^{-5}$ |

TABLE 5-continued

Baseline demographic and clinical data for methotrexate (MTX-IR) and TNF (TNF-IR) inadequate responders from the rituximab studies[a].

| Baseline Characteristics | % | % | P value[c] |
|---|---|---|---|
| Rheumatoid Factor (%) | 82 | 75 | NS |
| Gender (% female) | 83 | 81 | NS |
| IgJ$^{hi}$ (%) | 18 | 30 | 0.01 |

[a]Data were pooled from the REFLEX, DANCER and SERENE rituximab trials.
[b]P-values were derived from nonparametric Wilcoxon test. NS—not significant, P ≥ 0.05.
[c]2-tailed P-values were derived from Fisher Exact test. NS—not significant, P ≥ 0.05.

TABLE 6

Distribution of baseline demographic data between two IgJ/FCRL5 biomarker subgroups in all subjects studied.

| Baseline Characteristics | All Others | | IgJ$^{hi}$ FCRL5$^{lo}$ | | |
|---|---|---|---|---|---|
| | Mean ± SD | N | Mean ± SD | N | P-value |
| Age (years) | 53 ± 12 | 705 | 52 ± 12 | 141 | NS |
| RA Duration (years) | 11 ± 8 | 705 | 10.8 ± 9.3 | 141 | NS |
| Swollen joint count (28 joints assessed) | 16.2 ± 9.6 | 704 | 15.6 ± 8.8 | 141 | NS |
| Tender joint count (28 joints assessed) | 23.0 ± 14.3 | 704 | 20.7 ± 11.2 | 141 | NS |
| DAS28 | 6.4 ± 1.0 | 699 | 6.3 ± 1.1 | 141 | NS |
| C-Reactive Protein (mg/dl) | 2.8 ± 3.0 | 699 | 2.5 ± 2.75 | 140 | NS |
| Baseline Characteristics | % | N | % | N | P-value |
| Rheumatoid factor (%) | 86 | 653 | 81 | 135 | NS |
| Gender (% female) | 82 | 705 | 82 | 141 | NS |

[a]Data were pooled from the REFLEX, DANCER, SERENE and SCRIPT trials. P-values were derived from Wilcoxon non parametric test.

Discussion

Previous studies have attempted to correlate biologic sequelae that follow rituximab-induced B cell depletion with clinical outcomes in RA. A persistence of B cells in the peripheral blood in the weeks following rituximab therapy (Dass S, et al., Arthritis Rheum. 2008; 58 (10): 2993-9) or incomplete depletion of synovial B cells at Week 4 (Teng Y K, et al., Arthritis Rheum. 2007; 56 (12): 3909-18) correlated with impaired response rates in RA. Reconstitution of the B lineage with early development stage B cells (e.g. CD10+ immature B cells) may be a sign of deeper B cell depletion and was associated with better rituximab response rates (Leandro M J, et al., Arthritis Rheum. 2006; 54 (2): 613-20), whereas reconstitution with memory phenotype B cells (CD27+) was associated with lower response rates (Roll, P., et al., Arthritis Rheum. 2008; 58: 1566-1575). The cells that resist B cell depletion include B plasmablasts that express surface markers such as CD27 and CD38, but lack CD20 (Palanichamy A, et al., Arthritis Rheum. 2008; 58 (12): 3665-3674).

In the current study, we hypothesized that baseline numbers of CD20-negative plasmablasts might be predictive of response to anti-CD20 treatment in RA, and developed RT-qPCR assays to quantitate plasmablast-specific gene expression in whole blood RNA samples to provide estimates of the cellular composition of blood prior to therapy. Using data and samples from four randomized, placebo controlled studies of rituximab or ocrelizumab in RA, we found that elevated baseline levels of the plasmablast-specific transcript IgJ, either as a single marker or in combination with low levels of a mature B cell splice variant of FCRL5, defined a ~17-20% subpopulation of RA that showed response rates that were not different than placebo. Furthermore, these biomarkers were not simply prognostic for more severe and treatment-resistant disease, but rather were predictive markers for anti-CD20 response. Importantly, these are baseline measurements that can be made prior to initiation of therapy and have the potential to be standardized for routine clinical use. Based on the data presented here, we conclude that patients who are positive for the mRNA biomarkers IgJ$^{hi}$ or IgJ$^{hi}$ FCRL5$^{lo}$ at baseline are less likely to receive benefit from anti-CD20 treatment.

A recent publication provides support for certain conclusions presented here (Vital E M, et al., Arthritis Rheum. 2010 May; 62(5):1273-9). In an observational trial of rituximab outcomes in RA, Vital et al. showed that the number of baseline plasmablast cells in blood (CD27++CD38++ as determined by flow cytometry) was significantly higher in first cycle rituximab non-responders (n=32) as compared to responders (n=54) (OR=0.47; 95% CI 0.28-0.27; P=0.003) (Id.). First cycle rituximab non-responders were also more likely to have incomplete depletion of B lineage cells following therapy. While the numbers of patients studied were relatively small and the data were not from randomized and placebo controlled subjects, these data nevertheless are consistent with the idea that elevated levels of plasmablasts at baseline predict non-response to rituximab in RA.

Plasmablasts are not generally found at significant levels in the peripheral blood of healthy individuals, except following vaccination (Odendahl M, et al., Blood. 2005; 105 (4): 1614-21) or in the setting of acute and chronic infections (Jaimes M C, et al., J Virol. 2004; 78(20): 10967-76; Moir S. et al., Nat Rev Immunol. 2009; 9(4): 235-45). It is currently unclear whether circulating plasmablasts have a pathogenic role in autoimmunity, or are simply markers of a dysregulated and hyperactive immune system. The observation that elevated levels of blood plasmablasts return towards normal following immunosuppressive therapy in SLE and correlate with improvements in disease activity (Anolik J H, et al., Arthritis Rheum. 2004; 50(11): 3580-90) supports the idea that plasmablasts may have a role in disease pathogenesis.

Plasmablasts that escape B cell depletion by anti-CD20 may retain the ability to home to sites of inflammation (e.g. joints) through their expression of chemokine receptors such as CXCR3 and CXCR4 (Hauser A E, et al., J Immunol. 2002; 169(3): 1277-82). They may then contribute to disease through the local secretion of autoantibodies, which can activate macrophages via engagement of Fc receptors leading to inflammatory cytokine release (Clavel et al., Arthritis Rheum. 2008; 58:678-688). In addition, plasmablasts express high levels of BCMA, a high affinity receptor for the survival cytokine BAFF (Yang M, et al., J Immunol. 2007; 175(5): 2814-24). The striking elevations of BAFF that are observed following B cell depletion with anti-CD20 (Cambridge G, et al., Arthritis Rheum 2006; 54:723-732; Vallerskog T, et al., Arthritis Res Ther 2006; 8: R167) may specifically enhance the survival of circulating plasmablasts that escape depletion, thereby contributing to resistance to anti-CD20 therapy.

More generally, these data presented here demonstrate the value of large randomized, placebo-controlled clinical trial datasets for studies that aim to identify baseline biomarkers that can stratify patient subgroups for treatment responses.

Placebo arms are required for testing the efficacy of new therapies, and they are also essential for determining whether biomarkers for defined subgroups are merely prognostic vs. predictive. Prognostic markers stratify patients in terms of disease course or severity, and are not expected to necessarily show significant differences between the active and placebo arms. On the other hand, predictive markers stratify the active arm group but not the placebo arm. Predictive markers are valuable for personalized health care approaches since, once identified, they can assist in the targeting of individual drugs to the patients most likely to respond.

In summary, we have shown that elevated baseline blood expression of plasmablast mRNA markers, either alone or together with low levels of mature B cell markers, defines a ~17-20% subset of RA with an impaired response to standard B cell depletion therapy with rituximab at 6 months. It remains to be determined whether this subset of RA patients would benefit from additional courses of B cell depletion therapy, or whether they would respond to alternative available therapies. In addition, it will be interesting to determine whether these biomarkers will be useful in stratifying response rates in other diseases such as multiple sclerosis, including relapsing-remitting multiple sclerosis (Hauser et al., N Engl. J Med. 358(7):676-88 (2008)) and primary progressive multiple sclerosis (Hawker K, et. al., Ann Neurol. 2009 October; 66(4):460-71), and ANCA-associated vasculitis (Stone J H, et al., N Engl. J Med. 2010 Jul. 15; 363(3):221-32) where anti-CD20 therapy has shown clinical activity. Although an FDA-approved (or validated) diagnostic test in not currently available for clinical use, we propose that determination of baseline plasmablast levels has the potential to inform treatment decisions with anti-CD20 therapeutics in RA in order to maximize likely clinical benefit.

What is claimed is:

1. A method of treating rheumatoid arthritis in a human patient, comprising:
   (a) obtaining a blood sample from the human patient;
   (b) measuring mRNA expression of at least one gene in cells of the blood sample using a reverse transcriptase-quantitative polymerase chain reaction (RT-qPCR), wherein the at least one gene comprises IgJ, FCRL5 and CD19;
   (c) determining that the cells from the blood sample from the human patient express IgJ at an elevated level, and both FCRL5 and CD19 at a reduced level as compared to the expression of IgJ, FCRL5 and CD19 in a blood sample obtained from a control subject with rheumatoid arthritis who exhibits a favorable response to an anti-CD20 antibody, or to threshold values for IgJ, FCRL5 and CD19; and
   (d) administering a therapeutically effective amount of a therapeutic agent other than the anti-CD20 antibody to the human patient to treat the rheumatoid arthritis if the blood sample obtained from the human patient has been determined to express IgJ at an elevated level, and both FCRL5 and CD19 at a reduced level as compared to the control subject or to the threshold values in step (c), and wherein the therapeutic agent is an interleukin-6-receptor antagonist or abatacept.

2. The method of claim 1, wherein the anti-CD20 antibody is rituximab.

3. The method of claim 1, wherein the anti-CD20 antibody is ocrelizumab.

4. The method of claim 1, wherein the therapeutic agent other than the anti-CD20 antibody is an interleukin-6-receptor antagonist.

5. The method of claim 1, wherein the therapeutic agent other than the anti-CD20 antibody is abatacept.

6. The method of claim 1, wherein the threshold values are relative abundance values of greater than or equal to 0.1 IgJ, less than 0.02 FCRL5, and less than 0.05 CD19 when mRNA expression is normalized to mRNA expression of a housekeeping gene.

* * * * *